United States Patent
De Goeij et al.

(10) Patent No.: US 9,714,294 B2
(45) Date of Patent: Jul. 25, 2017

(54) MONOCLONAL ANTIBODIES AGAINST HER2 EPITOPE

(75) Inventors: Bart De Goeij, Maarssen (NL); Edward Norbert Van Den Brink, Halfweg (NL); Simone De Haij, Weesp (NL); Thilo Riedl, Arnhem (NL); Rene Hoet, Boxmeer (NL); Ole Baadsgaard, Hellerup (DK); David Satijn, Utrecht (NL); Jan Van De Winkel, Zeist (NL); Paul Parren, Odijk (NL)

(73) Assignee: GENMAB A/S, Copenhagen (DK)

( * ) Notice: Subject to any disclaimer, the term of this patent is extended or adjusted under 35 U.S.C. 154(b) by 617 days.

(21) Appl. No.: 13/700,246

(22) PCT Filed: May 27, 2011

(86) PCT No.: PCT/EP2011/058772
§ 371 (c)(1),
(2), (4) Date: Mar. 21, 2013

(87) PCT Pub. No.: WO2011/147982
PCT Pub. Date: Dec. 1, 2011

(65) Prior Publication Data
US 2013/0171148 A1 Jul. 4, 2013

Related U.S. Application Data

(60) Provisional application No. 61/349,182, filed on May 27, 2010.

(30) Foreign Application Priority Data

May 27, 2010 (DK) .................................. 2010 00468

(51) Int. Cl.
*C07K 16/30* (2006.01)
*A61K 39/395* (2006.01)
*C07K 16/32* (2006.01)
*A61K 39/00* (2006.01)

(52) U.S. Cl.
CPC .............. *C07K 16/30* (2013.01); *C07K 16/32* (2013.01); *A61K 2039/505* (2013.01); *C07K 2317/21* (2013.01); *C07K 2317/33* (2013.01); *C07K 2317/732* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,705,157 A | 1/1998 | Greene | |
| 6,123,939 A | 9/2000 | Shawver et al. | |
| 6,270,765 B1 | 8/2001 | Deo et al. | |
| 7,309,486 B1 | 12/2007 | Zamoyski | |
| 9,150,663 B2 * | 10/2015 | Labrijn | C07K 16/1063 |
| 2003/0118583 A1 | 6/2003 | Emery et al. | |
| 2009/0203538 A1 * | 8/2009 | Sugioka et al. | 506/9 |
| 2011/0158988 A1 * | 6/2011 | Uhlen et al. | 424/133.1 |
| 2013/0189271 A1 | 7/2013 | De Goeij et al. | |
| 2014/0170148 A1 * | 6/2014 | De Goeij | A61K 47/48676 424/136.1 |
| 2014/0170149 A1 * | 6/2014 | Neijssen | A61K 47/48484 424/136.1 |

FOREIGN PATENT DOCUMENTS

| | | |
|---|---|---|
| CN | 101633695 B | 1/2010 |
| CN | 101721700 A | 6/2010 |
| EP | 1980626 A1 | 10/2008 |
| EP | 2078732 A1 | 7/2009 |
| WO | 89/06692 A1 | 7/1989 |
| WO | 97/35885 A1 | 10/1997 |
| WO | 98/17797 A1 | 4/1998 |
| WO | 99/31140 A1 | 6/1999 |
| WO | 99/44645 A1 | 9/1999 |
| WO | 99/48527 A1 | 9/1999 |
| WO | 99/55367 A1 | 11/1999 |
| WO | 00/69460 A1 | 11/2000 |
| WO | 01/00238 A1 | 1/2001 |
| WO | 01/00244 A2 | 1/2001 |
| WO | 01/00245 A2 | 1/2001 |
| WO | 01/09187 A2 | 2/2001 |
| WO | 01/89566 A1 | 11/2001 |
| WO | 03/101491 A1 | 12/2003 |
| WO | 2004/032960 A1 | 4/2004 |
| WO | 2005/034733 A2 | 4/2005 |
| WO | 2005/118635 A2 | 12/2005 |

(Continued)

OTHER PUBLICATIONS

Rudikoff et al. (Proceedings of the National Academy of Sciences, 1982, 79:1979-1983).*

(Continued)

*Primary Examiner* — Julie Wu
(74) *Attorney, Agent, or Firm* — Nelson Mullins Riley & Scarborough LLP; Jane E. Remillard, Esq.; Christopher L. Frank

(57) ABSTRACT

Isolated monoclonal antibodies which bind to human epidermal growth factor receptor 2 (HER2), and related antibody-based compositions and molecules, are disclosed. Pharmaceutical compositions comprising the antibodies and therapeutic and diagnostic methods for using the antibodies are also disclosed.

43 Claims, 11 Drawing Sheets

(56) References Cited

FOREIGN PATENT DOCUMENTS

| WO | 2006/033700 A2 | 3/2006 |
|---|---|---|
| WO | 2006/063042 A2 | 6/2006 |
| WO | 2006/087637 A2 | 8/2006 |
| WO | 2006/091693 A2 | 8/2006 |
| WO | 2006/113643 A2 | 10/2006 |
| WO | 2006/116107 A2 | 11/2006 |
| WO | 2007059782 A1 | 5/2007 |
| WO | 2007/084181 A2 | 7/2007 |
| WO | WO 2008007648 A1 * | 1/2008 |
| WO | 2008/019290 A2 | 2/2008 |
| WO | 2008/022746 A1 | 2/2008 |
| WO | 2008/031531 A1 | 3/2008 |
| WO | 2008/088861 A2 | 7/2008 |
| WO | 2008/097229 A1 | 8/2008 |
| WO | 2008/109440 A2 | 9/2008 |
| WO | 2008/119493 A1 | 10/2008 |
| WO | 2008/127710 A2 | 10/2008 |
| WO | 2008/130910 A1 | 10/2008 |
| WO | 2008/148546 A2 | 12/2008 |
| WO | 2008/150485 A2 | 12/2008 |
| WO | 2008/154249 A2 | 12/2008 |
| WO | 2009/030239 A1 | 3/2009 |
| WO | 2009026681 A1 | 3/2009 |
| WO | 2009/055074 A2 | 4/2009 |
| WO | 2009/068625 A2 | 6/2009 |
| WO | 2009/073524 A2 | 6/2009 |
| WO | 2009/099829 A1 | 8/2009 |
| WO | 2009/100110 A1 | 8/2009 |
| WO | 2009/105230 A2 | 8/2009 |
| WO | 2009/151356 A1 | 12/2009 |
| WO | 2009/154651 A1 | 12/2009 |
| WO | 2010/027981 A1 | 3/2010 |
| WO | 2010/070117 A1 | 6/2010 |

OTHER PUBLICATIONS

MacCallum et al. (Journal of Molecular Biology, 1996, 262:732-745).*
De Pascalis et al. (Journal of Immunology, 2002, 169:3076-3084).*
Casset et al. (Biochemical and Biophysical Research Communications, 2003, 307:198-205).*
Vajdos et al. (Journal of Molecular Biology, 2002, 320:415-428).*
Holm et al. (Molecular Immunology, 2007:1075-1084).*
Chen et al. (Journal of Molecular Biology, 1999, 293:865-881).*
Wu et al. (Journal of Molecular Biology, 1999, 294:151-162).*
Berglund et al, 2008, Protein Science, 17:606-613.*
Rockberg et al (Molecular Oncology, 2009, 3:238-247).*
Lerdrup et al. (Molecular Biology of the Cell, 2007, 18:3656-3666).*
R&D Systems (Human ErbB2/Her2 Antibody__AF1129).*
George et al. (Circulation, 1998; 97: 900-906).*
Sangrajrang et al. (Cancer Detection and Prevention, 2003, 27:182-186).*
Hudis Clifford A., "Drug therapy: Trastuzumab—Mechanism of action and use in clinical practice," New England Journal of Medicine, vol. 357, No. 1, p. 39-51, Jul. 5, 2007.
Langdon S P et al., "Pertuzumab—Humanized anti-HER2 monoclonal antibody HER dimerization inhibitor oncolytic," Drugs of the Future, Prous Science, vol. 33, No. 2, Feb. 1, 2008, pp. 123-130.
Rudikoff S et al., "Single amino acid substitution altering antigen-binding specificity," Proceedings of the National Academy of Sciences, National Academy of Sciences, vol. 79, Mar. 2, 1982, pp. 1979-1983.
Maccallum R M et al., "Antibody-antigen interactions: Contact analysis and binding site topography," Journal of Molecular Biology, vol. 262, No. 5, Jan. 1, 1996, pp. 732-745.
Nahta, Rita et al., "Mechanisms of Disease: Understanding Resistance to HER2-targeted therapy in human breast cancer," Nat Clin Pract Oncol 3(5): 269-280 (2006).
Rockberg J et al., "Discovery of epitopes for targeting the human epidermal growth factor receptor 2 (HER2) with antibodies," Molecular Oncology, vol. 3, No. 3, Jun. 1, 2009, p. 238-247.
Montgomery R Bruce et al., "Endogenous anti-HER2 antibodies block HER2 phosphorylation and signaling through extracellular signal-regulated kinase," Cancer Research, American Association for Cancer Research, vol. 65, No. 2, Jan. 15, 2005, p. 650-656.
Jasinska, Joanna et al., "Inhibition of tumor cell growth by antibodies induced after vaccination with peptides derived from the extracellular domain of Her-2/neu," International Journal of Cancer, vol. 107, No. 6, Dec. 20, 2003, p. 976-983.
Hu, Siyi et al., "Epitope mapping and structural analysis of an anti-ErbB2 antibody A21: Molecular basis for tumor inhibitory mechanism," Proteins: Structure, Function and Bioinformatics, vol. 70, No. 3, Feb. 15, 2008, p. 938-949.
Database Geneseq [online], Feb. 23, 2006, "Antibody 28F10 light chain variable region SEQ ID No. 8".
Database Geneseq [online], Jan. 11, 2007, "Human anti-IL8 monoclonal antibody mAb 809 Vk".
Database Geneseq [online], Mar. 20, 2008, "Human HER2 specific antibody VL Seq ID No. 639".
Database Geneseq [online], Aug. 6, 2009, "Human anti-RG-1 Monoclonal antibody 34E1 VL, Seq ID No. 16".
Boyer CM, et al., "Relative cytotoxic activity of immunotoxins reactive with different epitopes on the extracellular domain of the c-erbB-2 (HER-2/neu) gene product," p. 185. Int J Cancer 1999;82:525-31.
Klapper LN, et al., "A subclass of tumor-inhibitory monoclonal antibodies to ErbB-2/HER2 blocks crosstalk with growth factor receptors," Oncogene 1997;14:2099-2109.
Guillemard V, et al., "HER2-mediated internalization of a targeted prodrug cytotoxic conjugate is dependent on the valency of the targeting ligand," DNA Cell Biol 2005;24:350-8.
Ben-Kasus T, et al., "Persistent elimination of ErbB-2/HER2-overexpressing tumors using combinations of monoclonal antibodies: relevance of receptor endocytosis," Proc Natl Acad Sci U S A 2009; 106:3294-9.
Harwerth IM, et al., "Monoclonal antibodies directed to the erbB-2 receptor inhibit in vivo tumour cell growth," Br J Cancer 1993; 68:1140-5.
Agus DB., et al., "Targeting ligand-activated ErbB2 signaling inhibits breast and prostate tumor growth," Cancer Cell, 2002;2:127-137.
Andrechek et al., Amplification of the neu/erbB-2 oncogene in a mouse model of mammary tumorigenesis, Proc Natl Acad Sci USA 2000; 97:3444-3449.
Baselga et al., "Phase II Trial of Pertuzumab and Trastuzumab in Patients With Human Epidermal Growth Factor Receptor 2-Positive Metastatic Breast Cancer That Progressed During Prior Trastuzumab Therapy," J Clin Oncol 2010;28:1138-1144.
Baulida et al., "Cell Biology and Metabolism: All ErbB Receptors Other Than the Epidermal Growth Factor Receptor are Endocytosis Impaired," J Biol Chem 1996;271:5251-5257.
Bolt, S. et al. "The generation of a humanized, non-mitogenic CD3 monoclonal antibody which retains in vitro immunosuppressive properties," Eur J Immunol 1993, 23:403-411.
Burris et al, "Phase II Study of the Antibody Drug Conjugate Trastuzumab-DM1 for the Treatment of Human Epidermal Growth Factor Receptor 2 (HER2)-Positive Breast Cancer After Prior HER2-Directed Therapy," 2011, J Clin Oncol 29: 398-405.
Cho et al., "Structure of the extracellular region of HER2 alone and in complex with the Herceptin Fab," Nature 2003;421:756-760.
Dinh et al., "Traztuzumab for Early Breast Cancer: Current Status and Future Directions," Clin Adv Hematol Oncol 2007;5:707-717).
Franklin et al., "Insights into ErbB signaling from the structure of the ErbB2-pertuzumab complex," Cancer Cell 2004;5:317-328.
Garcia de Palazzo et al., Immunohistochemical detection of c-erbB-2 expression by neoplastic human tissue using monospecific and bispecific monoclonal antibodies,: Int J Biol Markers 1993;8:233-239.
Graus-Porta et al., "ErbB-2, the preferred heterodimerization partner of all ErbB receptors, is a mediator of lateral signaling," Embo J 1997; 16: 1647-1655.

(56) References Cited

OTHER PUBLICATIONS

Heynes, et al., PI3K Inhibition Overcomes Trastuzumab Resistance: Blockade of ErbB2/ErbB3 is not Always Enough, Cancer Cell, 2009;15(5):353-355.

Huang et al., "A pan-HER approach for cancer therapy: background, current status and future development," Expert Opin Biol Ther 2009;9:97-110.

Hughes et al., "Pertuzumab increases epidermal growth factor receptor down-regulation by counteracting epidermal growth factor receptor-ErbB2 heterodimerization," Mol Cancer Ther 2009;8:1885-1892.

Jones et al., "Evolving novel anti-HER2 strategies," Lancet Oncol 2009;10:1179-1187.

Juntilla TT. et al., "Ligand-Independent HER2/HER3/PI3K Complex is Disrupted by Trastuzumab and is Effectively Inhibited by the PI3K Inhibitor GDC-0941," Cancer Cell 2009; 15: 429-440.

Kapitanovic et al., "The Expression of p185HER-2/neu Correlates With the Stage of Disease and Survival in Colorectal Cancer," Gastroenterology 1997;112:1103-1113.

Kiewe et al., "Phase I Trial of the Trifunctional Anti-HER2 X Anti-CD3 Antibody Ertumaxomab in Metastatic Breast Cancer," Clin Cancer Res 2006;12:3085-3091.

Klein, C. et al., "Epitope interactions of monoclonal antibodies targeting CD20 and their relationship to functional properties," mAbs, vol. 5, Issue 1, Jan.-Feb. 2013, 22-33.

Krop et al.,"Phase I Study of Trastuzumab-DM1, an HER2 Antibody-Drug Conjugate, Given Every 3 Weeks to Patients With HER2-Positive Metastatic Breast Cancer," J Clin Oncol. 2010, 28(16), 2698-2704.

Larsen SS., et al., "Acquired antiestrogen resistance in MCF-7 human breast cancer sublines is not accomplished by altered expression of receptors in the ErbB-family," Breast Cancer Res Treat 1999;58:41-56.

Lewis Phillips et al., "Targeting HER2-Positive Breast Cancer with Trastuzumab-DM1, an Antibody-Cytotoxic Drug Conjugate," Cancer Res 2008;68:9280-9290.

Muller and Kontermann, "Cloning and sequencing of the cDNA encoding the human homologue of the murine immunoglobulin-associated protein B29," BioDrugs 2010;24:89-98.

Nahta and Esteva, "Trastuzumab: triumphs and tribulations," Oncogene 2007; 26:3637-3643.

Oshima et al., "c-erbB-2 oncoprotein in gastric carcinoma: correlation with clinical stage and prognosis," Int J Biol Markers 2001; 16: 250-254.

Osman et al., "Serum Levels of SHED HER2/neu Protein in Men With Prostate Cancer Correlate With Disease Progression," J Urol 2005;174:2174-2177.

Parren et al., "Induction of T-cell proliferation by recombinant mouse and chimeric mouse/human anti-CD3 monoclonal," Res Immunol. 1991, 142(9):749-763.

Pedersen et al., "Expression of Epidermal Growth Factor Receptor or ErbB3 Facilitates Geldanamycin-Induced Down-Regulation of ErbB2," Mol Cancer Res 2009;7:275-284.

Perez et al., Efficacy and Safety of Trastuzumab-DM1 Stuzumab-DM1 Versus Trastuzumab Plus Docetaxel in HER2-Positive Metastatic Breast Cancer Patients With No Prior Chemotherapy for Metastatic Disease: Preliminary Results of a Randomized, Multi-center, Open-Label Phase 2 Study (TDM4450G), Abstract LBA3, European Society for Medical Oncology Meeting 2010, 1-12.

Reese et al., HER-2/neu Signal Transduction in Human Breast and Ovarian Cancer, Stem Cells 1997;15:1-8.

Riese and Stern, "Specificity within the EGF family/ErbB receptor family signaling network," Bioessays 1998; 20:41-48.

Ross et al., "The HER-2/neu Gene and Protein in Breast Cancer 2003: Biomarker and Target of Therapy," Oncologist 2003; 8:307-325.

Routledge et al., "A humanized monovalent CD3 antibody which can activate homologous complement," Eur J Immunol. 1991, 21(11):2717-2725.

Schmitz et al., "Interaction of antibodies with ErbB receptor extracellular regions," Exp Cell Res 2009;315:659-670.

Slamon et al., "Human Breast Cancer: Correlation of Relapse and Survival with Amplification; of the HER-2/neu Oncogene," Science 1987; 235:177-182.

Tao et al., "All EGF(ErbB) receptors have preformed homo- and heterodimeric structures in living cells," J Cell Sci 2008;121:3207-3217.

Turken et al., "Prevalence and Prognostic Value of c-erbB2 expression in non-small cell lung cancer (NSCLC)," Neoplasma 2003;50: 257-261.

Wehrman et al., "A system for quantifying dynamic protein interactions defines a role for Herceptin in modulating ErbB2 interactions," Proc Natl Acad Sci USA 2006;103:19063-19068.

U.S. Appl. No. 13/700,341, filed Mar. 14, 2013, Bart De Goeij.
U.S. Appl. No. 13/700,341, Mar. 19, 2015.
U.S. Appl. No. 13/700,341, Sep. 18, 2014.
U.S. Appl. No. 14/112,848, filed Feb. 7, 2014, Bart De Goeij.
U.S. Appl. No. 14/112,859, filed Feb. 12, 2014, Joost J. Neijssen.
U.S. Appl. No. 14/112,848, Sep. 24, 2015.
U.S. Appl. No. 14/112,848, Jan. 15, 2015.
U.S. Appl. No. 14/112,859, Sep. 24, 2015.
U.S. Appl. No. 14/112,859, Feb. 13, 2015.
U.S. Appl. No. 13/700,341, Oct. 7, 2015.
U.S. Appl. No. 13/700,341, Mar. 21, 2016.
U.S. Appl. No. 14/112,848, May 20, 2016.
U.S. Appl. No. 14/112,859, May 20, 2016.
U.S. Appl. No. 13/700,341, Oct. 14, 2016.

* cited by examiner

Figure 1A

IgHV5-51-1 / IGHJ6-02 – VH alignment

| SEQ ID NO | | |
|---|---|---|
| 86 | IgHV5-51-1 | EVQLVQSGAEVKKPGESLKISCKGSGYSFTSYWIGWVRQMPGKGLEWMGIIYPGDSTRYSPSFQ |
| 1 | TH1014-005 | EVQLVQSGAEVKKPGESLKISCKGSGYSFTSYWIGWVRQMPGKGLEWMGIIYPGDSTRYSPSFQ |
| 22 | TH1014-060 | EVQLVQSGAEVKKPGESLKISCKGSGYSFTSYWIGWVRQMPGKGLEWMGIIYPGDSTRYSPSFQ |
| 29 | TH1014-106 | EVQLVQSGAEVKKPGESLKISCKGSGYSFTSYWIGWVRQMPGKGLEWMGIIYPGDSTRYSPSFQ |
| 43 | VH1014-041 | EVQLVQSGAEVKKPGESLKISCKGSGYSFTSYWIGWVRQMPGKGLEWMGIIYPGDSTRYSPSFQ |
| 45 | VH1014-150 | EVQLVQSGAEVKKPGESLKISCKGSGYSFTSYWIGWVRQMPGKGLEWMGIIYPGDSTRYSPSFQ |
| 47 | VH1014-067 | EVQLVQSGAEVKKPGESLKISCKGSGYSFTSYWIGWVRQMPGKGLEWMGIIYPGDSTRYSPSFQ |
| 49 | VH1014-072 | EVQLVQSGAEVKKPGESLKISCKGSGYSFTSYWIGWVRQMPGKGLEWMGIIYPGDSTRYSPSFQ |
| 51 | VH1014-163 | EVQLVQSGAEVKKPGESLKISCKGSGYSFTSYWIGWVRQMPGKGLEWMGIIYPGDSTRYSPSFQ |
| 53 | VH1014-093 | EVQLVQSGAEVKKPGESLKISCKGSGYSFTSYWIGWVRQMPGKGLEWMGIIPGDSDTRYSPSFQ |
| 55 | VH1014-044 | EVQLVQSGAEVKKPGESLKISCKGSGYSFTSYWIGWVRQMPGKGLEWMGIIPGDSDTRYSPSFQ |
| 87 | Consensus | EVQLVQSGAEVKKPGESLKISCKGSGYSFTSYWIGWVRQMPGKGLEWMGIIYPGDSTRYSPSFQ |

| 86 | IgHV5-51-1 | GQVTISADKSISTAYLQWSSLKASDTAMYYCAR------------GMDVWGQGTTVTVSS |
| 1 | TH1014-005 | GQVTISADKSISTAYLQWSSLKASDTAMYYCAR-----YYYYGMDVWGQGTTVTVSS |
| 22 | TH1014-060 | GQVTISADKSISTAYLQWSSLKASDTAMYYCAR-----YYYYGMDVWGQGTTVTVSS |
| 29 | TH1014-106 | GQVTISADKSISTAYLQWSSLKASDTAMYYCAR-----YYYYGMDVWGQGTTVTVSS |
| 43 | VH1014-041 | GQVTISADKSISTAYLQWSSLKASDTAMYYCAR-----YYYYGMDVWGQGTTVTVSS |
| 45 | VH1014-150 | GQVTISADKSISTAYLQWSSLKASDTAMYYCAR-----YYYYGMDVWGQGTTVTVSS |
| 47 | VH1014-067 | GQVTISADKSISTAYLQWSSLKASDTAMYYCAR-----YYYYGMDVWGQGTTVTVSS |
| 49 | VH1014-072 | GQVTISADKSISTAYLQWSSLKASDTAMYYCAR-----YYYYGMDVWGQGTTVTVSS |
| 51 | VH1014-163 | GQVTISADKSISTAYLQWSSLKASDTAMYYCAR-----YYYYGMDVWGQGTTVTVSS |
| 53 | VH1014-093 | GQVTISADKSISTAYLQWSSLKASDTAMYYCAR-----YYYYGMDVWGQGTTVTVSS |
| 55 | VH1014-044 | GQVTISADKSISTAYLQWSSLKASDTAMYYCAR-----YYYYGMDVWGQGTTVTVSS |
| 87 | Consensus | GQVTISADKSISTAYLQWSSLKASDTAMYYCAR-----YYYYGMDVWGQGTTVTVSS |

Figure 1B

| SEQ ID NO | IgHV3-23-1 / IGHJ4-02 – VH alignment |
|---|---|
| 88 | IgHV3-23-1  EVQLLESGGGLVQPGGSLRLSCAASGFTFSSYAMSWVRQAPGKGLEWVSAISGSGGSTYYADSVKG |
| 8 | TH1014-006  EVQLLESGGGLVQPGGSLRLSCAASGFTFSSYSYAMWVRQAPGKGLEWVSIIRGGSTYYADSVKG |
| 89 | Consensus   EVQLLESGGGLVQPGGSLRLSCAASGFTFSSYSYAMWVRQAPGKGLEWVSIIRGGSTYYADSVKG |
| 88 | IgHV3-23-1  RFTISRDNSKNTLYLQMNSLRAEDTAVYYCAK------YFDYWGQGTLVTVSS |
| 8 | TH1014-006  RFTISRDNSKNTLYLQMNSLRAEDTAVYYCAKARIWGPFDYWGQGTLVTVSS |
| 89 | Consensus   RFTISRDNSKNTLYLQMNSLRAEDTAVYYCAKARIWGPFDYWGQGTLVTVSS |

Figure 1C

| SEQ ID NO | IgHV1-18-1 / IGHJ4-02 – VH alignment |
|---|---|
| 90 | IgHV1-18-1  QVQLVQSGAEVKKPGASVKVSCKASGYTFTSYGISWVRQAPGQGLEWMGWISAYNGNTNYAQKLQG |
| 15 | TH1014-059  QVQLVQSGAEVKKPGASVKVCKASGYTFTYGISWVRQAPGQGLEWMGWISAYNGITYAQKLQG |
| 91 | Consensus   QVQLVQSGAEVKKPGASVKVCKASGYTFTYGISWVRQAPGQGLEWMGWISAYNGITYAQKLQG |
| 90 | IgHV1-18-1  RVTMTTDTSTSTAYMELRSLRSDDTAVYYCAR------YFDYWGQGTLVTVSS |
| 15 | TH1014-059  RVTMTTDTSTSTAYMELRSLRSDDTAVYYCARSPLLMFEELYFDYWGQGTLVTVSS |
| 91 | Consensus   RVTMTTDTSTSTAYMELRSLRSDDTAVYYCARSPLLMFEELYFDYWGQGTLVTVSS |

Figure 1D

| SEQ ID NO | IgHV1-69-4 / IGHJ4-02 – VH alignment |
|---|---|
| 92 | IgHV1-69-4  QVQLVQSGAEVKKPGSSVKVSCKASGGTFSSYAISWVRQAPGQGLEWMGRIIPILGIANYAQKFQG |
| 36 | TH1014-111  QVQLVQSGAEVKKPGSSVKVSCKASGGTFSSYISWVRQAPGGLEWMGRIIPILGIANYAQKFQG |
| 93 | Consensus   QVQLVQSGAEVKKPGSSVKVSCKASGGTFSSYISWVRQAPGGLEWMGRIIPILGIANYAQKFQG |
| 92 | IgHV1-69-4  RVTITADKSTSTAYMELSSLRSEDTAVYYCAR------YFDYWGQGTLVTVSS |
| 36 | TH1014-111  RVTITADKSTTAYMELSSLRSEDTAVYYCARDQEYSSYWGQGTLVTVSS |
| 93 | Consensus   RVTITADKSTTAYMELSSLRSEDTAVYYCARDQEYSSYWGQGTLVTVSS |

Figure 2A

IgKV3-20-01 / IGKJ4-01 – VL alignment

| SEQ ID NO | | |
|---|---|---|
| 94 | IgKV3-20-01 | EIVLTQSPGTLSLSPGERATLSCRASQSVSSSYLAWYQQKPGQAPRLLIYGASSRATGIPDRFSGS |
| 5 | VL1014-005 | EIVLTQSPGTLSLSPGERATLSCRASQSVSSSYLAWYQQKPGQAPRLLIYGASSRATGIPDRFSGS |
| 19 | VL1014-059 | EIVLTQSPGTLSLSPGERATLSCRASQSVSSSYLAWYQQKPGQAPRLLIYGASSRATGIPDRFSGS |
| 26 | VL1014-060 | EIVLTQSPGTLSLSPGERATLSCRASQSVSSSYLAWYQQKPGQAPRLLIYGASSRATGIPDRFSGS |
| 33 | VL1014-106 | EIVLTQSPGTLSLSPGERATLSCRASQSVSSSYLAWYQQKPGQAPRLLIYGASSRATGIPDRFSGS |
| 40 | VL1014-111 | EIVLTQSPGTLSLSPGERATLSCRASQSVSSSYLAWYQQKPGQAPRLLIYGASSRATGIPDRFSGS |
| 44 | VL1014-041 | EIVLTQSPGTLSLSPGERATLSCRASQSVSSSYLAWYQQKPGQAPRLLIYGASSRATGIPDRFSGS |
| 46 | VL1014-150 | EIVLTQSPGTLSLSPGERATLSCRASQSVSSSYLAWYQQKPGQAPRLLIYGASSRATGIPDRFSGS |
| 48 | VL1014-067 | EIVLTQSPGTLSLSPGERATLSCRASQSVSSSYLAWYQQKPGQAPRLLIYGASSRATGIPDRFSGS |
| 50 | VL1014-072 | EIVLTQSPGTLSLSPGERATLSCRASQSVSSSYLAWYQQKPGQAPRLLIYGASSRATGIPDRFSGS |
| 52 | VL1014-163 | EIVLTQSPGTLSLSPGERATLSCRASQSVSSSYLAWYQQKPGQAPRLLIYGASSRATGIPDRFSGS |
| 54 | VL1014-093 | EIVLTQSPGTLSLSPGERATLSCRASQSVSSSYLAWYQQKPGQAPRLLIYGASSRATGIPDRFSGS |
| 56 | VL1014-044 | EIVLTQSPGTLSLSPGERATLSCRASQSVSSSYLAWYQQKPGQAPRLLIYGASSRATGIPDRFSGS |
| 95 | Consensus | EIVLTQSPGTLSLSPGERATLSCRASQSVSSSYLAWYQQKPGQAPRLLIYGASSRATGIPDRFSGS |
| 94 | IgKV3-20-01 | GSGTDFTLTISRLEPEDFAVYYCQQYGSSP-LTFGGGTKVEIK |
| 5 | VL1014-005 | GSGTDFTLTISRLEPEDFAVYYCQQYGSS--LTFGGGTKVEIK |
| 19 | VL1014-059 | GSGTDFTLTISRLEPEDFAVYYCQQYGSS-ITFGPGTKVEIK |
| 26 | VL1014-060 | GSGTDFTLTISRLEPEDFAVYYCQQYGSSP-ITFGQGTKVEIK |
| 33 | VL1014-106 | GSGTDFTLTISRLEPEDFAVYYCQQYGSSP-FTFGPGKVDIK |
| 40 | VL1014-111 | GSGTDFTLTISRLEPEDFAVYYCQQYGSSF-TFGPGTKVDIK |
| 44 | VL1014-041 | GSGTDFTLTISRLEPEDFAVYYCQQYGSS-LTFGGGTKVEIK |
| 46 | VL1014-150 | GSGTDFTLTISRLEPEDFAVYYCQQYGSS-LTFGGGTKVEIK |
| 48 | VL1014-067 | GSGTDFTLTISRLEPEDFAVYYCQQYGSS-LTFGGGTKVEIK |
| 50 | VL1014-072 | GSGTDFTLTISRLEPEDFAVYYCQQYGSS-LTFGGGTKVEIK |
| 52 | VL1014-163 | GSGTDFTLTISRLEPEDFAVYYCQQYGSS-LTFGGGTKVEIK |
| 54 | VL1014-093 | GSGTDFTLTISRLEPEDFAVYYCQQYGSS-LTFGGGTKVEIK |
| 56 | VL1014-044 | GSGTDFTLTISRLEPEDFAVYYCQQYGSS-LTFGGGTKVEIK |
| 95 | Consensus | GSGTDFTLTISRLEPEDFAVYYCQQYGSS-TFGGGTKVEIK |

Figure 2B

IgKV3-11-01 / IGKJ4-01 – VL alignment

| SEQ ID NO | | |
|---|---|---|
| 96 | IgKV3-11-01 | EIVLTQSPATLSLSPGERATLSCRASQSVSSYLAWYQQKPGQAPRLLIYDASNRATGIPARFSGS |
| 96 | VL1014-006 | EIVLTQSPATLSLSPGERATLSCRASQSVSSYLAWYQQKPGQAPRLLIYDASNRATGIPARFSGS |
| 96 | Consensus | EIVLTQSPATLSLSPGERATLSCRASQSVSSYLAWYQQKPGQAPRLLIYDASNRATGIPARFSGS |
| 96 | IgKV3-11-01 | GSGTDFTLTISSLEPEDFAVYYCQQRSNWPPLTFGGGTKVEIK |
| 96 | VL1014-006 | GSGTDFTLTISSLEPEDFAVYYCQQRSNWPPLTFGGGTKVEIK |
| 96 | Consensus | GSGTDFTLTISSLEPEDFAVYYCQQRSNWPPLTFGGGTKVEIK |

MONOCLONAL ANTIBODIES AGAINST HER2 EPITOPE

RELATED APPLICATIONS

This application is a 35 U.S.C. 371 national stage filing of International Application No. PCT/EP2011/058772 filed May 27, 2011, which claims priority to 61/349,182 filed May 27, 2010; and PA 2010 00468 filed May 27, 2010. The contents of the aforementioned applications are hereby incorporated by reference.

SEQUENCE LISTING

The instant application contains a Sequence Listing which has been submitted via EFS-Web and is hereby incorporated by reference in its entirety. Said ASCII copy, created on Mar. 22, 2017, is named GMI_132USRCE_Sequence_Listing.txt and is 56,726 bytes in size.

FIELD OF THE INVENTION

The present invention relates to monoclonal antibodies directed to human epidermal growth factor receptor 2 (HER2) and to uses of such antibodies, in particular their use in the treatment of cancer.

BACKGROUND OF THE INVENTION

HER2 is a 185-kDa cell surface receptor tyrosine kinase and member of the epidermal growth factor receptor (EGFR) family that comprises four distinct receptors: EGFR/ErbB-1, HER2/ErbB-2, HER3/ErbB-3, and HER4/ErbB-4. Both homo- and heterodimers are formed by the four members of the EGFR family, with HER2 being the preferred and most potent dimerization partner for other ErbB receptors (Graus-Porta et al., Embo J 1997; 16:1647-1655; Tao et al., J Cell Sci 2008; 121:3207-3217). HER2 can be activated by overexpression or by heterodimerization with other ErbBs that can be activated by ligand binding (Riese and Stern, Bioessays 1998; 20:41-48). For HER2, no ligand has been identified. HER2 activation leads to receptor phosphorylation, which triggers a cascade of downstream signals through multiple signaling pathways, such as MAPK, phosphoinositol 3-kinase/AKT, JAK/STAT and PKC, which ultimately results in the regulation of multiple cellular functions, such as growth, survival and differentiation (Huang et al., Expert Opin Biol Ther 2009; 9:97-110).

Much of the attention on HER2 in tumors has been focused on its role in breast cancer, in which HER2 overexpression is reported in approximately 20% of the cases and is correlated with poor prognosis (Reese et al., Stem Cells 1997; 15:1-8; Andrechek et al., Proc Natl Acad Sci USA 2000; 97:3444-3449; and Slamon et al., Science 1987; 235:177-182). Besides breast cancer, HER2 expression has also been associated with other human carcinoma types, including prostate cancer, non-small cell lung cancer, bladder cancer, ovarian cancer, gastric cancer, colon cancer, esophageal cancer and squamous cell carcinoma of the head & neck (Garcia de Palazzo et al., Int J Biol Markers 1993; 8:233-239; Ross et al., Oncologist 2003; 8:307-325; Osman et al., J Urol 2005; 174:2174-2177; Kapitanovic et al., Gastroenterology 1997; 112:1103-1113; Turken et al., Neoplasma 2003; 50:257-261; and Oshima et al., Int 3 Biol Markers 2001; 16:250-254).

Trastuzumab (Herceptin®) is a recombinant, humanized monoclonal antibody directed against domain IV of the HER2 protein, thereby blocking ligand-independent HER2 homodimerization, and to a lesser extend heterodimerization of HER2 with other family members in cells with high HER2 overexpression (Cho et al., Nature 2003; 421:756-760 and Wehrman et al., Proc Natl Acad Sci USA 2006; 103: 19063-19068). In cells with modest HER2 expressing levels, trastuzumab was found to inhibit the formation of HER2/EGFR heterodimers (Wehrman et al., (2006), supra; Schmitz et al., Exp Cell Res 2009; 315:659-670). Trastuzumab mediates antibody-dependent cellular cytotoxicity (ADCC) and prevents ectodomain shedding, which would otherwise result in the formation of a truncated constitutively active protein in HER2 overexpressing cells. Also inhibition of both in vitro and in vivo proliferation of tumor cells expressing high levels of HER2 has been reported for trastuzumab (reviewed in Nahta and Esteva, Oncogene 2007; 26:3637-3643). Herceptin® has been approved both for first-line and adjuvant treatment of HER2 overexpressing metastatic breast cancer, either in combination with chemotherapy, or as a single agent following one or more chemotherapy regimens. Trastuzumab has been found to be effective only in 20-50% of HER2 overexpressing breast tumor patients and many of the initial responders show relapse after a few months (Dinh et al., Clin Adv Hematol Oncol 2007; 5:707-717).

Pertuzumab (Omnitarg™) is another humanized monoclonal antibody directed against domain II of the HER2 protein, resulting in inhibition of ligand-induced heterodimerization (i.e., HER2 dimerizing with another member of the ErbB family to which a ligand has bound); a mechanism reported to not strictly require high HER2 expression levels (Franklin et al., Cancer Cell 2004; 5:317-328.). Although pertuzumab also mediates ADCC, the main mechanism of action of pertuzumab relies on its dimerization blockade (Hughes et al., Mol Cancer Ther 2009; 8:1885-1892). Moreover, pertuzumab was found to enhance EGFR internalization and downregulation by inhibiting the formation of EGFR/HER2 heterodimers, which otherwise tethers EGFR at the plasma membrane (Hughes et al., 2009, supra). This correlates with the observation that EGFR homodimers internalize more efficient than EGFR/HER2 dimers (Pedersen et al., Mol Cancer Res 2009; 7:275-284. The complementary mechanisms of action of pertuzumab and trastuzumab reportedly results in enhanced anti-tumor effects and efficacy when combined in patients who progressed during prior trastuzumab therapy (Baselga et al., J Clin Oncol 2010; 28:1138-1144), and a phase III trial to evaluate this antibody combination together with Docetaxel in previously untreated HER2-positive metastatic breast cancer is underway.

An alternative approach to improve targeted antibody therapy is by delivering cytotoxic cells or drugs specifically to the antigen-expressing cancer cells. For example, the so-called trifunctional antibodies are bispecific antibodies, targeting with one arm the antigen on the tumor cell and with the other arm for instance CD3 on T cells. Upon binding, a complex of T cells, tumor cells and effector cells that bind Fc is formed, leading to killing of the tumor cells (Muller and Kontermann, BioDrugs 2010; 24:89-98.). Ertumaxomab is one such trifunctional antibody against HER2, which induces cytotoxicity in cell lines with low HER2 expression and which is in Phase II clinical development in metastatic breast cancer (Jones et al., Lancet Oncol 2009; 10:1179-1187 and Kiewe et al., Clin Cancer Res 2006; 12:3085-3091).

A HER2 antibody drug conjugate (ADC) is currently in clinical development. T-DM1 consists of trastuzumab conjugated to the fungal toxin maytansine. In Phase II trials, responses in a heavily pretreated patient cohort including prior trastuzumab and/or lapatinib therapy were reported (Krop et al., J Clin Oncol. 2010 (published on-line ahead of print) and Lewis Phillips et al., Cancer Res 2008; 68:9280-9290). A Phase III trial to evaluate T-DM1 efficacy and safety versus capecitabine+lapatinib in patients with HER2-positive locally advanced or metastatic breast cancer who received prior trastuzumab therapy is ongoing.

While many factors are involved in selecting a suitable antibody for HER2 targeted therapy, it is typically an advantage for an ADC approach if the HER2-antibody complex efficiently internalizes upon antibody binding. Studies on murine HER2 antibodies have shown that certain combinations of antibodies instigate HER2 endocytosis (Ben-Kasus et al., PNAS 2009; 106:3294-9). Human HER2 antibodies F5 and C1 have been reported to internalize relatively rapidly on their own and to bind the same epitope (WO 99/55367 and WO 2006/116107). As compared to EGFR, however, internalization of HER2 is impaired. Indeed, EGFR homodimers internalize much more efficiently than HER2 homodimers (Dinh et al., Clin Adv Hematol Oncol 2007; 5:707-717). EGFR, and also HER3, can increase endocytosis of HER2 by the formation of EGFR/HER2 and HER3/HER2 heterodimers, respectively (Baulida et al., J Biol Chem 1996; 271:5251-5257; Pedersen N M, et al., Mol Cancer Res 2009; 7:275-84).

The complex mechanisms regulating the function of HER2 warrant further research on new and optimized therapeutic strategies against this proto-oncogene. Accordingly, there remains a need for effective and safe products for treating HER2-related diseases, such as cancer.

SUMMARY OF THE INVENTION

It is an object of the present invention to provide novel highly specific and effective monoclonal HER2 antibodies for medical use. The antibodies of the invention exhibit HER2 binding characteristics that differ from antibodies described in the art. Particularly, the antibodies of the invention bind to a different segment of HER2, in that they cross-block each other but not trastuzumab, pertuzumab or F5/C1 from binding to HER2. Further, as opposed to the known antibodies, the antibodies of the invention can internalize efficiently into HER2-expressing cells without promoting cell proliferation.

In preferred embodiments, the antibodies of the invention are fully human, bind to novel epitopes and/or have other favorable properties for therapeutic use in human patients. Exemplary properties include, but are not limited to, favorable binding characteristics to cancer cells expressing human HER2 at high or low levels, specific binding to rhesus epithelial cells expressing a HER2 ortholog, efficient internalization upon binding to HER2, high capacity for killing cancer cells expressing high or low levels of HER2 when administered as an antibody drug conjugate (ADC), no substantial agonistic effect on the proliferation of HER2-expressing cancer cells, and provide for effective ADCC-mediated killing of HER2-expressing cells, as well as any combination of the foregoing properties.

These and other aspects of the invention are described in further detail below.

BRIEF DESCRIPTION OF THE DRAWINGS

FIGS. 1A-1D: Alignment of HuMab heavy chain variable region (VH) sequences with germline (reference) sequences (FIGS. 1A-1D). In each VH sequence, the amino acids that differ from those of the germline (reference) at specific positions are highlighted. Consensus VH sequences are shown, where "X" indicates positions at which alternative amino acids (selected from those aligned at the indicated position) are possible. The CDR1, CDR2, and CDR3 sequences are underlined in each VH sequence. The consensus CDR sequences are further defined in Table 4.

FIGS. 2A-2B: Alignment of HuMab light chain variable region (VL) sequences with germline (reference) sequences (FIGS. 2A-2B). In each VL sequence, the amino acids that differ from those of the germline (reference) at specific positions are highlighted. In FIG. 2A, all VL sequences derived from the same V-segment (IgKV3-20-01), but the closest J-segment differed between antibodies. Consensus VL sequences are shown, where "X" indicates positions at which alternative amino acids (selected from those aligned at the indicated position) are possible. The CDR1, CDR2, and CDR3 sequences are underlined in each VL sequence. The consensus CDR sequences are further defined in Table 4.

(FIG. 7A) Data shown are mean fluorescence intensities (MFI) of one representative experiment with AU565 cells treated with non-conjugated and anti-kappa-ETA'-conjugated HER2 antibodies. (FIG. 7B) Data shown are mean fluorescence intensities (MFI) of one representative experiment with A431 cells treated with non-conjugated and anti-kappa-ETA'-conjugated HER2 antibodies. See Example 17 for details.

DETAILED DESCRIPTION OF THE INVENTION

Definitions

Figure 3A:
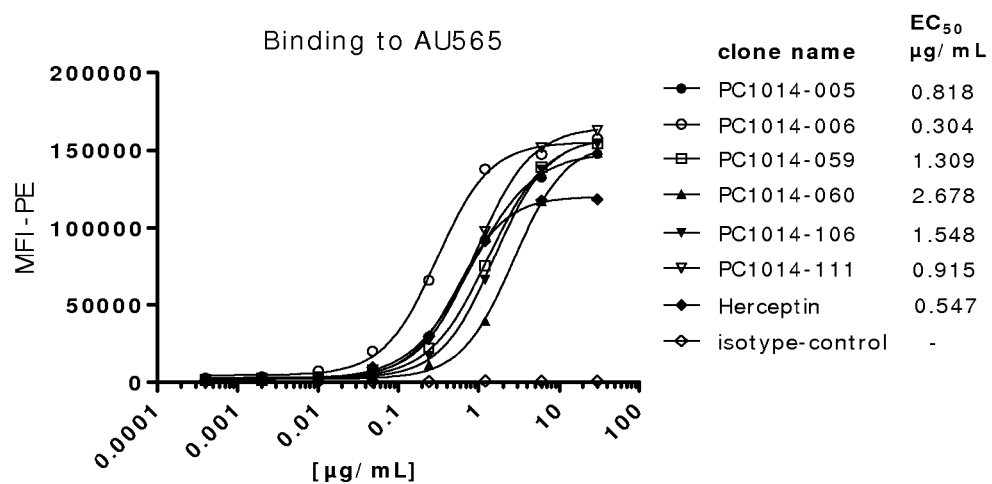
FIGS. 3A-3B: Binding curves of HER2 antibodies to (FIG. 3A) high (AU565) and (FIG. 3B) low (A431) HER2 expressing cell lines, determined as described in Example 12. Data shown are mean fluorescence intensities (MFI) of one representative experiment for each cell line. The $EC_{50}$ values indicate the apparent affinities.

The term "HER2" (also known as ErbB-2, NEU, HER-2, and CD340), when used herein, refers to human epidermal growth factor receptor 2 (SwissProt P04626) and includes any variants, isoforms and species homologs of HER2 which are naturally expressed by cells, including tumor cells, or are expressed on cells transfected with the HER2 gene. Species homologs include rhesus monkey HER2 (macaca mulatta; Genbank accession No. GI:109114897).

The term "immunoglobulin" refers to a class of structurally related glycoproteins consisting of two pairs of polypeptide chains, one pair of light (L) low molecular weight chains and one pair of heavy (H) chains, all four interconnected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$ or VH) and a heavy chain constant region. The heavy chain constant region typically is comprised of three domains, $C_H1$, $C_H2$, and $C_H3$. Each light chain typically is comprised of a light chain variable region (abbreviated herein as $V_L$ or VL) and a light chain constant region. The light chain constant region typically is comprised of one domain, $C_L$. The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)). Unless otherwise stated or contradicted by context, CDR sequences herein are identified according to IMGT rules (Brochet X., Nucl Acids Res. 2008; 36:W503-508 and Lefranc M P., Nucleic Acids Research 1999; 27:209-212; see also internet http address imgt.cines.fr/IMGT_vquest/vquest?livret=0&Option=humanIg. However, the numbering of amino acid residues in an antibody sequence can also be performed by the method described in Kabat et al., Sequences of Proteins of Immunological Interest, 5th Ed. Public Health Service, National Institutes of Health, Bethesda, Md. (1991) (phrases such as "variable domain residue numbering as in Kabat", "Kabat position" or "according to Kabat" herein refer to this numbering system). Particularly, for numbering of amino acids in the constant region, the EU index numbering system according to Kabat et al, supra, can be used. The Kabat numbering of residues may be determined for a given antibody by alignment at regions of homology of the sequence of the antibody with a "standard" Kabat numbered sequence.

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. A HER2 antibody may also be a bispecific antibody, diabody, or similar molecule (see for instance PNAS USA 90(14), 6444-8 (1993) for a description of diabodies). Indeed, bispecific antibodies, diabodies, and the like, provided by the present invention may bind any suitable target in addition to a portion of HER2. As indicated above, the term antibody herein, unless otherwise stated or clearly contradicted by context, includes fragments of an antibody that are antigen-binding fragments, i.e., retain the ability to specifically bind to the antigen. It has been shown that the antigen-binding function of an antibody may be performed by fragments of a full-length antibody. Examples of antigen-binding fragments encompassed within the term "antibody" include (i) a Fab' or Fab fragment, a monovalent fragment consisting of the $V_L$, $V_H$, $C_L$ and $C_H1$ domains, or a monovalent antibody as described in WO2007059782 (Genmab); (ii) F(ab')$_2$ fragments, bivalent fragments comprising two Fab fragments linked by a disulfide bridge at the hinge region; (iii) a Fd fragment consisting essentially of the $V_H$ and $C_H1$ domains; (iv) a Fv fragment consisting essentially of the $V_L$ and $V_H$ domains of a single arm of an antibody, (v) a dAb fragment (Ward et al., Nature 341, 544-546 (1989)), which consists essentially of a $V_H$ domain and also called domain antibodies (Holt et al; Trends Biotechnol. 2003 November; 21(11):484-90); (vi) camelid or nanobodies (Revets et al; Expert Opin Biol Ther. 2005 January; 5(1):111-24) and (vii) an isolated complementarity determining region (CDR). Furthermore, although the two domains of the Fv fragment, $V_L$ and $V_H$, are coded for by separate genes, they may be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention, as well as bispecific formats of such fragments, are discussed further herein. It also should be understood that the term antibody, unless specified otherwise, also includes polyclonal antibodies, monoclonal antibodies (mAbs), antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

As used herein, "isotype" refers to the immunoglobulin class (for instance IgG1, IgG2, IgG3, IgG4, IgD, IgA, IgE, or IgM) that is encoded by heavy chain constant region genes.

The term "monovalent antibody" means in the context of the present invention that an antibody molecule is capable of binding a single molecule of the antigen, and thus is not able of antigen crosslinking.

An "antibody deficient in effector function" or an "effector-function-deficient antibody" refers to an antibody which has a significantly reduced or no ability to activate one or more effector mechanisms, such as complement activation or Fc receptor binding. Thus, effector-function deficient antibodies have significantly reduced or no ability to mediate antibody-dependent cell-mediated cytotoxicity (ADCC) and/or complement-dependent cytotoxicity (CDC). An example of such an antibody is IgG4.

A "HER2 antibody" or "anti-HER2 antibody" is an antibody as described above, which binds specifically to the antigen HER2.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

As used herein, a human antibody is "derived from" a particular germline sequence if the antibody is obtained from a system using human immunoglobulin sequences, for instance by immunizing a transgenic mouse carrying human immunoglobulin genes or by screening a human immunoglobulin gene library, and wherein the selected human antibody is at least 90%, such as at least 95%, for instance at least 96%, such as at least 97%, for instance at least 98%, or such as at least 99% identical in amino acid sequence to the amino acid sequence encoded by the germline immunoglobulin gene. Typically, outside the heavy chain CDR3, a human antibody derived from a particular human germline sequence will display no more than 20 amino acid differences, e.g. no more than 10 amino acid differences, such as no more than 9, 8, 7, 6 or 5, for instance no more than 4, 3, 2, or 1 amino acid difference from the amino acid sequence encoded by the germline immunoglobulin gene.

In a preferred embodiment, the antibody of the invention is isolated. An "isolated antibody," as used herein, is intended to refer to an antibody which is substantially free of other antibodies having different antigenic specificities (for instance an isolated antibody that specifically binds to HER2 is substantially free of antibodies that specifically bind antigens other than HER2). An isolated antibody that specifically binds to an epitope, isoform or variant of HER2 may, however, have cross-reactivity to other related antigens, for instance from other species (such as HER2 species homologs). Moreover, an isolated antibody may be substantially free of other cellular material and/or chemicals. In one embodiment of the present invention, two or more "isolated" monoclonal antibodies having different antigen-binding specificities are combined in a well-defined composition.

When used herein in the context of two or more antibodies, the term "competes with" or "cross-competes with" indicates that the two or more antibodies compete for binding to HER2, e.g. compete for HER2 binding in the assay described in Example 14. An antibody "blocks" or "cross-blocks" one or more other antibodies from binding to HER2 if the antibody competes with the one or more other antibodies 25% or more, with 25%-74% representing "partial block" and 75%-100% representing "full block", preferably as determined using the assay of Example 14. For some pairs of antibodies, competition or blocking in the assay of the Examples is only observed when one antibody is coated on the plate and the other is used to compete, and not vice versa. Unless otherwise defined or negated by context, the terms "competes with", "cross-competes with", "blocks" or "cross-blocks" when used herein is also intended to cover such pairs of antibodies.

The term "epitope" means a protein determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The epitope may comprise amino acid residues directly involved in the binding (also called immunodominant component of the epitope) and other amino acid residues, which are not directly involved in the binding, such as amino acid residues which are effectively blocked by the specifically antigen binding peptide (in other words, the amino acid residue is within the footprint of the specifically antigen binding peptide).

The term "monoclonal antibody" as used herein refers to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal nonhuman animal, such as a transgenic mouse, having a genome comprising a human heavy chain transgene and a light chain transgene, fused to an immortalized cell.

As used herein, the term "binding" in the context of the binding of an antibody to a predetermined antigen typically is a binding with an affinity corresponding to a KD of about $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antigen as the ligand and the antibody as the analyte, and binds to the predetermined antigen with an affinity corresponding to a KD that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the KD of the antibody, so that when the KD of the antibody is very low (that is, the antibody is highly specific), then the amount with which the affinity for the antigen is lower than the affinity for a non-specific antigen may be at least 10,000 fold.

The term "$k_d$" ($sec^{-1}$), as used herein, refers to the dissociation rate constant of a particular antibody-antigen interaction. Said value is also referred to as the $k_{off}$ value.

The term "$k_a$" ($M^{-1} \times sec^{-1}$), as used herein, refers to the association rate constant of a particular antibody-antigen interaction.

The term "$K_D$" (M), as used herein, refers to the dissociation equilibrium constant of a particular antibody-antigen interaction.

The term "$K_A$" ($M^{-1}$), as used herein, refers to the association equilibrium constant of a particular antibody-antigen interaction and is obtained by dividing the $k_a$ by the $k_d$.

As used herein, the term "inhibits proliferation" (e.g. referring to cells, such as tumor cells) is intended to include any substantial decrease in the cell proliferation when contacted with a HER2 antibody as compared to the proliferation of the same cells not in contact with a HER2 antibody, e.g., the inhibition of proliferation of a cell culture by at least about 10%, at least about 20% or at least about 30%, or at least as much as a reference antibody such as trastuzumab, e.g., as determined by an assay in the Examples.

As used herein, the term "promotes proliferation" (e.g. referring to cells, such as tumor cells) is intended to include any substantial increase in the cell proliferation when contacted with a HER2 antibody as compared to the proliferation of the same cells not in contact with a HER2 antibody, e.g., the promotion of proliferation of a cell culture by at least about 10%, at least about 20% or at least about 30%, or at least as much as a reference antibody as F5, e.g., as determined by an assay in the Examples.

As used herein, "internalization", when used in the context of a HER2 antibody includes any mechanism by which the antibody is internalized into a HER2-expressing cell from the cell-surface and/or from surrounding medium, e.g., via endocytosis. The internalization of an antibody can be evaluated using a direct assay measuring the amount of internalized antibody (such as, e.g., the fab-CypHer5E assay described in Example 18), or an indirect assay where the effect of an internalized antibody-toxin conjugate is measured (such as, e.g., the anti-kappa-ETA' assay of Example 17).

The present invention also provides antibodies comprising functional variants of the VL region, VH region, or one or more CDRs of the antibodies of the examples. A functional variant of a VL, VH, or CDR used in the context of a HER2 antibody still allows the antibody to retain at least a substantial proportion (at least about 50%, 60%, 70%, 80%, 90%, 95% or more) of the affinity/avidity and/or the specificity/selectivity of the parent antibody and in some cases such a HER2 antibody may be associated with greater affinity, selectivity and/or specificity than the parent antibody.

Such functional variants typically retain significant sequence identity to the parent antibody. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm.

Exemplary variants include those which differ from a parent antibody VH and/or VL sequence shown in FIGS. 1 and 2 at one or more "variant" amino acid positions, denoted "X" in the corresponding consensus sequence. Preferred variants are those in which the new amino acid is selected from those at the corresponding position in one of the aligned sequences in FIG. 1 or 2 (for details on CDR sequence variants, see Table 4). Alternatively or additionally, the sequence of VH, VL or CDR variants may differ from the sequence of the VH, VL or CDR of the parent antibody sequences mainly by conservative substitutions; for instance at least 10, such as at least 9, 8, 7, 6, 5, 4, 3, 2 or 1 of the substitutions in the variant are conservative amino acid residue replacements. In the context of the present invention, conservative substitutions may be defined by substitutions within the classes of amino acids reflected in the following table:

| Amino acid residue classes for conservative substitutions | |
| --- | --- |
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

The term "recombinant host cell" (or simply "host cell"), as used herein, is intended to refer to a cell into which an expression vector has been introduced, e.g. an expression vector encoding an antibody of the invention. Recombinant host cells include, for example, transfectomas, such as CHO cells, HEK293 cells, NS/0 cells, and lymphocytic cells.

The term "transgenic non-human animal" refers to a non-human animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human HER2 antibodies when immunized with HER2 antigen and/or cells expressing HER2. The human heavy chain transgene may be integrated into the chromosomal DNA of the mouse, as is the case for transgenic mice, for instance HuMAb mice, such as HCo7, HCo12, or HCo17 mice, or the human heavy chain transgene may be maintained extrachromosomally, as is the case for transchromosomal KM mice as described in WO02/43478. Similar mice, having a larger human Ab gene repertoire, include HCo7 and HCo20 (see e.g. WO2009097006). Such transgenic and transchromosomal mice (collectively referred to herein as "transgenic mice") are capable of producing multiple isotypes of human monoclonal antibodies to a given antigen (such as IgG, IgA, IgM, IgD and/or IgE) by undergoing V-D-J recombination and isotype switching. Transgenic, nonhuman animal can also be used for production of antibodies against a specific antigen by introducing genes encoding such specific antibody, for example by operatively linking the genes to a gene which is expressed in the milk of the animal.

"Treatment" refers to the administration of an effective amount of a therapeutically active compound of the present invention with the purpose of easing, ameliorating, arresting or eradicating (curing) symptoms or disease states.

An "effective amount" refers to an amount effective, at dosages and for periods of time necessary, to achieve a desired therapeutic result. A therapeutically effective amount of a HER2 antibody may vary according to factors such as the disease state, age, sex, and weight of the individual, and the ability of the HER2 antibody to elicit a desired response in the individual. A therapeutically effective amount is also one in which any toxic or detrimental effects of the antibody or antibody portion are outweighed by the therapeutically beneficial effects.

An "anti-idiotypic" antibody is an antibody which recognizes unique determinants generally associated with the antigen-binding site of an antibody.

Further Aspects and Embodiments of the Invention

As described above, in a first aspect, the invention relates to a monoclonal antibody which binds HER2.

Monoclonal antibodies of the present invention may be produced, e.g., by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624-628 (1991) and Marks et al., J. Mol. Biol. 222, 581-597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc.

In one embodiment, the antibody of the invention is a human antibody. Human monoclonal antibodies directed against HER2 may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice".

The HuMAb mouse contains a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al., Nature 368, 856-859 (1994)). Accordingly, the mice exhibit reduced expression of mouse IgM or K and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N. Handbook of Experimental Pharmacology 113, 49-101 (1994), Lonberg, N. and Huszar, D., Intern. Rev. Immunol. Vol. 13 65-93 (1995) and Harding, F. and Lonberg, N. Ann. N.Y. Acad. Sci 764 536-546 (1995)). The preparation of HuMAb mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. No. 5,545,806, U.S. Pat. No. 5,569,825, U.S. Pat. No. 5,625,126, U.S. Pat. No. 5,633,425, U.S. Pat. No. 5,789,650, U.S. Pat. No. 5,877,397, U.S. Pat. No. 5,661,016, U.S. Pat. No. 5,814,318, U.S. Pat. No. 5,874,299, U.S. Pat. No. 5,770,429, U.S. Pat. No. 5,545,807, WO 98/24884, WO 94/25585, WO 93/1227, WO 92/22645, WO 92/03918 and WO 01/09187.

The HCo7, HCo12, HCo17 and HCo20 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), and a KCo5 human kappa light chain transgene (as described in Fishwild et al., Nature Biotechnology 14, 845-851 (1996)). Additionally, the Hco7 mice have a HCo7 human heavy chain transgene (as described in U.S. Pat. No. 5,770,429), the HCo12 mice have a HCo12 human heavy chain transgene (as described in Example 2 of WO 01/14424), the HCo17 mice have a HCo17 human heavy chain transgene (as described in Example 2 of WO 01/09187) and the HCo20 mice have a HCo20 human heavy chain transgene. The resulting mice express human immunoglobulin heavy and kappa light chain transgenes in a background homozygous for disruption of the endogenous mouse heavy and kappa light chain loci.

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478. HCo12-Balb/C mice can be generated by crossing HCo12 to KCo5[J/K](Balb) as described in WO 097006. Splenocytes from these transgenic mice may be used to generate hybridomas that secrete human monoclonal antibodies according to well known techniques.

Further, human antibodies of the present invention or antibodies of the present invention from other species may be identified through display-type technologies, including, without limitation, phage display, retroviral display, ribosomal display, and other techniques, using techniques well known in the art and the resulting molecules may be subjected to additional maturation, such as affinity maturation, as such techniques are well known in the art (see for instance Hoogenboom et al., J. Mol. Biol. 227, 381 (1991) (phage display), Vaughan et al., Nature Biotech 14, 309 (1996) (phage display), Hanes and Plucthau, PNAS USA 94, 4937-4942 (1997) (ribosomal display), Parmley and Smith, Gene 73, 305-318 (1988) (phage display), Scott TIBS 17, 241-245 (1992), Cwirla et al., PNAS USA 87, 6378-6382 (1990), Russel et al., Nucl. Acids Research 21, 1081-1085 (1993), Hogenboom et al., Immunol. Reviews 130, 43-68 (1992), Chiswell and McCafferty TIBTECH 10, 80-84 (1992), and U.S. Pat. No. 5,733,743). If display technologies are utilized to produce antibodies that are not human, such antibodies may be humanized.

In one aspect the HER2 antibody of the invention binds to domain III of human HER2. The inventors of the present invention have shown that antibodies 005, 006, 059, 060, 106 and 111 show enhanced internalization, lysosomal degradation and toxicity in the anti-kappa-ETA' model system. Thus without being bound by any theory binding of an antibody to domain III of HER2 may be important for internalization of the antibody and therefore useful for antibody drug conjugates (ADCs). Antibodies 005, 006, 059, 060, 106 and 111 recognize an epitope that resides in HER2 domain III, which has no known function in heterodimerization of HER2. Whereas HER2 domain IV (bound by Herceptin) has been reported to be involved in ligand independent heterodimerization of HER2 (Juntilla et al., Cancer Cell 2009; 15:429-440), and HER2 domain II (bound by pertuzumab) has been reported to be involved in ligand induced heterodimerization of HER2 (Landgraf et al., Breast Cancer Research 2007; 9:202). We hypothesize that the formation of HER2/ErbB heterodimers is critical to get sufficient internalization and degradation of HER2 antibody/receptor complexes. Therefore, HER2 antibodies that utilize HER2 heterodimer driven internalization and degradation seem very attractive for future HER2-targeted ADC therapeutics. In particular, on tumor cells that do not overexpress HER2 at extremely high levels, the formation of HER2/ErbB heterodimers may represent an attractive approach for HER2 antibodies to deliver an ADC.

In one aspect of the HER2 antibody of the invention, the antibody does not block the binding to soluble HER2 of a second antibody, optionally in immobilized form, comprising the VH and VL sequences of any of trastuzumab, pertuzumab, F1, and C5, when determined as described in Example 14.

In an additional or alternative aspect of the antibody of the invention, the antibody blocks or cross-blocks the binding to soluble HER2 of one or more of the novel human antibodies described herein.

In one embodiment, the antibody blocks the binding to soluble HER2 of a reference antibody, optionally immobilized, wherein the reference antibody comprises a VH region comprising the sequence of SEQ ID NO:1 and a VL region comprising the sequence of SEQ ID NO:5 (005), preferably wherein the antibody is fully blocking when determined as described in Example 14.

In one embodiment, the antibody blocks the binding to soluble HER2 of a reference antibody, optionally immobilized, wherein the reference antibody comprises a VH region comprising the sequence of SEQ ID NO:8 and a VL region comprising the sequence of SEQ ID NO:12 (006), preferably wherein the antibody is fully-blocking when determined as described in Example 14.

In one embodiment, the antibody blocks the binding to soluble HER2 of a reference antibody, optionally immobilized, wherein the reference antibody comprises a VH region comprising the sequence of SEQ ID NO:15 and a VL region comprising the sequence of SEQ ID NO:19 (059), preferably wherein the antibody is fully-blocking when determined as described in Example 14.

In one embodiment, the antibody blocks the binding to soluble HER2 of a reference antibody, optionally immobilized, wherein the reference antibody comprises a VH region comprising the sequence of SEQ ID NO:22 and a VL region comprising the sequence of SEQ ID NO:26 (060), preferably wherein the antibody is fully-blocking when determined as described in Example 14.

In one embodiment, the antibody blocks the binding to soluble HER2 of a reference antibody, optionally immobilized, wherein the reference antibody comprises a VH region comprising the sequence of SEQ ID NO:29 and a VL region comprising the sequence of SEQ ID NO:33 (106), preferably wherein the antibody is fully-blocking when determined as described in Example 14.

In one embodiment, the antibody blocks the binding to soluble HER2 of a reference antibody, optionally immobilized, wherein the reference antibody comprises a VH region comprising the sequence of SEQ ID NO:36 and a VL region comprising the sequence of SEQ ID NO:40 (111), preferably wherein the antibody is fully-blocking when determined as described in Example 14.

In separate and specific embodiments, the antibody blocks the binding of two, three, four, five, or six reference antibodies of the preceding embodiment, such as, e.g., antibodies 005 and 111, antibodies 005 and 006; antibodies 059 and 106; antibodies 006 and 059; antibodies 059, 106, 005 and 060; antibodies 006, 59, 060, and 111; or antibodies 059, 106, 005, 060, 111 and 006.

In one embodiment, the antibody competes for at least 25%, preferably at least 50% for binding to soluble HER2 with all of the following:

a reference antibody, optionally immobilized, comprising a VH region comprising the sequence of SEQ ID NO:1 and a VL region comprising the sequence of SEQ ID NO:5 (005);

a reference antibody, optionally immobilized, comprising a VH region comprising the sequence of SEQ ID NO:15 and a VL region comprising the sequence of SEQ ID NO:19 (059);

a reference antibody, optionally immobilized, comprising a VH region comprising the sequence of SEQ ID NO:22 and a VL region comprising the sequence of SEQ ID NO:26 (060);

a reference antibody, optionally immobilized, comprising a VH region comprising the sequence of SEQ ID NO:29 and a VL region comprising the sequence of SEQ ID NO:33 (106);

a reference antibody, optionally immobilized, comprising a VH region comprising the sequence of SEQ ID NO:36 and a VL region comprising the sequence of SEQ ID NO:40 (111), when determined as described in Example 14.

In one embodiment, the antibody, when immobilized, blocks the binding to soluble HER2 of at least one antibody selected from the group consisting of:

an antibody comprising a VH region comprising the sequence of SEQ ID NO:1 and a VL region comprising the sequence of SEQ ID NO:5 (005);

an antibody comprising a VH region comprising the sequence of SEQ ID NO:8 and a VL region comprising the sequence of SEQ ID NO:12 (006);

an antibody comprising a VH region comprising the sequence of SEQ ID NO:15 and a VL region comprising the sequence of SEQ ID NO:19 (059);

an antibody comprising a VH region comprising the sequence of SEQ ID NO:22 and a VL region comprising the sequence of SEQ ID NO:26 (060);

an antibody comprising a VH region comprising the sequence of SEQ ID NO:29 and a VL region comprising the sequence of SEQ ID NO:33 (106); and an antibody comprising a VH region comprising the sequence of SEQ ID NO:36 and a VL region comprising the sequence of SEQ ID NO:40 (111), preferably wherein the immobilized antibody is fully-blocking when determined as described in Example 14.

In one embodiment, the antibody, when immobilized, competes for binding to soluble HER2 with all antibodies defined in the preceding embodiment for 25% or more, preferably 50% or more, when determined as described in Example 14.

In one aspect of the antibody of the invention, the antibody binds the same epitope on HER2 as one or more of the novel human antibodies described herein.

In one embodiment, the antibody binds the same epitope as an antibody comprising a VH region comprising the sequence of SEQ ID NO:1 and a VL region comprising the sequence of SEQ ID NO:5 (005).

In one embodiment, the antibody binds the same epitope as an antibody comprising a VH region comprising the sequence of SEQ ID NO:8 and a VL region comprising the sequence of SEQ ID NO:12 (006).

In one embodiment, the antibody binds the same epitope as an antibody comprising a VH region comprising the sequence of SEQ ID NO:15 and a VL region comprising the sequence of SEQ ID NO:19 (059).

In one embodiment, the antibody binds the same epitope as an antibody comprising a VH region comprising the sequence of SEQ ID NO:22 and a VL region comprising the sequence of SEQ ID NO:26 (060).

In one embodiment, the antibody binds the same epitope as an antibody comprising a VH region comprising the sequence of SEQ ID NO:29 and a VL region comprising the sequence of SEQ ID NO:33 (106).

In one embodiment, the antibody binds the same epitope as an antibody comprising a VH region comprising the sequence of SEQ ID NO:36 and a VL region comprising the sequence of SEQ ID NO:40 (111).

In one embodiment, the antibody binds to the same epitope as at least one antibody selected from the group consisting of:

a) an antibody comprising a VH region comprising the sequence of SEQ ID NO:43 and a VL region comprising the sequence of SEQ ID NO:44 (041)

b) an antibody comprising a VH region comprising the sequence of SEQ ID NO:45 and a VL region comprising the sequence of SEQ ID NO:46 (150), and c) an antibody comprising a VH region comprising the sequence of SEQ ID NO:47 and a VL region comprising the sequence of SEQ ID NO:48 (067);

d) an antibody comprising a VH region comprising the sequence of SEQ ID NO:49 and a VL region comprising the sequence of SEQ ID NO:50 (072);

e) an antibody comprising a VH region comprising the sequence of SEQ ID NO:51 and a VL region comprising the sequence of SEQ ID NO:52 (163);

f) an antibody comprising a VH region comprising the sequence of SEQ ID NO:53 and a VL region comprising the sequence of SEQ ID NO:54 (093);

g) an antibody comprising a VH region comprising the sequence of SEQ ID NO:55 and a VL region comprising the sequence of SEQ ID NO:56 (044).

In another additional or alternative aspect of the antibody of the invention, the antibody binds to HER2 and comprises a VH CDR3, VH region and/or VL region sequence similar or identical to a sequence of the novel antibodies described herein.

In one embodiment, the antibody comprises a VH CDR3 region having an amino acid sequence selected from the group consisting of SEQ ID No:59, such as the sequence of SEQ ID No:4, 25, 32 (005, 060, 106), optionally wherein the VH region is derived from the IgHV5-51-1 germline;

SEQ ID No:62, such as the sequence of SEQ ID NO:11 (006), optionally wherein the VH region is derived from the IgHV3-23-1 germline sequence;

SEQ ID NO:65, such as the sequence of SEQ ID NO:18 (059), optionally wherein the VH region is derived from the IgHV1-18-1 germline sequence; or SEQ ID NO:67, such as the sequence of SEQ ID NO:39 (111), optionally wherein the VH region is derived from the IgHV1-69-4 germline sequence.

In one embodiment, the antibody comprises a VH CDR3 region comprising the amino acid sequence of SEQ ID NO: 59, wherein X1=Q, H, or L; X2=R, A, T, or K; X3=G; X4=D; X5=R or none; X6=G or none; X7=Y or F; X8=Y or D; X9=Y, F, or H; X10=Y, D, S, F, or N; X11=M or L; and X12=V or I; preferably, wherein X1=Q, X2=R or A; X5=X6=none; X7=Y or F; X8=Y; X9=F; X10=Y; and X12=V. In a particular embodiment the antibody comprises a VH CDR3 region comprising the amino acid sequence of SEQ ID NO: 59, wherein X1=Q, X2=R or A; X3=G; X4=D, X5=X6=none; X7=Y or F; X8=Y; X9=F; X10=Y; and X12=V. In one embodiment the antibody comprises a VH CDR3 region comprising the amino acid sequence of SEQ ID NO: 59, wherein X1=Q, X2=K; X3=G; X4=D, X5=X6=none; X7=F; X8=Y; X9=X10=F; X11=L; and X12=V; or wherein X1=Q, X2=A; X3=G; X4=D, X5=X6=none; X7=X8=Y; X9=Y; X10=N; X11=M; and X12=V; or wherein X1=Q, X2=K; X3=G; X4=D, X5=X6=none; X7=X8=Y; X9=H; X10=Y; X11=L; and X12=V; or wherein X1=Q, X2=K; X3=G; X4=D, X5=X6=none; X7=Y; X8=Y; X9=F; X10=N; X11=L; and X12=V; or wherein X1=Q, X2=R; X3=G; X4=D, X5=X6=none; X7=Y; X8=Y; X9=F; X10=N; X11=L; and X12=V; or wherein X1=Q, X2=R; X3=G; X4=D, X5=X6=none; X7=Y; X8=Y; X9=X10=F; X11=L; and X12=I; or wherein X1=Q, X2=A; X3=G; X4=D, X5=X6=none; X7=X8=Y; X9=Y; X10=N; X11=M; and X12=V.

In one embodiment, the antibody comprises a VH CDR3 region of one of antibodies 041, 150, 067, 072, 163, or 093, as shown in FIG. 1, optionally wherein the VH region is derived from an IgHV5-51-1 germline.

In one embodiment, the antibody comprises a VH region selected from the group consisting of a) a VH region comprising the CDR1, CDR2 and CDR3 sequences of SEQ ID NOs:57, 58 and 59, such as a. a CDR1 sequence selected from SEQ ID NOs:2, 23, and 30; a CDR2 sequence selected from 3, 24, and 31; and a CDR3 sequence selected from 4, 25, and 32 (005, 060, 106), b. the CDR1, CDR2, and CDR3 sequences of SEQ ID NOs:2, 3 and 4, respectively (005), c. the CDR1, CDR2, and CDR3 sequences of SEQ ID NOs:23, 24 and 25, respectively (060), d. the CDR1, CDR2, and CDR3 sequences of SEQ ID NOs:32, 33 and 34, respectively (106), optionally where the VH region is derived from an IgHV5-51-1 germline;

b) a VH region comprising the CDR1, CDR2 and CDR3 sequences of SEQ ID NOs:60, 61 and 62, such the CDR1, CDR2 and CDR3 sequences of SEQ ID NOs:9, 10, and 11, respectively (006), optionally where the VH region is derived from an IgHV3-23-1 germline; and c) a VH region comprising the CDR1, CDR2, and CDR3 sequences of SEQ ID NOs:63, 64, and 65, such as the CRD1, CDR2, and CDR3 sequences of SEQ ID NOs: 16, 17 and 18 (059), respectively, optionally where the VH region is derived from an IgHV1-18-1 germline; and d) a VH region comprising the CDR1, CDR2, and CDR3 sequences of SEQ ID NOs:66, 38 and 67, such as the CRD1, CDR2, and CDR3 sequences of SEQ ID NOs: 37, 38 and 39 (111), respectively, optionally where the VH region is derived from an IgHV1-69-4 germline.

In one embodiment, the antibody comprises a VH region selected from the preceding embodiments (a), (c) or (d) and a VL region comprising the CDR1, CDR2, and CDR3 sequences of SEQ ID NO:68, GAS, and SEQ ID No:69, respectively, such as a CDR1 sequence selected from SEQ ID Nos: 6, 20, 27, 34 and 41, a CDR2 which is GAS, and a CDR3 sequence selected from 7, 21, 28, 35 and 42 (005, 059, 060, 106, 111); respectively, optionally where the VL region is derived from an IgKV3-20-01 germline.

In one embodiment, the antibody comprises a VH region which is the preceding embodiment (b) and a VL region comprising the CDR1, CDR2, and CDR3 sequences of SEQ ID NO:13, DAS, and SEQ ID NO:14 (006), respectively, optionally where the VL region is derived from IgKV3-11-01.

In one embodiment, the antibody comprises a VH region comprising the CDR1, CDR2 and CDR3 sequences of SEQ ID NOs:2, 3 and 4, respectively; and a VL region comprising the CDR1, CDR2 and CDR3 sequences of SEQ ID NOs:6, GAS, and SEQ ID NO:7, respectively (005).

In one embodiment, the antibody comprises a VH region comprising the CDR1, CDR2 and CDR3 sequences of SEQ ID NOs:9, 10 and 11, respectively; and a VL region comprising the CDR1, CDR2 and CDR3 sequences of SEQ ID NOs:13, DAS, and SEQ ID NO:14, respectively (006).

In one embodiment, the antibody comprises a VH region comprising the CDR1, CDR2 and CDR3 sequences of SEQ ID NOs:16, 17 and 18, respectively; and a VL region comprising the CDR1, CDR2 and CDR3 sequences of SEQ ID NOs:20, GAS, and SEQ ID NO:21, respectively (059).

In one embodiment, the antibody comprises a VH region comprising the CDR1, CDR2 and CDR3 sequences of SEQ ID NOs:23, 24 and 25, respectively; and a VL region comprising the CDR1, CDR2 and CDR3 sequences of SEQ ID NOs:27, GAS, and SEQ ID NO:28, respectively (060).

In one embodiment, the antibody comprises a VH region comprising the CDR1, CDR2 and CDR3 sequences of SEQ ID NOs:30, 31 and 32, respectively; and a VL region comprising the CDR1, CDR2 and CDR3 sequences of SEQ ID NOs:34, GAS, and SEQ ID NO:35, respectively (106).

In one embodiment, the antibody comprises a VH region comprising the CDR1, CDR2 and CDR3 sequences of SEQ ID NOs:37, 38 and 39, respectively; and a VL region comprising the CDR1, CDR2 and CDR3 sequences of SEQ ID NOs:41, GAS, and SEQ ID NO:42, respectively (111).

In one embodiment, the antibody comprises a VH region comprising the CDR1 sequence of SEQ ID NO:57, wherein $X1=S$; $X2=T$ and $X3=S$; the CDR2 sequence of SEQ ID NO:58, wherein $X1=Y$ and $X2=H$ and the CDR3 sequence of SEQ ID NO:59, wherein $X1=Q$, $X2=K$; $X3=G$; $X4=D$, $X5=X6=$none; $X7=F$; $X8=Y$; $X9=X10=F$; $X11=L$; and $X12=V$; and a VL region comprising the CDR1 sequence of SEQ ID NO:68, wherein $X1=X2=S$; the CDR2 sequence GAS; and the CDR3 sequence of SEQ ID NO: 69, wherein $X1=Q$, $X2=S$, $X3=X4=$none and $X5=L$ (041).

In one embodiment, the antibody comprises a VH region comprising the CDR1 sequence of SEQ ID NO:57, wherein $X1=S$; $X2=T$ and $X3=S$; the CDR2 sequence of SEQ ID NO:58, wherein $X1=Y$ and $X2=H$, and the CDR3 sequence of SEQ ID NO:59, wherein $X1=Q$, $X2=A$; $X3=G$; $X4=D$, $X5=X6=$none; $X7=X8=Y$; $X9=Y$; $X10=N$; $X11=M$; and $X12=V$; and a VL region comprising the CDR1 sequence of SEQ ID NO:68, wherein $X1=X2=S$; the CDR2 sequence GAS; and the CDR3 sequence of SEQ ID NO: 69, wherein $X1=Q$, $X2=S$, $X3=X4=$none and $X5=L$ (150).

In one embodiment, the antibody comprises a VH region comprising the CDR1 sequence of SEQ ID NO:57, wherein $X1=S$; $X2=T$ and $X3=S$; the CDR2 sequence of SEQ ID NO:58, wherein $X1=Y$ and $X2=D$, and the CDR3 sequence of SEQ ID NO:59, $X1=Q$, $X2=K$; $X3=G$; $X4=D$, $X5=X6=$none; $X7=X8=Y$; $X9=H$; $X10=Y$; $X11=L$; and $X12=V$; and a VL region comprising the CDR1 sequence of SEQ ID NO:68, wherein $X1=X2=S$; the CDR2 sequence GAS; and the CDR3 sequence of SEQ ID NO: 69, wherein $X1=Q$, $X2=S$, $X3=P$, $X4=R$ and $X5=L$ (067).

In one embodiment, the antibody comprises a VH region comprising the CDR1 sequence of SEQ ID NO:57, wherein $X1=S$; $X2=T$ and $X3=S$; the CDR2 sequence of SEQ ID NO:58, wherein $X1=Y$ and $X2=D$, and the CDR3 sequence of SEQ ID NO:59, wherein $X1=Q$, $X2=K$; $X3=G$; $X4=D$, $X5=X6=$none; $X7=Y$; $X8=Y$; $X9=F$; $X10=N$; $X11=L$; and $X12=V$; and a VL region comprising the CDR1 sequence of SEQ ID NO:68, wherein $X1=X2=S$; the CDR2 sequence GAS; and the CDR3 sequence of SEQ ID NO: 69, wherein $X1=Q$, $X2=S$, $X3=P$, $X4=R$ and $X5=L$ (072).

In one embodiment, the antibody comprises a VH region comprising the CDR1 sequence of SEQ ID NO:57, wherein $X1=R$; $X2=I$ and $X3=S$; the CDR2 sequence of SEQ ID NO:58, wherein $X1=Y$ and $X2=D$, and the CDR3 sequence of SEQ ID NO:59, wherein $X1=Q$, $X2=R$; $X3=G$; $X4=D$, $X5=X6=$none; $X7=Y$; $X8=Y$; $X9=F$; $X10=N$; $X11=L$; and $X12=V$; and a VL region comprising the CDR1 sequence of SEQ ID NO:68, wherein $X1=X2=S$; the CDR2 sequence GAS; and the CDR3 sequence of SEQ ID NO: 69, wherein $X1=Q$, $X2=S$, $X3=X4=$none and $X5=L$ (163).

In one embodiment, the antibody comprises a VH region comprising the CDR1 sequence of SEQ ID NO:57, wherein $X1=S$; $X2=T$ and $X3=S$; the CDR2 sequence of SEQ ID NO:58, wherein $X1=Y$ and $X2=D$, and the CDR3 sequence of SEQ ID NO:59, wherein $X1=Q$, $X2=R$; $X3=G$; $X4=D$, $X5=X6=$none; $X7=Y$; $X8=Y$; $X9=X10=F$; $X11=L$; and $X12=I$; and a VL region comprising the CDR1 sequence of SEQ ID NO:68, wherein $X1=X2=S$; the CDR2 sequence GAS; and the CDR3 sequence of SEQ ID NO: 69, wherein $X1=Q$, $X2=S$, $X3=X4=$none and $X5=L$ (093).

In one embodiment, the antibody comprises a VH region comprising the CDR1 sequence of SEQ ID NO:57, wherein $X1=R$; $X2=S$ and $X3=S$; the CDR2 sequence of SEQ ID NO:58, wherein $X1=F$ and $X2=D$, and the CDR3 sequence of SEQ ID NO:59, wherein $X1=Q$, $X2=A$; $X3=G$; $X4=D$, $X5=X6=$none; $X7=X8=Y$; $X9=Y$; $X10=N$; $X11=M$; and $X12=V$; and a VL region comprising the CDR1 sequence of SEQ ID NO:68, wherein $X1=X2=S$; the CDR2 sequence GAS; and the CDR3 sequence of SEQ ID NO: 69, wherein $X1=Q$, $X2=S$, $X3=X4=$none and $X5=L$ (044).

In separate embodiments, the antibody comprises:

a) a VH region comprising the sequence of SEQ ID NO:1 and, preferably, a VL region comprising the sequence of SEQ ID NO:5 (005)

b) a VH region comprising the sequence of SEQ ID NO:8 and, preferably, a VL region comprising the sequence of SEQ ID NO:11 (006)

c) a VH region comprising the sequence of SEQ ID NO:15 and, preferably, a VL region comprising the sequence of SEQ ID NO:19 (059)

d) a VH region comprising the sequence of SEQ ID NO:22 and, preferably, a VL region comprising the sequence of SEQ ID NO:26 (060)

e) a VH region comprising the sequence of SEQ ID NO:29 and, preferably, a VL region comprising the sequence of SEQ ID NO:33 (106)

f) a VH region comprising the sequence of SEQ ID NO:36 and, preferably, a VL region comprising the sequence of SEQ ID NO:40 (111)

g) a VH region comprising the sequence of SEQ ID NO:43 and, preferably, a VL region comprising the sequence of SEQ ID NO:44 (041)

h) a VH region comprising the sequence of SEQ ID NO:45 and, preferably, a VL region comprising the sequence of SEQ ID NO:46 (150), i) a VH region comprising the sequence of SEQ ID NO:47 and, preferably, a VL region comprising the sequence of SEQ ID NO:48 (067), j) a VH region comprising the sequence of SEQ ID NO:49 and, preferably, a VL region comprising the sequence of SEQ ID NO:50 (072), k) a VH region comprising the sequence of SEQ ID NO:51 and, preferably, a VL region comprising the sequence of SEQ ID NO:52 (163), l) a VH region comprising the sequence of SEQ ID NO:53 and, preferably, a VL region comprising the sequence of SEQ ID NO:54 (093), m) a VH region comprising the sequence of SEQ ID NO:55 and, preferably, a VL region comprising the sequence of SEQ ID NO:56 (044), n) a variant of any of said antibodies, wherein said variant preferably has at most 1,2 or 3 amino-acid modifications, more preferably amino-acid substitutions, such as conservative amino acid substitutions and substitutions where the new amino acid is one at the same position in an aligned sequence in FIG. 1 or 2, particularly at positions indicated by "X" in the corresponding consensus sequence.

In another aspect of the antibody of the invention, the antibody partially or completely cross-blocks the binding to soluble HER2 of one or more of the novel antibodies described herein, preferably when determined as described in Example 14; and is further characterized by one or more properties determined as described in Examples 12, 13, 15, 16, 17 and 18.

In one embodiment, the HER2 antibody has a lower $EC_{50}$ value (half maximal effective concentration) than trastuzumab in binding to A431 cells, preferably an $EC_{50}$ value lower than 0.80, 0.50 or 0.30 µg/ml, when determined as described in Example 12, and cross-blocks at least one antibody selected from the group consisting of a) an antibody comprising a VH region comprising the sequence of SEQ ID NO:1 and a VL region comprising the sequence of SEQ ID NO:5 (005);

b) an antibody comprising a VH region comprising the sequence of SEQ ID NO:8 and a VL region comprising the sequence of SEQ ID NO:11 (006); and c) an antibody comprising a VH region comprising the sequence of SEQ ID NO:15 and a VL region comprising the sequence of SEQ ID NO:19 (059).

In separate and specific embodiments, the antibody of the preceding embodiment fully cross-blocks, preferably bind to the same epitope as, antibody 005, 006, 059, or a combination thereof.

In an additional or alternative embodiment, the HER antibody specifically binds HER2-positive Rhesus epithelial cells, when determined as described in Example 13, and cross-blocks at least one antibody selected from the group consisting of:

a) an antibody comprising a VH region comprising the sequence of SEQ ID NO:1 and a VL region comprising the sequence of SEQ ID NO:5 (005)

b) an antibody comprising a VH region comprising the sequence of SEQ ID NO:8 and a VL region comprising the sequence of SEQ ID NO:11 (006)

c) an antibody comprising a VH region comprising the sequence of SEQ ID NO:15 and a VL region comprising the sequence of SEQ ID NO:19 (059)

d) an antibody comprising a VH region comprising the sequence of SEQ ID NO:22 and a VL region comprising the sequence of SEQ ID NO:26 (060)

e) an antibody comprising a VH region comprising the sequence of SEQ ID NO:29 and a VL region comprising the sequence of SEQ ID NO:33 (106)

f) an antibody comprising a VH region comprising the sequence of SEQ ID NO:36 and a VL region comprising the sequence of SEQ ID NO:40 (111).

In separate and specific embodiments, the antibody of the preceding embodiment fully cross-blocks, preferably bind to the same epitope as, antibody 005, 006, 059, 060, 106, 111, or a combination thereof.

In an additional or alternative embodiment, the HER2 antibody specifically binds HER2-expressing AU565 cells but promotes ligand-independent proliferation of the cells less than F5, preferably promoting proliferation less than 30%, more preferably by less than 20%, when determined as described in Example 16, and cross-blocks at least one antibody selected from:

a) an antibody comprising a VH region comprising the sequence of SEQ ID NO:1 and a VL region comprising the sequence of SEQ ID NO:5 (005); and b) an antibody comprising a VH region comprising the sequence of SEQ ID NO:22 and a VL region comprising the sequence of SEQ ID NO:26 (060).

In separate and specific embodiments, the antibody of the preceding embodiment fully cross-blocks, preferably bind to the same epitope as, antibody 005, 060, or a combination thereof.

In an additional or alternative embodiment, the antibody, when conjugated directly or indirectly to a therapeutic moiety such as a truncated form of the pseudomonas-exotoxin A, is more effective than trastuzumab in killing AU565 cells, A431 cells, or both AU565 and A431 cells, when determined as described in Example 17.

In one embodiment, the conjugated antibody kills at least 60%, preferably at least 70% AU565 cells or A431 cells, when determined as described in Example 17, and cross-blocks at least one antibody selected from a) an antibody comprising a VH region comprising the sequence of SEQ ID NO:1 and a VL region comprising the sequence of SEQ ID NO:5 (005)

b) an antibody comprising a VH region comprising the sequence of SEQ ID NO:22 and a VL region comprising the sequence of SEQ ID NO:26 (060)

c) an antibody comprising a VH region comprising the sequence of SEQ ID NO:15 and a VL region comprising the sequence of SEQ ID NO:19 (059), and
d) an antibody comprising a VH region comprising the sequence of SEQ ID NO:36 and a VL region comprising the sequence of SEQ ID NO:40 (111).

In separate and specific embodiments, the antibody of the preceding embodiment fully cross-blocks, preferably bind to the same epitope as, antibody 005, 060, 059, 111, or a combination thereof.

In an additional or alternative embodiment, the antibody, when conjugated directly or indirectly to a therapeutic moiety, is capable of killing tumor cells expressing a lower average amount of HER2 copies per cell than AU565 cells, such as an average of about 500,000 or less, 100,000 or less, or 30,000 or less copies of HER2 per cell (when determined, e.g., as referred to in Example 12), at concentrations where non-conjugated antibody does not induce killing of the cells, preferably when determined as described in Example 17.

In one embodiment, the antibody of the preceding embodiment kills at least 80% of A431 cells when determined as described in Example 17, and cross-blocks at least one antibody selected from
 a) an antibody comprising a VH region comprising the sequence of SEQ ID NO:1 and a VL region comprising the sequence of SEQ ID NO:5 (005), and
 b) an antibody comprising a VH region comprising the sequence of SEQ ID NO:22 and a VL region comprising the sequence of SEQ ID NO:26 (060).

In separate and specific embodiments, the antibody of the preceding embodiment fully cross-blocks, preferably bind to the same epitope as, antibody 005, 060, or a combination thereof.

In an additional or alternative embodiment, the antibody is internalized by tumor cells expressing HER2, such as AU565 cells, more than trastuzumab is, preferably more than twice or three times the amount of internalized trastuzumab, preferably when determined according to Example 18, and cross-blocks at least one antibody selected from the group consisting of:
 a) an antibody comprising a VH region comprising the sequence of SEQ ID NO:1 and a VL region comprising the sequence of SEQ ID NO:5 (005)
 b) an antibody comprising a VH region comprising the sequence of SEQ ID NO:8 and a VL region comprising the sequence of SEQ ID NO:11 (006)
 c) an antibody comprising a VH region comprising the sequence of SEQ ID NO:15 and a VL region comprising the sequence of SEQ ID NO:19 (059)
 d) an antibody comprising a VH region comprising the sequence of SEQ ID NO:22 and a VL region comprising the sequence of SEQ ID NO:26 (060)
 e) an antibody comprising a VH region comprising the sequence of SEQ ID NO:29 and a VL region comprising the sequence of SEQ ID NO:33 (106)
 f) an antibody comprising a VH region comprising the sequence of SEQ ID NO:36 and a VL region comprising the sequence of SEQ ID NO:40 (111).

In separate and specific embodiments, the antibody of the preceding embodiment fully cross-blocks, preferably bind to the same epitope as, antibody 005, 006, 059, 060, 106, 111, or a combination thereof.

In a further embodiment, the antibody promotes proliferation of HER2 expressing tumor cells less than F5, and is internalized more than trastuzumab into HER2 expressing tumor cells, preferably when determined as described in the Examples.

Antibody Formats

The present invention provides HER2 antibodies which efficiently bind to and internalize into HER2-expressing tumor cells, typically without significantly promoting ligand-independent proliferation of the cells. Depending on the desired functional properties for a particular use, particular antibodies can be selected from the set of antibodies provided in the present invention and/or their format can be adapted to change these properties, as described below.

The antibody of the invention can be of any isotype. The choice of isotype typically will be guided by the desired effector functions, such as ADCC induction. Exemplary isotypes are IgG1, IgG2, IgG3, and IgG4. Either of the human light chain constant regions, kappa or lambda, may be used. If desired, the class of a HER2 antibody of the present invention may be switched by known methods. For example, an antibody of the present invention that was originally IgM may be class switched to an IgG antibody of the present invention. Further, class switching techniques may be used to convert one IgG subclass to another, for instance from IgG1 to IgG2. Thus, the effector function of the antibodies of the present invention may be changed by isotype switching to, e.g., an IgG1, IgG2, IgG3, IgG4, IgD, IgA, IgE, or IgM antibody for various therapeutic uses. In one embodiment an antibody of the present invention is an IgG1 antibody, for instance an IgG1,κ.

In a further embodiment, the antibody of the invention is glyco-engineered to reduce fucose and thus enhance ADCC, e.g. by addition of compounds to the culture media during antibody production as described in US2009317869 or as described in van Berkel et al. (2010) Biotechnol. Bioeng. 105:350 or by using FUT8 knockout cells, e.g. as described in Yamane-Ohnuki et al (2004) Biotechnol. Bioeng 87:614. ADCC may alternatively be optimized using the method described by Umaña et al. (1999) Nature Biotech 17:176.

In a further embodiment, the antibody of the invention has been engineered to enhance complement activation, e.g. as described in Natsume et al. (2009) Cancer Sci. 100:2411.

In one embodiment, the antibody of the invention is a full-length antibody, preferably an IgG1 antibody, in particular an IgG1,κ antibody. In another embodiment, the antibody of the invention is an antibody fragment or a single-chain antibody.

Antibody fragments may e.g. be obtained by fragmentation using conventional techniques, and the fragments screened for utility in the same manner as described herein for whole antibodies. For example, F(ab')$_2$ fragments may be generated by treating an antibody with pepsin. The resulting F(ab')$_2$ fragment may be treated to reduce disulfide bridges with a reducing agent, such as dithiothreitol, to produce Fab' fragments. Fab fragments may be obtained by treating an antibody with papain. A F(ab')$_2$ fragment may also be produced by binding Fab' fragments via a thioether bond or a disulfide bond. Antibody fragments may also be generated by expression of nucleic acids encoding such fragments in recombinant cells (see for instance Evans et al., J. Immunol. Meth. 184, 123-38 (1995)). For example, a chimeric gene encoding a portion of an F(ab')$_2$ fragment could include DNA sequences encoding the $C_H1$ domain and hinge region of the H chain, followed by a translational stop codon to yield such a truncated antibody fragment molecule.

As explained above, in one embodiment, the HER2 antibody of the invention is a bivalent antibody.

In another embodiment, the HER2 antibody of the invention is a monovalent antibody.

In one embodiment, the antibody of the invention is a Fab fragment or a one-armed antibody, such as described in US20080063641 (Genentech) or other monovalent antibody, e.g. such as described in WO2007048037 (Amgen).

In a preferred embodiment, a monovalent antibody has a structure as described in WO2007059782 (Genmab) (incorporated herein by reference) having a deletion of the hinge region. Accordingly, in one embodiment, the antibody is a monovalent antibody, wherein said HER2 antibody is constructed by a method comprising:

i) providing a nucleic acid construct encoding the light chain of said monovalent antibody, said construct comprising a nucleotide sequence encoding the VL region of a selected antigen specific HER2 antibody and a nucleotide sequence encoding the constant CL region of an Ig, wherein said nucleotide sequence encoding the VL region of a selected antigen specific antibody and said nucleotide sequence encoding the CL region of an Ig are operably linked together, and wherein, in case of an IgG1 subtype, the nucleotide sequence encoding the CL region has been modified such that the CL region does not contain any amino acids capable of forming disulfide bonds or covalent bonds with other peptides comprising an identical amino acid sequence of the CL region in the presence of polyclonal human IgG or when administered to an animal or human being;

ii) providing a nucleic acid construct encoding the heavy chain of said monovalent antibody, said construct comprising a nucleotide sequence encoding the VH region of a selected antigen specific antibody and a nucleotide sequence encoding a constant CH region of a human Ig, wherein the nucleotide sequence encoding the CH region has been modified such that the region corresponding to the hinge region and, as required by the Ig subtype, other regions of the CH region, such as the CH3 region, does not comprise any amino acid residues which participate in the formation of disulphide bonds or covalent or stable non-covalent inter-heavy chain bonds with other peptides comprising an identical amino acid sequence of the CH region of the human Ig in the presence of polyclonal human IgG or when administered to an animal human being, wherein said nucleotide sequence encoding the VH region of a selected antigen specific antibody and said nucleotide sequence encoding the CH region of said Ig are operably linked together;

iii) providing a cell expression system for producing said monovalent antibody;

iv) producing said monovalent antibody by co-expressing the nucleic acid constructs of (i) and (ii) in cells of the cell expression system of (iii).

Similarly, in one embodiment, the HER2 antibody is a monovalent antibody, which comprises (i) a variable region of an antibody of the invention as described herein or an antigen binding part of the said region, and (ii) a $C_H$ region of an immunoglobulin or a fragment thereof comprising the $C_H2$ and $C_H3$ regions, wherein the $C_H$ region or fragment thereof has been modified such that the region corresponding to the hinge region and, if the immunoglobulin is not an IgG4 subtype, other regions of the $C_H$ region, such as the $C_H3$ region, do not comprise any amino acid residues, which are capable of forming disulfide bonds with an identical $C_H$ region or other covalent or stable non-covalent inter-heavy chain bonds with an identical $C_H$ region in the presence of polyclonal human IgG.

In a further embodiment hereof, the heavy chain of the monovalent HER2 antibody has been modified such that the entire hinge has been deleted.

In another further embodiment, said monovalent antibody is of the IgG4 subtype, but the $C_H3$ region has been modified so that one or more of the following amino acid substitutions have been made:

Numbering of CH3 mutations

| KABAT* | EU index G4* | Mutations |
|---|---|---|
| E378 | E357 | E357A or E357T or E357V or E357I |
| S387 | S364 | S364R or S364K |
| T389 | T366 | T366A or T366R or T366K or T366N |
| L391 | L368 | L368A or L368V or L368E or L368G or L368S or L368T |
| D427 | D399 | D399A or D399T or D399S |
| F436 | F405 | F405A or F405L or F405T or F405D or F405R or F405Q or F405K or F405Y |
| Y438 | Y407 | Y407A or Y407E or Y407Q or Y407K or Y407F |
| F436 and Y438 | F405 and Y407 | (F405T and Y407E) or (F405D and Y407E) |
| D427 and Y438 | D399 and Y407 | (D399S and Y407Q) or (D399S and Y407K) or (D399S and Y407E) |

*KABAT indicates amino acid numbering according to Kabat (Kabat et al., *Sequences of Proteins of Immunological Interest, 5th Ed.* Public Health Service, National Institutes of Health, Bethesda, MD. (1991). EU index indicates amino acid numbering according to EU index as outlined in Kabat et al., (supra).

In another further embodiment, the sequence of said monovalent antibody has been modified so that it does not comprise any acceptor sites for N-linked glycosylation.

HER2 antibodies of the invention also include single chain antibodies. Single chain antibodies are peptides in which the heavy and light chain Fv regions are connected. In one embodiment, the present invention provides a single-chain Fv (scFv) wherein the heavy and light chains in the Fv of a HER2 antibody of the present invention are joined with a flexible peptide linker (typically of about 10, 12, 15 or more amino acid residues) in a single peptide chain. Methods of producing such antibodies are described in for instance U.S. Pat. No. 4,946,778, Pluckthun in The Pharmacology of Monoclonal Antibodies, vol. 113, Rosenburg and Moore eds. Springer-Verlag, New York, pp. 269-315 (1994), Bird et al., Science 242, 423-426 (1988), Huston et al., PNAS USA 85, 5879-5883 (1988) and McCafferty et al., Nature 348, 552-554 (1990). The single chain antibody may be monovalent, if only a single $V_H$ and $V_L$ are used, bivalent, if two $V_H$ and $V_L$ are used, or polyvalent, if more than two $V_H$ and $V_L$ are used.

In one embodiment, the HER2 antibody of the invention is an effector-function-deficient antibody. In one embodiment, the effector-function-deficient HER2 antibody is a stabilized IgG4 antibody, which has been modified to prevent Fab-arm exchange (van der Neut Kolfschoten et al. (2007) Science 317(5844):1554-7). Examples of suitable stabilized IgG4 antibodies are antibodies, wherein arginine at position 409 in a heavy chain constant region of human IgG4, which is indicated in the EU index as in Kabat et al., is substituted with lysine, threonine, methionine, or leucine, preferably lysine (described in WO2006033386 (Kirin)) and/or wherein the hinge region has been modified to comprise a Cys-Pro-Pro-Cys sequence.

In one embodiment, the stabilized IgG4 HER2 antibody is an IgG4 antibody comprising a heavy chain and a light chain, wherein said heavy chain comprises a human IgG4 constant region having a residue selected from the group consisting of: Lys, Ala, Thr, Met and Leu at the position corresponding to 409 and/or a residue selected from the group consisting of: Ala, Val, Gly, Ile and Leu at the position corresponding to 405, and wherein said antibody optionally comprises one or more further substitutions, deletions and/or insertions, but does not comprise a Cys-Pro-Pro-Cys sequence in the hinge region. Preferably, said antibody comprises a Lys or Ala residue at the position corresponding to 409 or the CH3 region of the antibody has been replaced by the CH3 region of human IgG1, of human IgG2 or of human IgG3. See also WO2008145142 (Genmab).

In an even further embodiment, the stabilized IgG4 HER2 antibody is an IgG4 antibody comprising a heavy chain and a light chain, wherein said heavy chain comprises a human IgG4 constant region having a residue selected from the group consisting of: Lys, Ala, Thr, Met and Leu at the position corresponding to 409 and/or a residue selected from the group consisting of: Ala, Val, Gly, Ile and Leu at the position corresponding to 405, and wherein said antibody optionally comprises one or more further substitutions, deletions and/or insertions and wherein said antibody comprises a Cys-Pro-Pro-Cys sequence in the hinge region. Preferably, said antibody comprises a Lys or Ala residue at the position corresponding to 409 or the CH3 region of the antibody has been replaced by the CH3 region of human IgG1, of human IgG2 or of human IgG3.

In a further embodiment, the effector-function-deficient HER2 antibody is an antibody of a non-IgG4 type, e.g. IgG1, IgG2 or IgG3 which has been mutated such that the ability to mediate effector functions, such as ADCC, has been reduced or even eliminated. Such mutations have e.g. been described in Dall'Acqua W F et al., J Immunol. 177(2): 1129-1138 (2006) and Hezareh M, J Virol.; 75(24):12161-12168 (2001).

Conjugates

In a further embodiment, the present invention provides a HER2 antibody conjugated to a therapeutic moiety, such as a cytotoxin, a chemotherapeutic drug, a cytokine, an immunosuppressant, or a radioisotope. Such conjugates are referred to herein as "immunoconjugates". Immunoconjugates which include one or more cytotoxins are referred to as "immunotoxins".

A cytotoxin or cytotoxic agent includes any agent that is detrimental to (e.g., kills) cells. Suitable therapeutic agents for forming immunoconjugates of the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, maytansine or an analog or derivative thereof, mitoxantrone, mithramycin, actinomycin D, 1-dehydrotestosterone, glucocorticoids, procaine, tetracaine, lidocaine, propranolol, and puromycin; calicheamicin or analogs or derivatives thereof; antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin; as well as duocarmycin A, duocarmycin SA, CC-1065 (a.k.a. rachelmycin), or analogs or derivatives of CC-1065), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), anti-mitotic agents (e.g., tubulin-inhibitors) such as monomethyl auristatin monomethyl auristatin F, or other analogs or derivatives of dolastatin 10; diphtheria toxin and related molecules (such as diphtheria A chain and active fragments thereof and hybrid molecules); ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), momordica charantia inhibitor, curcin, crotin, sapaonaria officinalis inhibitor, gelonin, mitogellin, restrictocin, phenomycin, and enomycin toxins. Other suitable conjugated molecules include antimicrobial/lytic peptides such as CLIP, Magainin 2, mellitin, Cecropin, and P18; ribonuclease (RNase), DNase I, Staphylococcal enterotoxin-A, pokeweed antiviral protein, diphtherin toxin, and Pseudomonas endotoxin. See, for example, Pastan et al., Cell 47, 641 (1986) and Goldenberg, Calif. A Cancer Journal for Clinicians 44, 43 (1994). Therapeutic agents that may be administered in combination with a HER2 antibody of the present invention as described elsewhere herein, such as, e.g., anti-cancer cytokines or chemokines, are also candidates for therapeutic moieties useful for conjugation to an antibody of the present invention.

In one embodiment, a HER2 antibody of the invention comprises a conjugated nucleic acid or nucleic acid-associated molecule. In one such embodiment, the conjugated nucleic acid is a cytotoxic ribonuclease, an antisense nucleic acid, an inhibitory RNA molecule (e.g., a siRNA molecule) or an immunostimulatory nucleic acid (e.g., an immunostimulatory CpG motif-containing DNA molecule). In another embodiment, a HER2 antibody of the invention is conjugated to an aptamer or a ribozyme.

In one embodiment, HER2 antibodies comprising one or more radiolabeled amino acids are provided. A radiolabeled HER2 antibody may be used for both diagnostic and therapeutic purposes (conjugation to radiolabeled molecules is another possible feature). Non-limiting examples of labels for polypeptides include 3H, 14C, 15N, 35S, 90Y, 99Tc, and 125I, 131I, and 186Re.

In one embodiment, the antibody is conjugated to a radioisotope or to a radioisotope-containing chelate. For example, the antibody can be conjugated to a chelator linker, e.g. DOTA, DTPA or tiuxetan, which allows for the antibody to be complexed with a radioisotope. The antibody may also or alternatively comprise or be conjugated to one or more radiolabeled amino acids or other radiolabeled molecule. A radiolabeled CD74 antibody may be used for both diagnostic and therapeutic purposes. Non-limiting examples of radioisotopes include $^{3}$H, $^{14}$C, $^{15}$N, $^{35}$S, $^{90}$Y, $^{99}$Tc, $^{125}$I, $^{111}$In, $^{131}$I, $^{186}$Re, $^{213}$Bs, $^{225}$Ac and $^{227}$Th.

HER2 antibodies may also be chemically modified by covalent conjugation to a polymer to for instance increase their circulating half-life. Exemplary polymers, and methods to attach them to peptides, are illustrated in for instance U.S. Pat. No. 4,766,106, U.S. Pat. No. 4,179,337, U.S. Pat. No. 4,495,285 and U.S. Pat. No. 4,609,546. Additional polymers include polyoxyethylated polyols and polyethylene glycol (PEG) (e.g., a PEG with a molecular weight of between about 1,000 and about 40,000, such as between about 2,000 and about 20,000).

Any method known in the art for conjugating the HER2 antibody to the conjugated molecule(s), such as those described above, may be employed, including the methods described by Hunter et al., Nature 144, 945 (1962), David et al., Biochemistry 13, 1014 (1974), Pain et al., J. Immunol. Meth. 40, 219 (1981) and Nygren, J. Histochem. and Cytochem. 30, 407 (1982). Such antibodies may be produced by chemically conjugating the other moiety to the N-terminal side or C-terminal side of the HER2 antibody or fragment thereof (e.g., a HER2 antibody H or L chain) (see, e.g., Antibody Engineering Handbook, edited by Osamu Kanemitsu, published by Chijin Shokan (1994)). Such conjugated antibody derivatives may also be generated by conjugation at internal residues or sugars, where appropriate.

The agents may be coupled either directly or indirectly to a HER2 antibody of the present invention. One example of indirect coupling of a second agent is coupling via a spacer moiety to cysteine or lysine residues in the antibody. In one embodiment, a HER2 antibody is conjugated to a prodrug molecule that can be activated in vivo to a therapeutic drug via a spacer or linker. After administration, the spacers or linkers are cleaved by tumor-cell associated enzymes or other tumor-specific conditions, by which the active drug is formed. Examples of such prodrug technologies and linkers are described in WO02083180, WO2004043493, WO2007018431, WO2007089149, and WO2009017394 by Syntarga B V, et al. Suitable antibody-prodrug technology and duocarmycin analogs can also be found in U.S. Pat. No. 6,989,452 (Medarex).

In one embodiment, the HER2 antibody of the present invention is attached to a chelator linker, e.g. tiuxetan, which allows for the antibody to be conjugated to a radioisotope.

Bispecific Antibodies

In a further aspect, the invention relates to a bispecific molecule comprising a first antigen binding site from a HER2 antibody of the invention as described herein above and a second antigen binding site with a different binding specificity, such as a binding specificity for a human effector cell, a human Fc receptor, a T cell receptor, a B cell receptor or a binding specificity for a non-overlapping epitope of HER2, i.e. a bispecific antibody wherein the first and second antigen binding sites do not cross-block each other for binding to HER2, e.g. when tested as described in Example 14.

Exemplary bispecific antibody molecules of the invention comprise (i) two antibodies, one with a specificity to HER2 and another to a second target that are conjugated together, (ii) a single antibody that has one chain or arm specific to HER2 and a second chain or arm specific to a second molecule, (iii) a single chain antibody that has specificity to HER2 and a second molecule, e.g., via two scFvs linked in tandem by an extra peptide linker; (iv) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (v) a chemically-linked bispecific (Fab')$_2$ fragment; (vi) a Tandab, which is a fusion of two single chain diabodies resulting in a tetravalent bispecific antibody that has two binding sites for each of the target antigens; (vii) a flexibody, which is a combination of scFvs with a diabody resulting in a multivalent molecule; (viii) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (ix) a so-called Scorpion molecule, comprising, e.g., two scFvs fused to both termini of a human Fc-region; and (x) a diabody. In one embodiment, the bispecific antibody of the present invention is a diabody.

In one embodiment, the second molecule is a cancer antigen/tumor-associated antigen such as carcinoembryonic antigen (CEA), prostate specific antigen (PSA), RAGE (renal antigen), α-fetoprotein, CAMEL (CTL-recognized antigen on melanoma), CT antigens (such as MAGE-B5, -B6, -C2, -C3, and D; Mage-12; CT10; NY-ESO-1, SSX-2, GAGE, BAGE, MAGE, and SAGE), mucin antigens (e.g., MUC1, mucin-CA125, etc.), ganglioside antigens, tyrosinase, gp75, c-Met, C-myc, Mart1, MelanA, MUM-1, MUM-2, MUM-3, HLA-B7, Ep-CAM or a cancer-associated integrin, such as α5β3 integrin. In another embodiment, the second molecule is a T cell and/or NK cell antigen, such as CD3 or CD16. In another embodiment, the second molecule is an angiogenic factor or other cancer-associated growth factor, such as a vascular endothelial growth factor, a fibroblast growth factor, epidermal growth factor, angiogenin or a receptor of any of these, particularly receptors associated with cancer progression (for instance another one of the HER receptors; HER1, HER3, or HER4). In one embodiment, the second antigen-binding site binds a different, preferably non-blocking, site on HER2 than the one bound by the antibody of the invention. For example, the second molecule may be derived from, or cross-block HER2-binding of, trastuzumab, pertuzumab, F5, or C1.

Nucleic Acid Sequences, Vectors and Host Cells

In a further aspect, the invention relates to nucleic acid sequences, such as DNA sequences, encoding heavy and light chains of an antibody of the invention.

In one embodiment, the nucleic acid sequence encodes an amino acid sequence selected from the group consisting of: SEQ ID NO: 1, 5, 8, 12, 15, 19, 22, 26, 29, 33, 36, 40, 43, 44, 45, 46, 47, 48, 49, 50, 51, 52, 53, 54, 55, and 56.

In another particular embodiment, the nucleic acid sequence encodes a VH amino acid sequence selected from the group consisting of: SEQ ID NO: 1, 8, 15, 22, 29, 36, 43, 45, 47, 49, 51, 53, and 55.

In another particular embodiment, the nucleic acid sequence encodes a VL amino acid sequence selected from the group consisting of: SEQ ID NO: 5, 12, 19, 26, 33, 40, 44, 46, 48, 50, 52, 54, and 56.

In an even further aspect, the invention relates to an expression vector, or a set of expression vectors, encoding an antibody of the invention. The heavy and light chain of the antibody may be encoded by the same vector or by different vector.

Such expression vectors may be used for recombinant production of antibodies of the invention.

In one embodiment, the expression vector of the invention comprises a nucleotide sequence encoding one or more of the amino acid sequences selected from the group consisting of: SEQ ID NO: 1, 5, 8, 12, 15, 19, 22, 26, 29, 33, 36, 40, 43, 44, 45, 46, 47, 48, 49, 50, 51, 52, 53, 54, 55, and 56.

In another particular embodiment, the expression vector of the invention comprises a nucleotide sequence encoding one or more of the VH amino acid sequences selected from the group consisting of: SEQ ID NO: SEQ ID NO: 1, 8, 15, 22, 29, 36, 43, 45, 47, 49, 51, 53, and 55.

In another particular embodiment, the expression vector of the invention comprises a nucleotide sequence encoding one or more of the VL amino acid sequences selected from the group consisting of: SEQ ID NO: SEQ ID NO: 5, 12, 19, 26, 33, 40, 44, 46, 48, 50, 52, 54, and 56.

In a further embodiment, the expression vector further comprises a nucleotide sequence encoding the constant region of a light chain, a heavy chain or both light and heavy chains of an antibody, e.g. a human antibody.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, a HER2 antibody-encoding nucleic acid is comprised in a naked DNA or RNA vector, including, for example, a linear expression element (as described in for instance Sykes and Johnston, Nat Biotech 17, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in for instance Schakowski et al., Mol Ther 3, 793-800 (2001)), or as a precipitated nucleic acid vector construct, such as a CaPO4-precipitated construct (as described in for instance WO 00/46147, Benvenisty and Reshef, PNAS USA 83, 9551-55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. No. 5,589,466 and U.S. Pat. No. 5,973,972).

Exemplary expression vectors for the antibodies of the invention are also described in Examples 2 and 3.

In one embodiment, the vector is suitable for expression of the HER2 antibody in a bacterial cell. Examples of such vectors include expression vectors such as BlueScript (Stratagene), pIN vectors (Van Heeke & Schuster, J Biol Chem 264, 5503-5509 (1989), pET vectors (Novagen, Madison Wis.) and the like).

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Grant et al., Methods in Enzymol 153, 516-544 (1987)).

An expression vector may also or alternatively be a vector suitable for expression in mammalian cells, e.g. a vector comprising glutamine synthetase as a selectable marker, such as the vectors described in Bebbington (1992) Biotechnology (NY) 10:169-175.

A nucleic acid and/or vector may also comprises a nucleic acid sequence encoding a secretion/localization sequence, which can target a polypeptide, such as a nascent polypeptide chain, to the periplasmic space or into cell culture media. Such sequences are known in the art, and include secretion leader or signal peptides.

In an expression vector of the invention, HER2 antibody-encoding nucleic acids may comprise or be associated with any suitable promoter, enhancer, and other expression-facilitating elements. Examples of such elements include strong expression promoters (e. g., human CMV IE promoter/enhancer as well as RSV, SV40, SL3-3, MMTV, and HIV LTR promoters), effective poly (A) termination sequences, an origin of replication for plasmid product in E. coli, an antibiotic resistance gene as selectable marker, and/or a convenient cloning site (e.g., a polylinker). Nucleic acids may also comprise an inducible promoter as opposed to a constitutive promoter such as CMV IE.

In one embodiment, the HER2 antibody-encoding expression vector may be positioned in and/or delivered to the host cell or host animal via a viral vector.

In an even further aspect, the invention relates to a recombinant eukaryotic or prokaryotic host cell, such as a transfectoma, which produces an antibody of the invention as defined herein. Examples of host cells include yeast, bacterial, and mammalian cells, such as CHO or HEK cells. For example, in one embodiment, the present invention provides a cell comprising a nucleic acid stably integrated into the cellular genome that comprises a sequence coding for expression of a HER2 antibody of the present invention. In another embodiment, the present invention provides a cell comprising a non-integrated nucleic acid, such as a plasmid, cosmid, phagemid, or linear expression element, which comprises a sequence coding for expression of a HER2 antibody of the invention.

In a further aspect, the invention relates to a hybridoma which produces an antibody of the invention as defined herein. In an even further aspect, the invention relates to a transgenic non-human animal or plant comprising nucleic acids encoding a human heavy chain and a human light chain, wherein the animal or plant produces an antibody of the invention of the invention.

In a further aspect, the invention relates to a method for producing a HER2 antibody of the invention, said method comprising the steps of
a) culturing a hybridoma or a host cell of the invention as described herein above, and
b) purifying the antibody of the invention from the culture media.

Compositions

In a further main aspect, the invention relates to a pharmaceutical composition comprising:
a HER2 antibody as defined herein, and
a pharmaceutically-acceptable carrier.

The pharmaceutical composition of the present invention may contain one antibody of the present invention or a combination of different antibodies of the present invention.

The pharmaceutical compositions may be formulated in accordance with conventional techniques such as those disclosed in Remington: The Science and Practice of Pharmacy, 19th Edition, Gennaro, Ed., Mack Publishing Co., Easton, Pa., 1995. A pharmaceutical composition of the present invention may e.g. include diluents, fillers, salts, buffers, detergents (e. g., a nonionic detergent, such as Tween-20 or Tween-80), stabilizers (e. g., sugars or protein-free amino acids), preservatives, tissue fixatives, solubilizers, and/or other materials suitable for inclusion in a pharmaceutical composition.

Pharmaceutically acceptable carriers include any and all suitable solvents, dispersion media, coatings, antibacterial and antifungal agents, isotonicity agents, antioxidants and absorption delaying agents, and the like that are physiologically compatible with a compound of the present invention. Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, carboxymethyl cellulose colloidal solutions, tragacanth gum and injectable organic esters, such as ethyl oleate, and/or various buffers. Pharmaceutically acceptable carriers include sterile aqueous solutions or dispersions and sterile powders for the extemporaneous preparation of sterile injectable solutions or dispersion. Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole, butylated hydroxytoluene, lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art.

Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

The actual dosage levels of the active ingredients in the pharmaceutical compositions may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. In one embodiment, a pharmaceutical composition of the present invention is administered parenterally. "Administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

In one embodiment that pharmaceutical composition is administered by intravenous or subcutaneous injection or infusion.

Uses

In a further main aspect, the invention relates to a HER2 antibody of the invention for use as a medicament.

The HER2 antibodies of the invention may be used for a number of purposes. In particular, the antibodies of the invention may be used for the treatment of various forms of cancer, including metastatic cancer and refractory cancer.

In one embodiment, the HER2 antibodies of the invention are used for the treatment of breast cancer, including primary, metastatic, and refractory breast cancer.

In one embodiment, the HER2 antibodies of the invention are used for the treatment of a form of cancer selected from the group consisting of prostate cancer, non-small cell lung cancer, bladder cancer, ovarian cancer, gastric cancer, colorectal cancer, esophageal cancer, squamous cell carcinoma of the head & neck, cervical cancer, pancreatic cancer, testis cancer, malignant melanoma and a soft-tissue cancer (e.g. synovial sarcoma).

In one embodiment the invention relates to A method for inhibiting growth and/or proliferation of one or more tumor cells expressing HER2, comprising administration, to an individual in need thereof, of an antibody according to the invention.

In one embodiment the antibody is conjugated to another moiety.

In one embodiment the one or more tumor cell co-expresses HER2 and EGFR and/or HER3.

The present invention also relates to a method for treating cancer, comprising
 a) selecting a subject suffering from a cancer comprising tumor cells co-expressing HER2 and EGFR and/or HER3, and
 b) administering to the subject the antibody according to any one of claims 1-35.

In one embodiment the cancer is selected from the group consisting of breast cancer, colorectal cancer, endometrial/cervical cancer, lung cancer, malignant melanoma, ovarian cancer, pancreatic cancer, prostate cancer, testis cancer, a soft-tissue tumor such as synovial sarcoma, and bladder cancer.

Similarly, the invention relates to a method for killing a tumor cell expressing HER2, comprising administration, to an individual in need thereof, of an effective amount of an antibody of the invention, such as an antibody drug-conjugate (ADC).

In one embodiment, said tumor cell is involved in a form of cancer selected from the group consisting of: breast cancer, prostate cancer, non-small cell lung cancer, bladder cancer, ovarian cancer, gastric cancer, colorectal cancer, esophageal cancer and squamous cell carcinoma of the head & neck, cervical cancer, pancreatic cancer, testis cancer, malignant melanoma, and a soft-tissue cancer (e.g., synovial sarcoma).

In one embodiment, the tumor cell is one that co-expresses HER2 and at least one other member of the EGFR family, preferably EGFR, HER3, or both of EGFR and HER3, and is a tumor cell involved in breast cancer, colorectal cancer, endometrial/cervical cancer, lung cancer, malignant melanoma, ovarian cancer, pancreatic cancer, prostate cancer, testis cancer, a soft-tissue tumor (e.g., synovial sarcoma), or bladder cancer.

In one aspect, the invention relates to a method for treating cancer in a subject, comprising selecting a subject suffering from a cancer comprising tumor cells co-expressing HER2 and EGFR and/or HER3, and administering to the subject an antibody of the invention, optionally in the form of an antibody conjugated to a cytotoxic agent or drug. In one embodiment, the subject suffers from a cancer selected from the group consisting of breast cancer, colorectal cancer, endometrial/cervical cancer, lung cancer, malignant melanoma, ovarian cancer, pancreatic cancer, prostate cancer, testis cancer, a soft-tissue tumor (e.g., synovial sarcoma), or bladder cancer.

Also, the invention relates to the use of a monoclonal antibody that binds to human HER2 for the preparation of a medicament for the treatment of cancer, such as one of the specific cancer indications mentioned above.

The invention further relates to a monoclonal antibody for use in the treatment of cancer, such as one of the cancer indications mentioned above.

In a further embodiment of the methods of treatment of the present invention, the efficacy of the treatment is being monitored during the therapy, e.g. at predefined points in time, by determining tumor burden or HER2 expression levels on the relevant tumor cells.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage.

The efficient dosages and the dosage regimens for the HER2 antibodies depend on the disease or condition to be treated and may be determined by the persons skilled in the art. An exemplary, non-limiting range for a therapeutically effective amount of a compound of the present invention is about 0.1-100 mg/kg, such as about 0.1-50 mg/kg, for example about 0.1-20 mg/kg, such as about 0.1-10 mg/kg, for instance about 0.5, about such as 0.3, about 1, about 3, about 5, or about 8 mg/kg.

A physician or veterinarian having ordinary skill in the art may readily determine and prescribe the effective amount of the pharmaceutical composition required. For example, the physician or veterinarian could start doses of the HER2 antibody employed in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce a therapeutic effect. Administration may e.g. be parenteral, such as intravenous, intramuscular or subcutaneous. In one embodiment, the HER2 antibodies may be administered by infusion in a weekly dosage of from 10 to 500 mg/m$^2$, such as of from 200 to 400 mg/m$^2$. Such administration may be repeated, e.g., 1 to 8 times, such as 3 to 5 times. The administration may be performed by continuous infusion over a period of from 2 to 24 hours, such as of from 2 to 12 hours. In one embodiment, the HER2 antibodies may be administered by slow continuous infusion over a long period, such as more than 24 hours, in order to reduce toxic side effects.

In one embodiment the HER2 antibodies may be administered in a weekly dosage of from 250 mg to 2000 mg, such as for example 300 mg, 500 mg, 700 mg, 1000 mg, 1500 mg or 2000 mg, for up to 8 times, such as from 4 to 6 times. Such regimen may be repeated one or more times as necessary, for example, after 6 months or 12 months. The dosage may be determined or adjusted by measuring the amount of compound of the present invention in the blood upon administration by for instance taking out a biological sample and using anti-idiotypic antibodies which target the antigen binding region of the HER2 antibodies of the present invention.

In one embodiment, the HER2 antibodies may be administered by maintenance therapy, such as, e.g., once a week for a period of 6 months or more.

A HER2 antibody may also be administered prophylactically in order to reduce the risk of developing cancer, delay the onset of the occurrence of an event in cancer progression, and/or reduce the risk of recurrence when a cancer is in remission.

HER2 antibodies may also be administered in combination therapy, i.e., combined with other therapeutic agents relevant for the disease or condition to be treated. Accordingly, in one embodiment, the antibody-containing medicament is for combination with one or more further therapeutic agent, such as a cytotoxic, chemotherapeutic or anti-angiogenic agent.

Such combined administration may be simultaneous, separate or sequential. For simultaneous administration the agents may be administered as one composition or as separate compositions, as appropriate. The present invention thus also provides methods for treating a disorder involving cells expressing HER2 as described above, which methods comprise administration of a HER2 antibody of the present invention combined with one or more additional therapeutic agents as described below.

In one embodiment, the present invention provides a method for treating a disorder involving cells expressing HER2 in a subject, which method comprises administration of a therapeutically effective amount of a HER2 antibody of the present invention and at least one additional therapeutic agent to a subject in need thereof.

In one embodiment, the present invention provides a method for treating or preventing cancer, which method comprises administration of a therapeutically effective amount of a HER2 antibody of the present invention and at least one additional therapeutic agent to a subject in need thereof.

In one embodiment, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In another embodiment, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In another embodiment, such an additional therapeutic agent may be selected from an anti-mitotic agent, such as taxanes, for instance docetaxel, and paclitaxel, and *vinca* alkaloids, for instance vindesine, vincristine, vinblastine, and vinorelbine.

In another embodiment, such an additional therapeutic agent may be selected from a topoisomerase inhibitor, such as topotecan or irinotecan, or a cytostatic drug, such as etoposide and teniposide.

In another embodiment, such an additional therapeutic agent may be selected from a growth factor inhibitor, such as an inhibitor of ErbB1 (EGFR) (such as an EGFR antibody, e.g. zalutumumab, cetuximab, panitumumab or nimotuzumab or other EGFR inhibitors, such as gefitinib or erlotinib), another inhibitor of ErbB2 (HER2/neu) (such as a HER2 antibody, e.g. trastuzumab, trastuzumab-DM1 or pertuzumab) or an inhibitor of both EGFR and HER2, such as lapatinib).

In another embodiment, such an additional therapeutic agent may be selected from a tyrosine kinase inhibitor, such as imatinib (Glivec, Gleevec STI571) or lapatinib, PTK787/ZK222584.

In another embodiment, the present invention provides a method for treating a disorder involving cells expressing HER2 in a subject, which method comprises administration of a therapeutically effective amount of an HER2 antibody of the present invention and at least one inhibitor of angiogenesis, neovascularization, and/or other vascularization to a subject in need thereof Examples of such angiogenesis inhibitors are urokinase inhibitors, matrix metalloprotease inhibitors (such as marimastat, neovastat, BAY 12-9566, AG 3340, BMS-275291 and similar agents), inhibitors of endothelial cell migration and proliferation (such as TNP-470, squalamine, 2-methoxyestradiol, combretastatins, endostatin, angiostatin, penicillamine, SCH66336 (Schering-Plough Corp, Madison, N.J.), R115777 (Janssen Pharmaceutica, Inc, Titusville, N.J.) and similar agents), antagonists of angiogenic growth factors (such as such as ZD6474, SU6668, antibodies against angiogenic agents and/or their receptors (such as VEGF (e.g. bevacizumab), bFGF, and angiopoietin-1), thalidomide, thalidomide analogs (such as CC-5013), Sugen 5416, SU5402, antiangiogenic ribozyme (such as angiozyme), interferon α (such as interferon α2a), suramin and similar agents), VEGF-R kinase inhibitors and other anti-angiogenic tyrosine kinase inhibitors (such as SU011248), inhibitors of endothelial-specific integrin/survival signaling (such as vitaxin and similar agents), copper antagonists/chelators (such as tetrathiomolybdate, captopril and similar agents), carboxyamido-triazole (CAI), ABT-627, CM101, interleukin-12 (IL-12), IM862, PNU145156E as well as nucleotide molecules inhibiting angiogenesis (such as antisense-VEGF-cDNA, cDNA coding for angiostatin, cDNA coding for p53 and cDNA coding for deficient VEGF receptor-2).

Other examples of such inhibitors of angiogenesis, neovascularization, and/or other vascularization are anti-angiogenic heparin derivatives (e.g., heperinase III), temozolomide, NK4, macrophage migration inhibitory factor, cyclooxygenase-2 inhibitors, inhibitors of hypoxia-inducible factor 1, anti-angiogenic soy isoflavones, oltipraz, fumagillin and analogs thereof, somatostatin analogues, pentosan polysulfate, tecogalan sodium, dalteparin, tumstatin, thrombospondin, NM-3, combrestatin, canstatin, avastatin, antibodies against other targets, such as anti-alpha-v/beta-3 integrin and anti-kininostatin antibodies.

In one embodiment, a therapeutic agent for use in combination with a HER2 antibody for treating the disorders as described above may be an anti-cancer immunogen, such as a cancer antigen/tumor-associated antigen (e.g., epithelial cell adhesion molecule (EpCAM/TACSTD1), mucin 1 (MUC1), carcinoembryonic antigen (CEA), tumor-associated glycoprotein 72 (TAG-72), gp100, Melan-A, MART-1, KDR, RCAS1, MDA7, cancer-associated viral vaccines (e.g., human papillomavirus vaccines) or tumor-derived heat shock proteins, In one embodiment, a therapeutic agent for use in combination with a HER2 antibody for treating the disorders as described above may be an anti-cancer cytokine, chemokine, or combination thereof. Examples of suitable cytokines and growth factors include IFNγ, IL-2, IL-4, IL-6, IL-7, IL-10, IL-12, IL-13, IL-15, IL-18, IL-23, IL-24, IL-27, IL-28a, IL-28b, IL-29, KGF, IFNα (e.g., INFα2b), IFNβ, GM-CSF, CD40L, Flt3 ligand, stem cell factor, ancestim, and TNFα. Suitable chemokines may include Glu-Leu-Arg (ELR)-negative chemokines such as IP-10, MCP-3, MIG, and SDF-1α from the human CXC and C-C chemokine families. Suitable cytokines include cytokine derivatives, cytokine variants, cytokine fragments, and cytokine fusion proteins.

In one embodiment, a therapeutic agent for use in combination with a HER2 antibody for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. No. 6,440,735 and U.S. Pat. No. 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs,☐ and anti-sense Bcl-2.

In one embodiment, a therapeutic agent for use in combination with a HER2 antibody for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In one embodiment, a therapeutic agent for use in combination with a HER2 antibody for treating the disorders as described above may be an anti-anergic agent, such as compounds are molecules that block the activity of CTLA-4, e.g. ipilimumab.

In one embodiment, a therapeutic agent for use in combination with a HER2 antibody for treating the disorders as described above may be an anti-cancer nucleic acid or an anti-cancer inhibitory RNA molecule.

Examples of other anti-cancer agents, which may be relevant as therapeutic agents for use in combination with a HER2 antibody for treating the disorders as described above are differentiation inducing agents, retinoic acid analogues (such as all trans retinoic acid, 13-cis retinoic acid and similar agents), vitamin D analogues (such as seocalcitol and similar agents), inhibitors of ErbB3, ErbB4, IGF-IR, insulin receptor, PDGFRa, PDGFRbeta, Flk2, Flt4, FGFR1, FGFR2, FGFR3, FGFR4, TRKA, TRKC, RON (such as an anti-RON antibody), Sea, Tie, Tie2, Eph, Ret, Ros, Alk, LTK, PTK7 and similar agents.

Examples of other anti-cancer agents, which may be relevant as therapeutic agents for use in combination with a HER2 antibody for treating the disorders as described above are estramustine and epirubicin.

Examples of other anti-cancer agents, which may be relevant as therapeutic agents for use in combination with a HER2 antibody for treating the disorders as described above are a HSP90 inhibitor like 17-allyl amino geld-anamycin, antibodies directed against a tumor antigen such as PSA, CA125, KSA, integrins, e.g. integrin β1, or inhibitors of VCAM.

Examples of other anti-cancer agents, which may be relevant as therapeutic agents for use in combination with a HER2 antibody for treating the disorders as described above are calcineurin-inhibitors (such as valspodar, PSC 833 and other MDR-1 or p-glycoprotein inhibitors), TOR-inhibitors (such as sirolimus, everolimus and rapamcyin). and inhibitors of "lymphocyte homing" mechanisms (such as FTY720), and agents with effects on cell signaling such as adhesion molecule inhibitors (for instance anti-LFA).

In one embodiment, the HER2 antibody of the invention is for use in combination with one or more other therapeutic antibodies, such as ofatumumab, zanolimumab, daratumumab, ranibizumab, Zenapax, Simulect, Remicade, Humira, Tysabri, Xolair, raptiva and/or rituximab.

In another embodiment, two or more different antibodies of the invention as described herein are used in combination for the treatment of disease. Particularly interesting combinations include two or more non-blocking antibodies. Such combination therapy may lead to binding of an increased number of antibody molecules per cell, which may give increase efficacy, e.g. via activation of complement-mediated lysis.

In addition to the above, other embodiments of combination therapies of the invention include the following:

For the treatment of breast cancer, a HER2 antibody or a therapeutic conjugate thereof, in combination with methotrexate, paclitaxel, doxorubicin, carboplatin, cyclophosphamide, daunorubicin, epirubicin, 5-fluorouracil, gemcitabine, ixabepilone, mutamycin, mitoxantrone, vinorelbine, docetaxel, thiotepa, vincristine, capecitabine, an EGFR antibody (e.g. zalutumumab, cetuximab, panitumumab or nimotuzumab) or other EGFR inhibitor (such as gefitinib or erlotinib), another HER2 antibody or -conjugate (such as, e.g., trastuzumab, trastuzumab-DM1 or pertuzumab), an inhibitor of both EGFR and HER2 (such as lapatinib), and/or in combination with a HER3 inhibitor.

For the treatment of non-small-cell lung cancer, a HER2 antibody in combination with EGFR inhibitors, such as an EGFR antibody, e.g. zalutumumab, cetuximab, panitumumab or nimotuzumab or other EGFR inhibitors (such as gefitinib or erlotinib), or in combination with an another HER2 agent (such as a HER2 antibody, e.g. trastuzumab, trastuzumab-DM1 or pertuzumab) or in combination with an inhibitor of both EGFR and HER2, such as lapatinib, or in combination with a HER3 inhibitor.

For the treatment of colorectal cancer a HER2 antibody in combination with one or more compounds selected from: gemcitabine, bevacizumab, FOLFOX, FOLFIRI, XELOX, IFL, oxaliplatin, irinotecan, 5-FU/LV, Capecitabine, UFT, EGFR targeting agents, such as cetuximab, panitumumab, zalutumumab; VEGF inhibitors, or tyrosine kinase inhibitors such as sunitinib.

For the treatment of prostate cancer a HER2 antibody in combination with one or more compounds selected from: hormonal/antihormonal therapies; such as antiandrogens, Luteinizing hormone releasing hormone (LHRH) agonists, and chemotherapeutics such as taxanes, mitoxantrone, estramustine, 5FU, vinblastine, and ixabepilone.

Radiotherapy—Surgery

In one embodiment, the present invention provides a method for treating a disorder involving cells expressing HER2 in a subject, which method comprises administration of a therapeutically effective amount of a HER2 antibody, such as a HER2 antibody of the present invention, and radiotherapy to a subject in need thereof.

In one embodiment, the present invention provides a method for treating or preventing cancer, which method comprises administration of a therapeutically effective amount of a HER2 antibody, such as a HER2 antibody of the present invention, and radiotherapy to a subject in need thereof.

In one embodiment, the present invention provides the use of a HER2 antibody, such as a HER2 antibody of the present invention, for the preparation of a pharmaceutical composition for treating cancer to be administered in combination with radiotherapy.

Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In a further embodiment, the present invention provides a method for treating or preventing cancer, which method comprises administration to a subject in need thereof of a therapeutically effective amount of a HER2 antibody, such as a HER2 antibody of the present invention, in combination with surgery.

Diagnostic Uses

The HER2 antibodies of the invention may also be used for diagnostic purposes. Thus, in a further aspect, the invention relates to a diagnostic composition comprising a HER2 antibody as defined herein.

In one embodiment, the HER2 antibodies of the present invention may be used in vivo or in vitro for diagnosing diseases wherein activated cells expressing HER2 play an active role in the pathogenesis, by detecting levels of HER2, or levels of cells which contain HER2 on their membrane surface. This may be achieved, for example, by contacting a sample to be tested, optionally along with a control sample, with the HER2 antibody under conditions that allow for formation of a complex between the antibody and HER2.

Thus, in a further aspect, the invention relates to a method for detecting the presence of HER2 antigen, or a cell expressing HER2, in a sample comprising:

contacting the sample with a HER2 antibody of the invention under conditions that allow for formation of a complex between the antibody and HER2; and
analyzing whether a complex has been formed.

In one embodiment, the method is performed in vitro.

More specifically, the present invention provides methods for the identification of, and diagnosis of invasive cells and tissues, and other cells targeted by HER2 antibodies of the present invention, and for the monitoring of the progress of therapeutic treatments, status after treatment, risk of developing cancer, cancer progression, and the like.

Suitable labels for the HER2 antibody and/or secondary antibodies used in such techniques are well-known in the art.

In a further aspect, the invention relates to a kit for detecting the presence of HER2 antigen, or a cell expressing HER2, in a sample comprising
 a HER2 antibody of the invention or a bispecific molecule of the invention; and
 instructions for use of the kit.

In one embodiment, the present invention provides a kit for diagnosis of cancer comprising a container comprising a HER2 antibody, and one or more reagents for detecting binding of the HER2 antibody to HER2. Reagents may include, for example, fluorescent tags, enzymatic tags, or other detectable tags. The reagents may also include secondary or tertiary antibodies or reagents for enzymatic reactions, wherein the enzymatic reactions produce a product that may be visualized.

Anti-Idiotypic Antibodies

In a further aspect, the invention relates to an anti-idiotypic antibody which binds to a HER2 antibody of the invention as described herein.

An anti-idiotypic (Id) antibody is an antibody which recognizes unique determinants generally associated with the antigen-binding site of an antibody. An Id antibody may be prepared by immunizing an animal of the same species and genetic type as the source of a HER2 mAb with the mAb to which an anti-Id is being prepared. The immunized animal typically can recognize and respond to the idiotypic determinants of the immunizing antibody by producing an antibody to these idiotypic determinants (the anti-Id antibody).

An anti-Id antibody may also be used as an "immunogen" to induce an immune response in yet another animal, producing a so-called anti-anti-Id antibody. An anti-anti-Id may be epitopically identical to the original mAb, which induced the anti-Id. Thus, by using antibodies to the idiotypic determinants of a mAb, it is possible to identify other clones expressing antibodies of identical specificity.

The present invention is further illustrated by the following examples, which should not be construed as limiting the scope of the invention.

EXAMPLES

Example 1—Expression Constructs for HER2 and HER2 Variants

Fully codon-optimized constructs for expression of full length HER2 (1255 aa, Swissprot P04626), the extracellular domain (ECD) of HER2 (Her2-ECDHis, aa 1-653 with a C-terminal His6 tag), the naturally occurring HER2 splice variant (Her2-delex16, resulting from exon 16 deletion and lacking aa 633-648) and a truncated form of the HER2 receptor (Her2-stumpy, aa 648-1256), were generated. The construct contained suitable restriction sites for cloning and an optimal Kozak sequence (Kozak, M., Gene 1999; 234 (2):187-208.). The constructs were cloned in the mammalian expression vector pEE13.4 (Lonza Biologics; Bebbington, C. R., et al., Biotechnology (N Y) 1992; 10(2):169-75) and fully sequenced to confirm the correctness of the construct.

Example 2—Expression Constructs for Pertuzumab, C1 and F5

Fully codon-optimized constructs for expression of the heavy chain (HC) and the light chain (LC) of the IgG1 antibodies pertuzumab, C1 and F5 in HEK cells, were generated. The variable regions encoded by these constructs are identical to those described in U.S. Pat. No. 6,949,245 for pertuzumab heavy chain and light chain and U.S. Pat. No. 7,244,826 for C1 and F5 heavy and light chain. For C1 and F5, the mammalian expression vectors p33G1f and p33K or p33L (pcDNA3.3 (Invitrogen)) containing the fully codon optimized constant region for the human IgG1 heavy chain (allotype f), the human kappa light chain or the human lambda light chain, respectively, were used. For pertuzumab, the mammalian expression vectors pG1f (pEE12.4 (Lonza Biologics) and pKappa (pEE6.4 (Lonza Biologics), containing the fully codon-optimized constant region for the human IgG1 heavy chain (allotype f) and the human kappa light chain, respectively, were used.

Trastuzumab (Herceptin®) can be produced in the same manner, using the heavy and light chain sequences described in, e.g., U.S. Pat. No. 7,632,924.

Example 3—Transient Expression in HEK-293 or CHO Cells

Freestyle™ 293-F (a HEK-293 subclone adapted to suspension growth and chemically defined Freestyle medium, (HEK-293F)) cells were obtained from Invitrogen and transfected with the appropriate plasmid DNA, using 293fectin (Invitrogen) according to the manufacturer's instructions. In the case of antibody expression, the appropriate heavy chain and light chain expression vectors were co-expressed.

pEE13.4Her2, pEE13.4Her2-delex16 and pEE13.4Her2-stumpy were transiently transfected in the Freestyle™ CHO-S (Invitrogen) cell line using Freestyle MAX transfection reagent (Invitrogen). Expression of HER2 and Her2-delex16 was tested by means of FACS analysis as described below.

Example 4—Stable Polyclonal Pool Expression in NS0 pEE13.4Her2, pEE13.4Her2-delex16 and pEE13.4Her2-stumpy were stably transfected in NS0 cells by nucleofection (Amaxa). A pool of stably transfected cells was established after selection on glutamine dependent growth, based on the integrated glutamine synthetase selection marker (Barnes, L. M., et al., Cytotechnology 2000; 32(2):109-123).

Example 5—Purification of his-Tagged HER2

Her2ECDHis was expressed in HEK-293F cells. The His-tag in Her2ECDHis enabled purification with immobilized metal affinity chromatography, since the His-tagged protein binds strongly to the resin beads, while other proteins present in the culture supernatant do not bind strongly.

In this process, a chelator fixed onto the chromatographic resin was charged with $Co^{2+}$ cations. Her2ECDHis containing supernatant was incubated with the resin in batch mode (i.e. solution). After incubation, the beads were retrieved from the supernatant and packed into a column. The column was washed in order to remove weakly bound proteins. The strongly bound Her2ECDHis proteins were then eluted with a buffer containing imidazole, which competes with the binding of His to $Co^{2+}$. The eluent was removed from the protein by buffer exchange on a desalting column.

Example 6—Immunization Procedure of Transgenic Mice

Antibodies 005, 006, 041, 044, 059, 060, 067, 072, 093, 106 and 111 were derived from the following immunization procedure: two female HCo12 mice, one female and one male HCo12-Balb/C mouse, one female and one male HCo17 mouse, and two male HCo20 mice (Medarex, San Jose, Calif., USA) were immunized every fortnight, alternating between 5×10$^6$ NS0 cells transiently transfected with Her2ECD intraperitoneal (IP) and 20 µg Her2ECDHis protein coupled to the hapten Keyhole Limpet Hemocyanin (KLH) subcutaneous (SC) at the tail base. A maximum of eight immunizations was performed per mouse (four IP and four SC immunizations). The first immunization with cells was done in complete Freunds' adjuvant (CFA; Difco Laboratories, Detroit, Mich., USA). For all other immunizations, cells were injected IP in PBS and KLH coupled Her2ECD was injected SC using incomplete Freunds' adjuvant (IFA; Difco Laboratories, Detroit, Mich., USA).

Antibody 150 was derived from immunization of one female HCo17 mouse (Medarex) alternating with 5×10$^6$ NS0 cells transiently transfected with Her2delex16 IP and 20 µg Her2ECDHis protein coupled to the hapten Keyhole Limpet Hemocyanin (KLH) SC at the tail base, with an interval of fourteen days. A maximum of eight immunizations was performed (four IP and four SC immunizations). The first immunization with cells was done in complete Freunds' adjuvant (CFA; Difco Laboratories, Detroit, Mich., USA). For all other immunizations, cells were injected IP in PBS and KLH coupled Her2ECD was injected SC using incomplete Freunds' adjuvant (IFA; Difco Laboratories, Detroit, Mich., USA).

Antibody 163 was derived from immunization of one male HCo20 mouse (Medarex) with 20 µg Her2ECDHis protein coupled to the hapten Keyhole Limpet Hemocyanin (KLH), alternating IP and SC at the tailbase with an interval of fourteen days. A maximum of eight immunizations was performed (four IP and four SC immunizations). The first immunization was done IP in complete Freunds' adjuvant (CFA; Difco Laboratories, Detroit, Mich., USA). The other immunizations were injected using incomplete Freunds' adjuvant (IFA; Difco Laboratories, Detroit, Mich., USA).

Mice with at least two sequential titers against TC1014-Her2, TC1014-Her2delex16 or TC1014-Her2stumpy in the antigen specific FMAT screening assay (as described in Example 7), were considered positive and fused.

Example 7—Homogeneous Antigen Specific Screening Assay

The presence of HER2 antibodies in sera of immunized mice or HuMab (human monoclonal antibody) hybridoma or transfectoma culture supernatant was determined by homogeneous antigen specific screening assays (four quadrant) using Fluorometric Micro volume Assay Technology (FMAT; Applied Biosystems, Foster City, Calif., USA). For this, a combination of 4 cell based assays was used. Binding to TC1014-Her2 (HEK-293F cells transiently expressing the HER2 receptor; produced as described above), TC1014-Her2delex16 (HEK-293F cells transiently expressing the extracellular domain of Her2-delex (a 16 amino acid deletion mutant of the HER2 receptor; produced as described above) and TC1014-Her2stumpy (HEK-293F cells transiently expressing the extracellular stumpy domain of the HER2 receptor; produced as described above) as well as HEK293 wild type cells (negative control cells which do not express HER2) was determined. Samples were added to the cells to allow binding to HER2. Subsequently, binding of HuMab was detected using a fluorescent conjugate (Goat anti-Human IgG-Cy5; Jackson ImmunoResearch). TH1014-Pertuzumab (produced in HEK-293F cells) was used as a positive control and HuMab-mouse pooled serum and HuMab-KLH were used as negative controls. The samples were scanned using an Applied Biosystems 8200 Cellular Detection System (8200 CDS) and 'counts×fluorescence' was used as read-out. Samples were stated positive when counts were higher than 50 and counts×fluorescence were at least three times higher than the negative control.

Example 8—HuMab Hybridoma Generation

HuMab mice with sufficient antigen-specific titer development (defined as above) were sacrificed and the spleen and lymph nodes flanking the abdominal aorta and vena cava were collected. Fusion of splenocytes and lymph node cells to a mouse myeloma cell line was done by electrofusion using a CEEF 50 Electrofusion System (Cyto Pulse Sciences, Glen Burnie, Md., USA), essentially according to the manufacturer's instructions. Next, the primary wells were sub cloned using the ClonePix system (Genetix, Hampshire, UK). To this end specific primary well hybridoma's were seeded in semisolid medium made from 40% CloneMedia (Genetix, Hampshire, UK) and 60% HyQ 2× complete media (Hyclone, Waltham, USA). The sub clones were retested in the antigen-specific binding assay as described in Example 7 and IgG levels were measured using an Octet (Fortebio, Menlo Park, USA) in order to select the most specific and best producing clone per primary well for further expansion. Further expansion and culturing of the resulting HuMab hybridomas were done based upon standard protocols (e.g. as described in Coligan J. E., Bierer, B. E., Margulies, D. H., Shevach, E. M. and Strober, W., eds. Current Protocols in Immunology, John Wiley & Sons, Inc., 2006). Clones derived by this process were designated PC1014.

Example 9—Mass Spectrometry of Purified Antibodies

Small aliquots of 0.8 mL antibody containing supernatant from 6-well or Hyperflask stage were purified using PhyTip columns containing Protein G resin (PhyNexus Inc., San Jose, USA) on a Sciclone ALH 3000 workstation (Caliper Lifesciences, Hopkinton, USA). The PhyTip columns were used according to manufacturer's instructions, although buffers were replaced by: Binding Buffer PBS (B.Braun, Medical B. V., Oss, Netherlands) and Elution Buffer 0.1M Glycine-HCl pH 2.7 (Fluka Riedel-de Haën, Buchs, Germany). After purification, samples were neutralized with 2M Tris-HCl, pH 9.0 (Sigma-Aldrich, Zwijndrecht, Netherlands). Alternatively, in some cases larger volumes of culture supernatant were purified using MabSelect SuRe.

After purification, the samples were placed in a 384-well plate (Waters, 100 µl square well plate, part#186002631). Samples were deglycosylated overnight at 37° C. with N-glycosidase F (Roche cat no 11365177001. DTT (15 mg/mL) was added (1 µL/well) and incubated for 1 h at 37° C. Samples (5 or 6 µL) were desalted on an Acquity UPLC™ (Waters, Milford, USA) with a BEH300 C18, 1.7 µm, 2.1×50 mm column at 60° C. MQ water and LC-MS grade acetonitrile (Biosolve, cat no 01204101, Valkenswaard, The Netherlands) with both 0.1% formic acid (Fluka, cat no 56302, Buchs, Germany), were used as Eluens A and B, respectively. Time-of-flight electrospray ionization mass spectra were recorded on-line on a micrOTOF™ mass spectrometer (Bruker, Bremen, Germany) operating in the positive ion mode. Prior to analysis, a 900-3000 m/z scale was calibrated with ES tuning mix (Agilent Technologies, Santa Clara, USA). Mass spectra were deconvoluted with DataAnalysis™ software v. 3.4 (Bruker) using the Maximal Entropy algorithm searching for molecular weights between 5 and 80 kDa.

After deconvolution, the resulting heavy and light chain masses for all samples were compared in order to find duplicate antibodies. This was sometimes due to the presence of an extra light chain, but in the comparison of the heavy chains, the possible presence of C-terminal lysine variants was also taken into account. This resulted in a list of unique antibodies, i.e., a unique combination of specific heavy and light chains. In case duplicate antibodies were found, one unique antibody was selected based on results from other tests.

Example 10—Sequence Analysis of the HER2 Antibody Variable Domains and Cloning in Expression Vectors Total RNA of the HER2 HuMabs was prepared from 5×10⁶ hybridoma cells and 5'-RACE-Complementary DNA (cDNA) was prepared from 100 ng total RNA, using the SMART RACE cDNA Amplification kit (Clontech), according to the manufacturer's instructions. VH and VL coding regions were amplified by PCR and cloned directly, in frame, in the pG1f and pKappa expression vectors, by ligation independent cloning (Aslanidis, C. and P. J. de Jong, Nucleic Acids Res 1990; 18(20): 6069-74). Clones derived by this process were designated TH1014. For each antibody, 16 VL clones and 8 VH clones were sequenced. Clones which predicted heavy and light chain mass in agreement with the mass of the hybridoma derived material of the same antibody (as determined by mass spectrometry) were selected for further study and expression.

The resulting sequences are shown in FIGS. 1 and 2 and in the Sequence Listing. Selected sequences are also described in more detail below. CDR sequences were defined according to IMGT (Lefranc M P. et al., Nucleic Acids Research, 27, 209-212, 1999 and Brochet X. Nucl. Acids Res. 36, W503-508 (2008)). Table 1, Table 2 and Table 3 give an overview of antibody sequence information or germline sequences, and Table 4 shows consensus sequences.

TABLE 1

Heavy chain variable region (VH), light chain variable region (VL) and CDR sequences of HuMabs 005, 006, 059, 060, 106, and 111.

| SEQ ID No: | Region | Sequence |
|---|---|---|
| SEQ ID No: 1 | VH 005 | EVQLVQSGAEVKKPGESLKISCKASGYSFHFYWIGW VRQMPGKGLEWMGSIYPGDSDTRYRPSFQGQVTISA DKSISTAYLQWTSLKASDTAIYYCARQRGDYYYFYGM DVWGQGTTVTVSS |
| SEQ ID No: 2 | VH 005, CDR1 | GYSFHFYW |
| SEQ ID No: 3 | VH 005, CDR2 | IYPGDSDT |
| SEQ ID No: 4 | VH 005, CDR3 | ARQRGDYYYFYGMDV |
| SEQ ID No: 5 | VL 005 | EIVLTQSPGTLSLSPGERATLSCRASQSVSSSYLAWY QQKPGQVPRLLIYGASSRATGIPDRFSGSGSGTDFTL TISRLEPEDFAVYYCQQYGSS-LTFGGGTKVEIK |
| SEQ ID No: 6 | VL 005, CDR1<br>VL 005, CDR2 | QSVSSSY<br>GAS |
| SEQ ID No: 7 | VL 005, CDR3 | QQYGSSLT |
| SEQ ID No: 8 | VH 006 | EVQLLESGGGLVQPGGSLRLSCAASGFTFSNYALIWV RQAPGKGLEWVSIIRGGAGSTYYADSVKGRFTISRD NSKNTLYLQMNSLRAEDTAVYYCAKARIWGPLFDYW GQGTLVTVSS |
| SEQ ID No: 9 | VH 006, CDR1 | GFTFSNYA |
| SEQ ID No: 10 | VH 006, CDR2 | IRGGAGST |
| SEQ ID No: 11 | VH 006, CDR3 | AKARIWGPLFDY |
| SEQ ID No: 12 | VL 006 | EIVLTQSPATLSLSPGERATLSCRASQSVSSYLAWYQ QKPGQAPRLLIYDASNRATGIPARFSGSGSGTDFTLTI SSLEPEDFAVYYCQQRSNWPPLTFGGGTKVEIK |
| SEQ ID No: 13 | VL 006, CDR1<br>VL 006, CDR2 | QSVSSY<br>DAS |
| SEQ ID No: 14 | VL 006, CDR3 | QQRSNWPPLT |
| SEQ ID No: 15 | VH 059 | QVQLVQSGAEVKKPGASVRVPCKASGYTFTRYGISW VRQAPGQGLEWMGWISAYNGKTYYAQKLQGRVTMT TDTSTSTAYMELRSLRSDDTAVYYCARSPLLWFEELY FDYWGQGTLVTVSS |
| SEQ ID No: 16 | VH 059, CDR1 | GYTFTRYG |
| SEQ ID No: 17 | VH 059, CDR2 | ISAYNGKT |
| SEQ ID No: 18 | VH 059, CDR3 | ARSPLLWFEELYFDY |

TABLE 1-continued

Heavy chain variable region (VH), light chain variable region (VL) and CDR sequences of HuMabs 005, 006, 059, 060, 106, and 111.

| | | |
|---|---|---|
| SEQ ID No: 19 | VL 059 | EIVLTQSPGTLSLSPGERATLSCRASQSVSSTYLAWY QQKPGQAPRLLIYGASSRATGIPDRFSGSGSGTDFTL TISRLEPEDFAVYYCQQYGTSLFTFGPGTKVDIK |
| SEQ ID No: 20 | VL 059, CDR1<br>VL 059, CDR2 | QSVSSTY<br>GAS |
| SEQ ID No: 21 | VL 059, CDR3 | QQYGTSLFT |
| SEQ ID No: 22 | VH 060 | EVQLVQSGAEVKKPGESLKISCKGSGYRFTSYWIGW VRQMPGKGLEWMGSIYPGDSYTRNSPSFQGQVTISA DKSIATAYLQWNSLKASDTAMYYCARHAGDFYYFDG LDVWGQGTTVTVSS |
| SEQ ID No: 23 | VH 060, CDR1 | GYRFTTSYW |
| SEQ ID No: 24 | VH 060, CDR2 | IYPGDSYT |
| SEQ ID No: 25 | VH 060, CDR3 | ARHAGDFYYFDGLDV |
| SEQ ID No: 26 | VL 060 | EIVLTQSPGTLSLSPGERATLSCRASQSVSSSYLAWY QQKPGQAPRLLIYGASSRATGIPDRFSGSGSGTDFTL TISRLEPEDFAVYYCQQYGSSPPITFGQGTRLEIK |
| SEQ ID No: 27 | VL 060, CDR1<br>VL 060, CDR2 | QSVSSSY<br>GAS |
| SEQ ID No: 28 | VL 060, CDR3 | QQYGSSPPIT |
| SEQ ID No: 29 | VH 106 | EVQLVQSGAEVKKPGESLKISCKGSGYSFTRYWIGW VRQMPGKGLEWMGIIYPGDSDTRYSPSFQGQVTISA DKSISTAYLQWSSLKASDTAMYYCARLTGDRGFDYY SGMDVWGQGTTVTVSS |
| SEQ ID No: 30 | VH 106, CDR1 | GYSFTRYW |
| SEQ ID No: 31 | VH 106, CDR2 | IYPGDSDT |
| SEQ ID No: 32 | VH 106, CDR3 | ARLTGDRGFDYYSGMDV |
| SEQ ID No: 33 | VL 106 | EIVLTQSPGTLSLSPGERATLSCRASQSVSSSYLAWY QQKPGQAPRLLIYGASSRATGIPDRFSGSGSGTDFTL TISRLEPEDFAVYYCQQYGSS-FTFGPGTKVDIK |
| SEQ ID No: 34 | VL 106, CDR1<br>VL 106, CDR2 | QSVSSSY<br>GAS |
| SEQ ID No: 35 | VL 106, CDR3 | QQYGSSFT |
| SEQ ID No: 36 | VH 111 | QVQLVQSGAEVKKPGSSVKVSCKASGGTFSSYGISW VRQAPGPGLEWMGRIIPILGIANYAQKFQGRVTITAD KSTNTAYMELSSLRSEDTAVYYCARDQEYSSNWYYW GQGTLVTVSS |
| SEQ ID No: 37 | VH 111, CDR1 | GGTFSSYG |
| SEQ ID No: 38 | VH 111, CDR2 | IIPILGIA |
| SEQ ID No: 39 | VH 111, CDR3 | ARDQEYSSNWYY |
| SEQ ID No: 40 | VL 111 | EIVLTQSPGTLSLSPGERATLSCRASQSVRSSYLAWY QQKPGQAPRLLIYGASSRATGIPDRFSGSGSGTDFTL TISRLEPEDFAVYYCQLYGSSPTFGPGTKVDIK |
| SEQ ID No: 41 | VL 111, CDR1<br>VL 111, CDR2 | QSVRSSY<br>GAS |
| SEQ ID No: 42 | VL 111, CDR3 | QLYGSSPT |

TABLE 2

Mouse origin and heavy and light chain sequence homologies of HuMabs 005, 006, 059, 060, 106, and 111.

| HuMab: | Mouse: | Strain: | Germline VH: | Germline VL: |
|---|---|---|---|---|
| 005 | 350611 | HCo12-BalbC | IgHV5-51-1 | IgKV3-20-01 |
| 006 | 350611 | HCo12-BalbC | IgHV3-23-1 | IgKV3-11-01 |
| 059 | 350654 | HCo17 | IgHV1-18-1 | IgKV3-20-01 |
| 060 | 350654 | HCo17 | IgHV5-51-1 | IgKV3-20-01 |
| 106 | 350660 | HCo17 | IgHV5-51-1 | IgKV3-20-01 |
| 111 | 350660 | HCo17 | IgHV1-69-4 | IgKV3-20-01 |

TABLE 3

Heavy chain variable region (VH), light chain variable region (VL) sequences of HuMabs 041, 150, 067, 072, 163, 093, and 044. The respective CDRs correspond to those underlined in FIGS. 1 and 2, for VH and VL sequences, respectively.

```
SEQ ID No: 43 VH 041 EVQLVQSGAEVKKPGESLKISCKGSGYSFTSYWIGWVRQMPGKGL
                    EWMGSIYPGDSHTRYRPSFQGQVTISADKSISTAYLQWSSLKASD
                    TAMYYCARQKGDFYYFFGLDVWGQGTAITVSS

SEQ ID No: 44 VL 041 EIVLTQSPGTLSLSPGERATLSCRASQSVSSSYLAWYQQKPGQAPR
                    LLIYGASSRATGIPDRFSGSGSGTDFTLTISRLEPEDFAVYYCQQYG
                    SSLTFGGGTKVEIK

SEQ ID No: 45 VH 150 EVQLVQSGAEVKKPGESLKISCKGSGYSFTSYWIGWVRQMPGKGL
                    EWMGSIYPGDSHTRYRPSFQGQVTISADKSISTAYLQWSSLKASD
                    TAMYYCARQAGDYYYYNGMDVWGQGTTVTVSS

SEQ ID No: 46 VL 150 EIVLTQSPGTLSLSPGERATLSCRASQSVSSSYLTWYQQKPGQAPR
                    LLIYGASSRATGIPDRFSGSGSGTDFTLTISRLEPEDFAVYYCQQYG
                    SSLTFGGGTKVEIK

SEQ ID No: 47 VH 067 EVQLVQSGAEVKKPGESLKISCKGSGYSFTSYWIGWVRQMPGKGL
                    EWMGIIYPGDSDTRYSPSFQGQVTISVDKSISTAYLQWSSLKASDT
                    AMYYCARQKGDYYYHYGLDVWGQGTTVTVSS

SEQ ID No: 48 VL 067 EIVLTQSPGTLSLSPGERATLSCRASQSVSSSYLAWYQQKPGQAPR
                    LLIYGASSRATGIPDRFSGSGSGTDFTLTISRLEPEDFAVYYCQQYG
                    SSPRLTFGGGTKVEIK

SEQ ID No: 49 VH 072 EVQLVQSGAEVKKPGESLKISCKGSGYSFTSYWIGWVRQMPGKGL
                    EWMGIIYPGDSDTRYSPSFQGQVTISADKSISTAYLQWSSLKASDT
                    AMYYCARQKGDYYYFNGLDVWGQGTTVTVSS

SEQ ID No: 50 VL 072 EIVLTQSPGTLSLSPGERATLSCRASQSVSSSYLAWYQQKPGQAPR
                    LLIYGASSRATGIPDRFSGSGSGTDFTLTISRLEPEDFAVYYCQQYG
                    SSPRLTFGGGTKVEIK

SEQ ID No: 51 VH 163 EVQLVQSGAEVKKPGESLKISCQGSGYRFISYWIGWVRQMPGKGL
                    EWMGRIYPGDSDTRYSPSFQGQVTISVDKSISTAYLQWSSLKASD
                    TAMYYCARQRGDYYYFNGLDVWGQGTTVTVSS

SEQ ID No: 52 VL 163 EIVLTQSPGTLSLSPGERATLSCRASQSVSSSYLAWYQQKPGQAPR
                    LLIYGASSRATGIPDRFSGSGSGTDFTLTISRLEPEDFAVYYCQQYG
                    SSLTFGGGTKVEIK

SEQ ID No: 53 VH 093 EVQLVQSGAEVKKPGESLKISCKGSGYSFTSYWIGWVRQMPGKGL
                    EWMGRIYPGDSDTRYSPSFQGQVTISADKSITTAYLQWSSLRASDT
                    AMYYCARQRGDYYYFFGLDIWGQGTTVTVSL

SEQ ID No: 54 VL 093 EIVLTQSPGTLSLSPGERATLSCRASQSVSSSYLAWYQQKPGQAPR
                    LLIYGASSRATGIPDRFSGSGSGTDFTLTISRLEPEDFAVYYCQQYG
                    SSLTFGGGTKVEIK

SEQ ID No: 55 VH 044 EVQLVQSGAEVKKPGESLKISCKGSGYRFSSYWIGWVRQMPGKGL
                    EWMGSIFPGDSDTRYSPSFQGQVTISADKSITTAYLQWSSLKASDT
                    AMYYCARQAGDYYYYNGMDVWGQGTTVTVSS

SEQ ID No: 56 VL 044 EIVLTQSPGTLSLSPGERATLSCRASQSVSSSYLAWYQQKPGQAPR
                    LLIYGASSRATGIPDRFSGSGSGTDFTLTISRLEPEDFAVYYCQQYG
                    SSLTFGGGTKVEIK
```

TABLE 4

Consensus CDRs based on sequence alignments shown in FIGS. 1 and 2.

| SEQ ID No: 57<br>005-060-106-041-<br>150-067-072-163-<br>093-044 | IgHV5-<br>51-1 | VH<br>CDR1 | GYX1FX2X3YW | wherein X1 = S or R;<br>X2 = S, T, H, or I; and<br>X3 = S, R, or F;<br>preferably, wherein<br>X2 = H or T |
|---|---|---|---|---|
| SEQ ID No: 58<br>005-060-106-041-<br>150-067-072-163-<br>093-044 | IgHV5-<br>51-1 | VH<br>CDR2 | IX1PGDSX2T | wherein X1 = Y or F;<br>X2 = D, Y, or H<br>preferably, wherein<br>X2 = D or Y |
| SEQ ID No: 59<br>005-060-106-041-<br>150-067-072-163-<br>093-044 | IgHV5-<br>51-1 | VH<br>CDR3 | ARX1X2X3X4X5X<br>6X7X8YX9X10GX<br>11DX12 | wherein X1 = Q, H, or L;<br>X2 = R, A, T, or K;<br>X3 = G; X4 = D; X5 = R or<br>none; X6 = G or none;<br>X7 = Y or F; X8 = Y or D;<br>X9 = Y, F, or H; X10 = Y,<br>D, S, F, or N; X11 = M or<br>L; and X12 = V or I;<br>preferably, wherein<br>X1 = Q, X2 = R or A;<br>X5 = X6 = none; X7 = Y or<br>F; X8 = Y; X9 = F; X10 = Y;<br>and X12 = V |
| SEQ ID No: 60<br>006 | IgHV3-<br>23-1 | VH<br>CDR1 | GFTFSXYA | wherein X = N or S,<br>preferably N |
| SEQ ID No: 61<br>006 | IgHV3-<br>23-1 | VH<br>CDR2 | IX1GX2X3GST | wherein X1 = R or S;<br>X2 = G or S; and X3 = A<br>or G, preferably wherein<br>X1 = R; X2 = G; and X3 = A |
| SEQ ID No: 62<br>006 | IgHV3-<br>23-1 | VH<br>CDR3 | AKRIWGPXFDY | wherein X = L or Y,<br>preferably L |
| SEQ ID No: 63<br>059 | IgHV1-<br>18-1 | VH<br>CDR1 | GYTFTXYG | wherein X = R or S,<br>preferably R |
| SEQ ID No: 64<br>059 | IgHV1-<br>18-1 | VH<br>CDR2 | ISAYNGXT | wherein X = K or N,<br>preferably K |
| SEQ ID No: 65<br>059 | IgHV1-<br>18-1 | VH<br>CDR3 | ARSPLLWFEELYF<br>DY | |
| SEQ ID No:66<br>111 | IgHV1-<br>69-4 | VH<br>CDR1 | GGTFSSYX | wherein X = G or A,<br>preferably G |
| SEQ ID No: 38<br>111 | IgHV1-<br>69-4 | VH<br>CDR2 | IIPILGIA | |
| SEQ ID No: 67<br>111 | IgHV1-<br>69-4 | VH<br>CDR3 | ARDQEYSSX1X2<br>X3 | wherein X1 = N or Y;<br>X2 = W or F; and X3 = Y<br>or D, preferably wherein<br>X1 = N; X2 = W; and<br>X3 = Y |
| SEQ ID No: 68<br>005-059-060-106-<br>111-041-150-067-<br>072-163-093-044 | IgKV3-<br>20-01 | VL<br>CDR1 | QSVX1SX2Y | wherein X1 = S or R and<br>X2 = S or T |
| 005-059-060-106-<br>111-041-150-067-<br>072-163-093-044 | IgKV3-<br>20-01 | VL<br>CDR2 | GAS | |
| SEQ ID No: 69<br>005-059-060-106-<br>111-041-150-067-<br>072-163-093-044 | IgKV3-<br>20-01 | VL<br>CDR3 | QX1YGX2SX3X4<br>X5T | wherein X1 = Q or L;<br>X2 = S or T; X3 = P or<br>none; X4 = P, L, R, or<br>none; and X5 = L, F, I, or<br>none;<br>preferably, wherein<br>X4 = P, L, or none |
| SEQ ID No: 13<br>006 | IgKV3-<br>11-01 | VL<br>CDR1 | QSVSSY | |
| 006 | IgKV3- | VL | DAS | |

TABLE 4-continued

Consensus CDRs based on sequence alignments shown in FIGS. 1 and 2.

| | | 11-01 CDR2 | |
|---|---|---|---|
| SEQ ID No: 14 | IgKV3- | VL | QQRSNWPPLT |
| 006 | | 11-01 CDR3 | |

Example 11—Purification of Antibodies

Culture supernatant was filtered over 0.2 µm dead-end filters, loaded on 5 ml MabSelect SuRe columns (GE Health Care) and eluted with 0.1 M sodium citrate-NaOH, pH 3. The eluate was immediately neutralized with 2M Tris-HCl, pH 9 and dialyzed overnight to 12.6 mM NaH2PO4, 140 mM NaCl, pH 7.4 (B.Braun). Alternatively, subsequent to purification, the eluate was loaded on a HiPrep Desalting column and the antibody was exchanged into 12.6 mM NaH2PO4, 140 mM NaCl, pH 7.4 (B.Braun) buffer. After dialysis or exchange of buffer, samples were sterile filtered over 0.2 µm dead-end filters. Purity was determined by SDS-PAGE and concentration was measured by nephelometry and absorbance at 280 nm. Purified antibodies were stored at 4° C. Mass spectrometry was performed to identify the molecular mass of the antibody heavy and light chains expressed by the hybridomas as described in Example 9.

Example 12—Binding of HER2 Clones to Tumor Cells Expressing Membrane-Bound HER2 Measured by Means of FACS Analysis The binding of HER2 antibodies to AU565 cells (purchased at ATCC, CRL-2351) and A431 cells (purchased at ATCC, CRL-1555), was tested using flow cytometry (FACS Canto II, BD Biosciences). Qifi analysis (Dako, Glostrup, Denmark) revealed that the AU565 cells expressed on average 1,000,000 copies of HER2 protein per cell, whereas A431 cells expressed on average 15,000 copies per cell. Binding of HER2 antibodies was detected using a Phycoerythrin (PE)-conjugated goat-anti-human IgG antibody (Jackson). Clinical grade Herceptin® (Roche) was used as a positive control, and an isotype control antibody was used as negative control. $EC_{50}$ values were determined by means of non-linear regression (sigmoidal dose-response with variable slope) using GraphPad Prism V4.03 software (GraphPad Software, San Diego, Calif., USA).

Figure 3B:
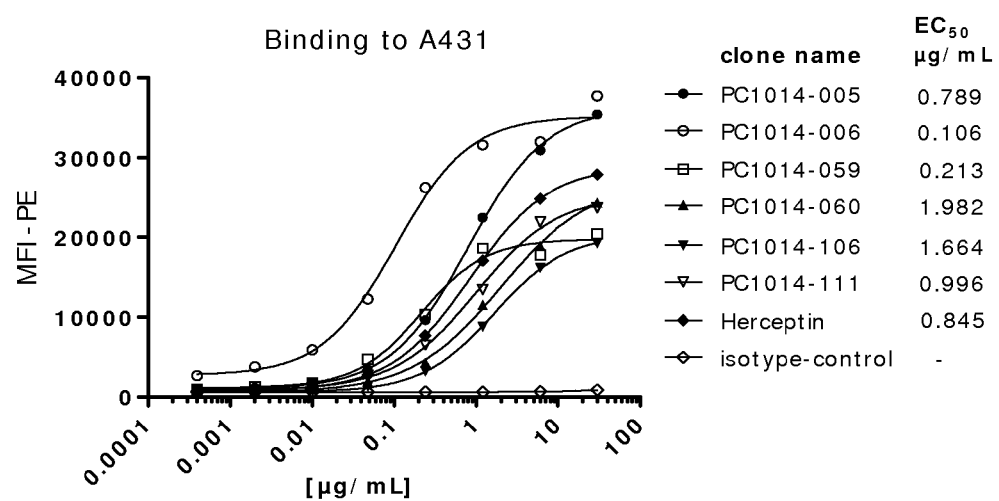

As shown in FIG. 3, all tested HER2 antibodies bound to HER2 expressed on both AU565 and A431 cells in a dose-dependent manner. The $EC_{50}$ values for binding varied between 0.304-2.678 µg/mL for AU565 cells and 0.106-1.982 µg/mL for A431 cells. Especially on A431 cells, large differences in $EC_{50}$ values were observed between the tested antibodies. Some differences in maximum binding levels were also observed between different antibodies. In particular, antibodies 005 and 006 demonstrated higher maximum binding levels on A431 as compared to other HER2 antibodies.

Example 13—Binding of HER2 Antibodies to Membrane-Bound HER2 Expressed on Rhesus Epithelial Cells Measured by Means of FACS Analysis To determine cross-reactivity with Rhesus HER2, the binding of HER2 antibodies to HER2-positive Rhesus epithelial cells (4MBr-5; purchased at ATCC) was tested using flow cytometry (FACS Canto II, BD Biosciences). A Phycoerythrin-conjugated goat-anti-human IgG antibody (Jackson) was used as a secondary conjugate. An isotype control antibody was used as negative control antibody.

Figure 4:
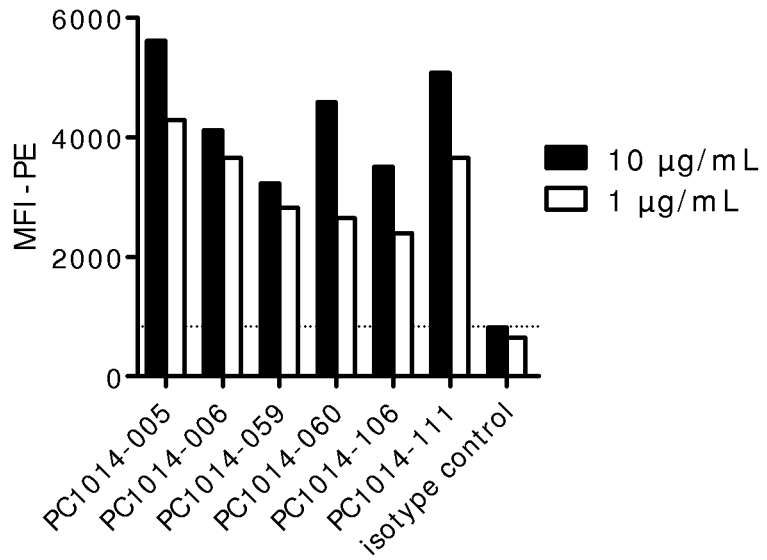
FIG. 4: Binding of HER2 antibodies to HER2 expressed on Rhesus epithelial cells. Data shown are mean fluorescence intensities (MFI) of one experiment, described in Example 13.

As shown in FIG. 4, all tested HER2 antibodies were cross-reactive with Rhesus monkey HER2. At both tested concentrations (1 µg/mL and 10 µg/mL), the HER2 antibodies were able to bind specifically to Rhesus monkey HER2. No binding was observed with the isotype control antibody.

Example 14—Competition of HER2 Antibodies for Binding to Soluble Her2ECDHis Measured in Sandwich-ELISA The optimal coating concentrations of the tested HER2 antibodies and optimal Her2ECDHis concentration were determined in the following manner: ELISA wells were coated overnight at 4° C. with HER2 HuMabs serially diluted in PBS (0.125-8 µg/mL in 2-fold dilutions). Next, the ELISA wells were washed with PBST (PBS supplemented with 0.05% Tween-20 [Sigma-Aldrich, Zwijndrecht, The Netherlands]) and blocked for one hour at room temperature (RT) with PBSTC (PBST supplemented 2% [v/v] chicken serum [Gibco, Paisley, Scotland]). The ELISA wells were then washed with PBST and incubated for one hour at RT with Her2ECDHis serially diluted in PBSTC (0.25-2 µg/mL in 2-fold dilutions). Unbound Her2ECDHis was washed away with PBST, and bound Her2ECDHis was incubated for one hour at RT with 0.25 µg/mL biotinylated rabbit-anti-6xhis-biot (Abcam, Cambridge, UK). The plate was thereafter washed with PBST and incubated for one hour with 0.1 µg/mL Streptavidin-poly-HRP (Sanquin, Amsterdam, The Netherlands) diluted in PBST. After washing, the reaction was visualized through a 15 minutes incubation with 2,2'-azino-bis (3-ethylbenzothiazoline-6-sulfonic acid (ABTS: one ABTS tablet diluted in 50 mL ABTS buffer (Roche Diagnostics, Almere, The Netherlands)) at RT (room temperature) protected from light. The colorization was stopped by adding an equal volume of oxalic acid (Sigma-Aldrich, Zwijndrecht, The Netherlands). Fluorescence at 405 nm was measured on a microtiter plate reader (Biotek Instruments, Winooski, USA). The antibody concentrations that resulted in sub-optimal binding of each antibody were determined and used for the following cross-block experiments.

Each HER2 antibody was coated to the ELISA wells at the sub-optimal dose that was determined as described above. After blocking of the ELISA wells, the wells were incubated with the predetermined concentration of 1 µg/mL biotinylated Her2ECDHis in the presence or absence of an excess of a second (competitor) HER2 antibody. The ELISA was then performed as described above. Residual binding of Her2ECDHis to the coated antibody was expressed as a percentage relative to the binding observed in the absence of competitor antibody. Percentage competition for each antibody combination was then determined as 100 minus the percentage of inhibition. 75% competition represented full block, with 25-74% competition representing partial block, and 0-24% competition no block.

As shown in Table 5, all HER2 antibodies competed for binding to Her2ECDHis, at least partially, with themselves. Trastuzumab (clinical grade Herceptin®) and pertuzumab (TH1014-pert, transiently produced in HEK-293 cells) could only compete with themselves, and not with any of the other listed HER2 antibodies. C1 and F5 (both transiently produced in HEK-293 cells) competed with each other for binding to Her2ECDHis, but did not compete with other HER2 antibodies.

Antibodies 005, 006, 059, 060, 106 and 111 all competed with each other for binding to Her2ECDHis, but did not cross-block with trastuzumab, pertuzumab, C1 or F5. Clones 005, 059, 060 and 106 only blocked 006 when 006 was the competitor antibody. In the reverse reaction where 006 was immobilized, no blocking was found with 005, 059, 060 or 106. This was possibly a result of the higher apparent affinity of clone 006 compared to 005, 059, 060, 106 and 111, shown in FIGS. 3A and 3B. Values higher than 100% can be explained by avidity effects and the formation of antibody-Her2ECDHis complexes containing two non-blocking antibodies.

TABLE 5

Competition and blocking of HER2 antibodies for binding to Her2ECDHis

| Immobilized mAb ↓ | Competing mAb: → | | | | | | | | | |
|---|---|---|---|---|---|---|---|---|---|---|
|  | Tras | Pert | C1 | F5 | 106 | 111 | 005 | 006 | 059 | 060 |
| Trastuzumab | 6 | 100 | 103 | 99 | 114 | 166 | 137 | 110 | 120 | 119 |
| TH1014-pert | 104 | 9 | 106 | 125 | 115 | 145 | 151 | 125 | 132 | 118 |
| TH1014-C1 | 89 | 85 | 65 | 58 | 84 | 86 | 98 | 99 | 89 | 93 |
| TH1014-F5 | 197 | 178 | 70 | 21 | 129 | 183 | 178 | 192 | 165 | 185 |
| PC1014-106 | 323 | 275 | 471 | 495 | 26 | 21 | 25 | 25 | 25 | 23 |
| PC1014-111 | 110 | 102 | 122 | 119 | 75 | 14 | 51 | 10 | 65 | 36 |
| PC1014-005 | 126 | 115 | 157 | 227 | 54 | 32 | 18 | 15 | 22 | 12 |
| PC1014-006 | 163 | 136 | 136 | 153 | 127 | 47 | 148 | 20 | 129 | 125 |
| PC1014-059 | 117 | 107 | 78 | 128 | 23 | 12 | 13 | 11 | 12 | 11 |
| PC1014-060 | 106 | 99 | 108 | 126 | 37 | 35 | 30 | 6 | 14 | 19 |
| Cross-block group | 1 | 2 | 3 | 3 | 4 | 4 | 4 | 4 | 4 | 4 |

Depicted values are mean percentages inhibition of binding relative to the binding observed in the absence of competitor antibody, of two independent experiments. Competition experiments with HEK-produced C1 and F5 (TH1014-C1 and TH1014-F5) were performed once. Trastuzumab (clinical grade Herceptin®) and HEK-produced pertuzumab (TH1014-pert) were also tested twice.

Example 15—Antibody-Dependent Cell-Mediated Cytotoxicity (ADCC)

SK-BR-3 cells (purchased at ATCC, HTB-30) were harvested ($5\times10^6$ cells), washed (twice in PBS, 1500 rpm, 5 min) and collected in 1 mL RPMI 1640 medium supplemented with 10% cosmic calf serum (CCS) (HyClone, Logan, Utah, USA), to which 200 µCi $^{51}$Cr (Chromium-51; Amersham Biosciences Europe GmbH, Roosendaal, The Netherlands) was added. The mixture was incubated in a shaking water bath for 1.5 hours at 37° C. After washing of the cells (twice in PBS, 1500 rpm, 5 min), the cells were resuspended in RPMI 1640 medium supplemented with 10% CCS, counted by trypan blue exclusion and diluted to a concentration of $1\times10^5$ cells/mL.

Meanwhile, peripheral blood mononuclear cells (PBMCs) were isolated from fresh buffy coats (Sanquin, Amsterdam, The Netherlands) using standard Ficoll density centrifugation according to the manufacturer's instructions (lymphocyte separation medium; Lonza, Verviers, France). After resuspension of cells in RPMI 1640 medium supplemented with 10% CCS, cells were counted by trypan blue exclusion and concentrated to $1\times10^7$ cells/mL.

For the ADCC experiment, 50 µL $^{51}$Cr-labeled SK-BR-3 cells (5.000 cells) were pre-incubated with 15 µg/mL HER2 antibody (IgG1,κ) in a total volume of 100 µL RPMI medium supplemented with 10% CCS in a 96-well microtiter plate. After 15 min at RT, 50 µL PBMCs (500.000 cells) were added, resulting in an effector to target ratio of 100:1. The maximum amount of cell lysis was determined by incubating 50 µL $^{51}$Cr-labeled SK-BR-3 cells (5.000 cells) with 100 µL 5% Triton-X100. The amount of spontaneous lysis was determined by incubating 5.000 $^{51}$Cr-labeled SK-BR-3 cells in 150 µL medium, without any antibody or effector cells. The level of antibody-independent cell lysis was determined by incubating 5.000 SK-BR-3 cells with 500.000 PBMCs without antibody. Subsequently, the cells were incubated 4 hr at 37° C., 5% CO2. To determine the amount of cell lysis, the cells were centrifuged (1200 rpm, 3 min) and 75 µL of supernatant was transferred to micronic tubes, after which the released $^{51}$Cr was counted using a gamma counter. The measured counts per minute (cpm) were used to calculate the percentage of antibody-mediated lysis as follows:

(cpm sample−cpm Ab-independent lysis)/(cpm max-lysis−cpm spontaneous lysis)×100%

Figure 5:
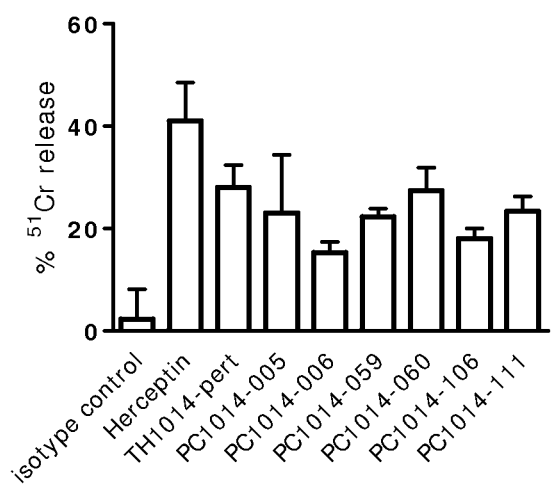
FIG. 5: Chromium-release (ADCC) assay of HER2 antibodies, showing PBMC-mediated lysis of $^{51}Cr$-labeled SK-BR-3 cells after incubation with HER2 antibody. Values depicted are the mean maximum percentages $^{51}Cr$-release±the standard deviation from one representative in vitro ADCC experiment with SK-BR-3 cells. See Example 15 for details.

As shown in FIG. 5, all HER2 antibodies induced efficient lysis of SK-BR-3 cells through ADCC. The average percentage lysis by the different antibodies varied between 15% and 28%, except for trastuzumab (Herceptin®), which showed on average 41% lysis. Without being bound by theory, the higher percentage lysis by trastuzumab possibly resulted from an increased non-core fucosylation grade (12.4%) due to its CHO production, compared to ~4% non-core fucosylation on the other HEK-produced HER2 antibodies, or by recognizing an epitope that induces less internalization of the HER2 receptor-antibody complexes.

Example 16—Inhibition of Ligand-Independent Proliferation of AU565 Cells

HER2 antibodies were tested for their ability to inhibit proliferation of AU565 cells in vitro. Due to the high HER2 expression levels on AU565 cells (~1.000.000 copies per cell as described in Example 12), HER2 is constitutively active in these cells and thus not dependent on ligand-induced heterodimerization.

In a 96-well tissue culture plate (Greiner bio-one, Frickenhausen, Germany). 9.000 AU565 cells were seeded per well in the presence of 10 µg/mL HER2 antibody in serum-free cell culture medium. As a control, cells were seeded in serum-free medium without antibody. After 3 days, the amount of viable cells was quantified with Alamarblue (BioSource International, San Francisco, US) according to the manufacturer's instructions. Fluorescence was monitored using the EnVision 2101 Multilabel reader (PerkinElmer, Turku, Finland) with standard Alamarblue settings. The Alamarblue signal of antibody-treated cells was plotted as a percentage relative to untreated cells. Dunnett's test was applied for statistical analysis.

Figure 6:
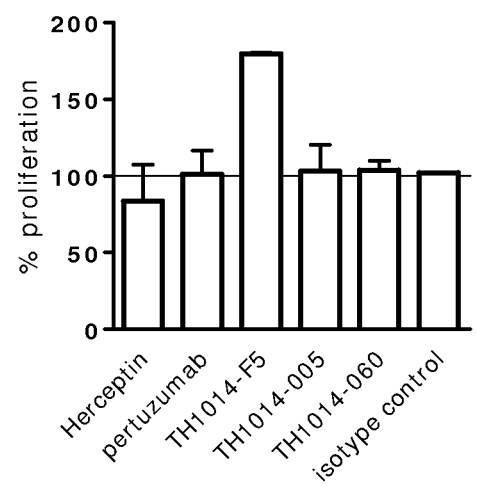
FIG. 6: Effect of HER2 antibodies on the proliferation of AU565 cells, as compared to untreated cells (set to 100%). Data shown are percentages proliferation of AU565 cells compared to untreated cells measured in three independent experiments±the standard deviation. See Example 16 for details.

The results are depicted in FIG. 6, showing the percentage proliferation of AU565 cells after HER2 antibody treatment compared to untreated cells, which was set to 100%. Herceptin apparently inhibited AU565 cell proliferation, but this effect was not statistically significant. TH1014-F5 significantly enhanced proliferation of AU565 cells indicating that this is an agonistic antibody, whereas none of the other antibodies tested (005, 060 and pertuzumab) had a substantial effect on AU565 proliferation. For trastuzumab (Herceptin®) and pertuzumab, this was in accordance with the results described by Juntilla et al. (Cancer Cell 2009; 15(5): 353-355).

TABLE 6

Average percentage proliferation of AU565 cells after HER2 antibody treatment compared to untreated cells, which was set to 100%.

| antibody | % proliferation |
| --- | --- |
| PC1014-005 | 103 |
| PC1014-060 | 104 |
| TH1014-F5 | 180 |
| TH1014-pert | 101 |
| Herceptin | 83 |
| isotype-control | 101 |

Example 17—Anti-Kappa-ETA' Assay

To investigate the suitability of HER2 antibodies for an antibody-drug conjugate approach, a generic in vitro cell-based killing assay using kappa-directed pseudomonas-exotoxin A (anti-kappa-ETA') was developed. The assay makes use of a high affinity anti-kappa domain antibody conjugated to a truncated form of the pseudomonas-exotoxin A. Upon internalization, the anti-kappa-ETA' domain antibody undergoes proteolysis and disulfide-bond reduction, separating the catalytic from the binding domain. The catalytic domain is transported from the Golgi to the endoplasmic reticulum via the KDEL retention motif, and subsequently translocated to the cytosol where it inhibits protein synthesis and induces apoptosis (Kreitman R J, BioDrugs 2009; 23(1):1-13). In this assay, to identify HER2 antibodies that enable internalization and killing through the toxin, HER2 antibodies are preconjugated with the anti-kappa-ETA' before incubation with HER2-positive cells. As noted above, AU565 cells express a high number of Her2 molecules per cell (~$10^6$ molecules/cell), whereas A431 cells express a low number of Her2 molecules per cell (~30,000 molecules/cell).

First, the optimal concentration of anti-kappa-ETA' was determined for each cell line, i.e. the maximally tolerate dose that does not lead to induction of non-specific cell death. AU565 cells (7500 cells/well) and A431 cells (2500 cells/well) were seeded in normal cell culture medium in 96-wells tissue culture plate (Greiner bio-one) and allowed to adhere for at least 4 hours. Next, cells were incubated with 100, 10, 1, 0.1, 0.01, 0.001 and 0 µg/mL anti-kappa-ETA' dilutions in normal cell culture medium. After 3 days, the amount of viable cells was quantified with Alamarblue (BioSource International, San Francisco, US) according to the manufacturer's instruction. Fluorescence was monitored using the EnVision 2101 Multilabel reader (PerkinElmer, Turku, Finland) with standard Alamarblue settings. The highest concentration anti-kappa-ETA' that did not kill the cells by itself was used for following experiments (0.5 µg/mL for AU565 and 1 µg/mL for A431).

Next, antibody-mediated internalization and killing by the toxin was tested for different HER2 antibodies. Cells were seeded as described above. Dilution-series of HER2 antibodies were pre-incubated for 30 minutes with the predetermined concentration anti-kappa-ETA' before adding them to the cells. After 3 days of incubation, the amount of viable cells was quantified as described above. The Alamarblue signal of cells treated with anti-kappa-ETA' conjugated antibodies was plotted compared to cells treated with antibody alone. 23.4 µg/mL Staurosporin was used as positive control for cell killing. An isotype control antibody was used as negative control.

Figure 7A:
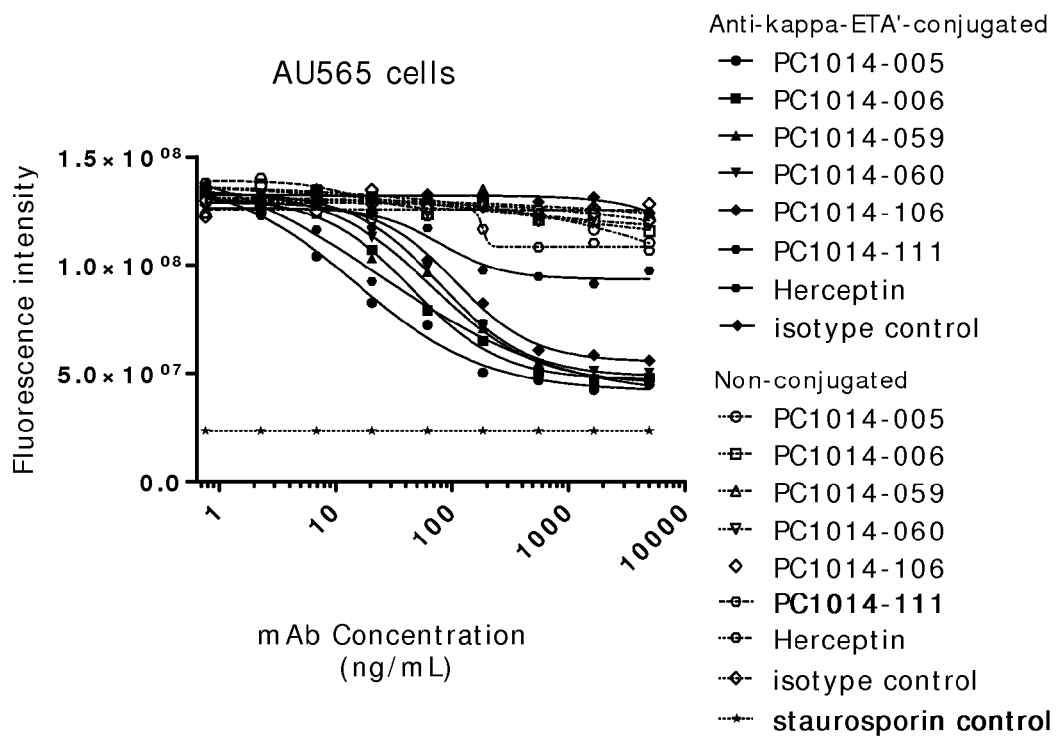
FIGS. 7A-7B: ADC assay, showing killing of AU565 cells (FIG. 7A) or A431 cells (FIG. 7B) via anti-kappa-ETA'-conjugated HER2 antibodies.

As shown in FIG. 7A and Table 7, all anti-kappa-ETA'-conjugated HER2 antibodies were able to kill AU565 cells in a dose-dependent manner. Anti-kappa-ETA'-conjugated-Herceptin killed only 32% of the AU565 cells, whereas all other conjugated antibodies induced 50-72% cell killing. Moreover, antibodies 005 and 111 demonstrated more than three times improved $EC_{50}$ values (resp. 15.13 and 24.20 ng/mL) compared to trastuzumab (78.49 ng/mL). Except for trastuzumab, non-conjugated HER2 antibodies did not induce killing of AU565 cells at the concentrations tested.

TABLE 7

Killing of AU565 cells by anti-kappa-ETA'-conjugated HER2 antibodies. Data shown are $EC_{50}$ values and maximal percentage cell kill of AU565 cells treated with anti-kappa-ETA'-conjugated HER2 antibodies, measured in one representative experiment. Cell kill induced by Staurosporin was set as 100% and MFI of untreated cells was set as 0%.

| antibody | % cells killed | EC50 ng/mL |
| --- | --- | --- |
| PC1014-111 | 72.0 | 24.2 |
| PC1014-005 | 69.7 | 15.13 |
| PC1014-059 | 67.0 | 67.65 |
| PC1014-060 | 64.3 | 79.38 |
| PC1014-106 | 59.1 | 107.9 |
| PC1014-006 | 50.4 | 45.14 |
| Trastuzumab | 31.9 | 78.49 |
| isotype control | Ndet | Ndet |

"Ndet" means not detected.

Figure 7B:
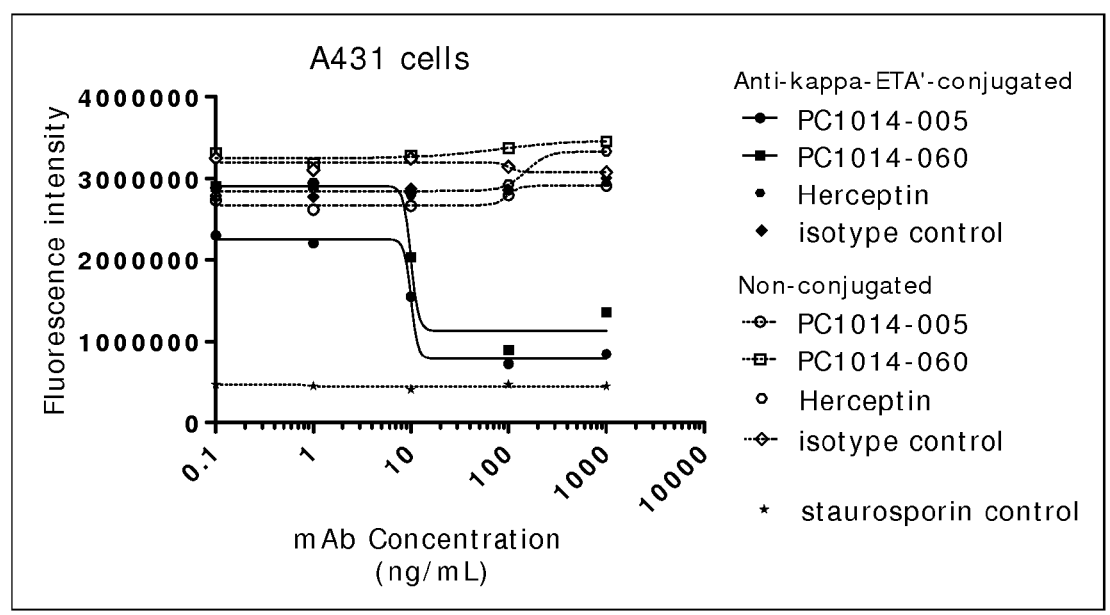

As shown in FIG. 7B and Table 8, antibodies 005 and 060 were able to induce effective killing of A431 cells (≥85%) when conjugated to anti-kappa-ETA', whereas anti-kappa-ETA'-conjugated-Herceptin and isotype control antibody did not induce killing of A431 cells. Moreover, antibodies 005 and 111 demonstrated killing of A431 cells already at low antibody concentrations (10 ng/mL) with $EC_{50}$ values of ~10 ng/mL. No cell kill was observed with non-conjugated HER2 antibodies.

TABLE 8

Killing of A431 cells by anti-kappa-ETA'-conjugated HER2 antibodies. Data shown are $EC_{50}$ values and maximal percentage cell kill of A431 cells treated with anti-kappa-ETA'-conjugated HER2 antibodies, measured in one representative experiment. Cell kill induced by Staurosporin was set as 100% and MFI of untreated cells was set as 0%.

| antibody | % cells killed | EC50 ng/mL |
| --- | --- | --- |
| PC1014-005 | 88.5 | ~10.07 |
| PC1014-060 | 85.0 | ~10.03 |
| Trastuzumab | NDet | NDet |
| isotype control | NDet | NDet |

Example 18—Internalization of HER2 Antibodies Measured with an FMAT-Based Fab-CypHer5E Assay To investigate whether the enhanced killing of AU565 cells observed in the kappa-toxin-ETA' assay described in the previous Example correlated with enhanced internalization of HER2 antibodies, a fab-CypHer5E-based internalization assay was performed. CypHer5E is a pH-sensitive dye which is non-fluorescent at basic pH (extracellular: culture medium) and fluorescent at acidic pH (intracellular: lysosomes), with an acid dissociation constant (pKa) of 7.3.

AU565 cells were seeded in a 384-wells tissue culture plates (Greiner bio-one), at a density of 3000 cells/well in normal cell culture medium supplemented with 240 ng/mL fab-CypHer5E (in house conjugation of Goat-fab-anti-Human IgG [Jackson] with CypHer5E [GE Healthcare, Eindhoven, The Netherlands] according to manufacturer's instructions). Next, HER2 antibodies were serially diluted in normal cell culture medium, added to the cells and left at room temperature for 9 hours. Mean fluorescent intensities (MFI) of intracellular CypHer5E were measured using the 8200 FMAT (Applied Biosystems, Nieuwerkerk A/D IJssel, The Netherlands) and 'counts×fluorescence' was used as read-out. An isotype control antibody was used as negative control antibody. $EC_{50}$ values and maximal MFI were determined by means of non-linear regression (sigmoidal dose-response with variable slope) using GraphPad Prism V4.03 software (GraphPad Software, San Diego, Calif., USA).

The results are shown in Table 9, depicting the $EC_{50}$ values and maximal MFI for all tested HER2 antibodies in the CypHer5E internalization assay with AU565 cells. The maximal MFI values reflect how many HER2 antibodies were internalized upon binding. All human HER2 antibodies showed higher maximal MFI values (130.529-57.428) than trastuzumab (35.000) and TH1014-pert (35.323), indicating that these antibodies induced enhanced receptor internalization. The enhanced internalization of TH1014-F5 may be a result from its agonistic activity and the induction of HER2-HER2 dimerization (see Example 16).

TABLE 9

Cypher-5-based internalization assay of HER2 antibodies. Data shown are MFI and $EC_{50}$ values of one representative experiment from two experiments with AU565 cells treated with fab-CypHer5E labeled HER2 antibodies.
Cypher 5

| Antibody | $EC_{50}$ ng/mL | Maximal MFI |
|---|---|---|
| PC1014-006 | 23.08 | 130829 |
| PC1014-005 | 21.37 | 95117 |
| PC1014-111 | 35.22 | 81680 |
| PC1014-059 | 14.77 | 77123 |
| PC1014-060 | 36.16 | 68184 |
| PC1014-106 | 68.60 | 57428 |
| TH1014-F5 | 22.65 | 113116 |
| TH1014-pert | ~1041 | 35323 |
| Trastuzumab | 21.70 | 35000 |

Example 19—HER2 Downmodulation

To investigate if enhanced HER2 internalization induced by the antibodies of the present invention also results in enhanced receptor downmodulation, 005 was selected as representative antibody and tested for its ability to induce downmodulation of HER2. To this end, AU565 cells were incubated 3 days with HER2 antibodies, and analyzed for presence of HER2. AU565 cells were seeded in a 24-wells tissue culture plate (100.000 cells/well) in normal cell culture medium and cultured for 3 days at 37° C. in the presence of 10 μg/mL HER2 antibody. After washing with PBS, cells were lysed by incubating 30 min at room temperature with 25 μL Surefire Lysis buffer (Perkin Elmer, Turku, Finland). Total protein levels were quantified using bicinchoninic acid (BCA) protein assay reagent (Pierce) according to the manufacturer's protocol. HER2 protein levels in the lysates were analyzed using a HER2-specific sandwich ELISA. Rabbit-anti-human HER2 intracellular domain antibody (Cell Signaling) was used to capture HER2 and biotinylated goat-anti-human HER2 polyclonal antibody (R&D), followed by streptavidin-poly-HRP, were used to detect bound HER2. The reaction was visualized using 2,2'-azino-bis 3-ethylbenzothiazoline-6-sulfonic acid (ABTS: dilute one ABTS tablet in 50 mL ABTS buffer [Roche Diagnostics, Almere, The Netherlands]) and stopped with oxalic acid (Sigma-Aldrich, Zwijndrecht, The Netherlands). Fluorescence at 405 nm was measured on a microtiter plate reader (Biotek Instruments, Winooski, USA) and the amount of HER2 was expressed as a percentage relative to untreated cells.

Figure 8:
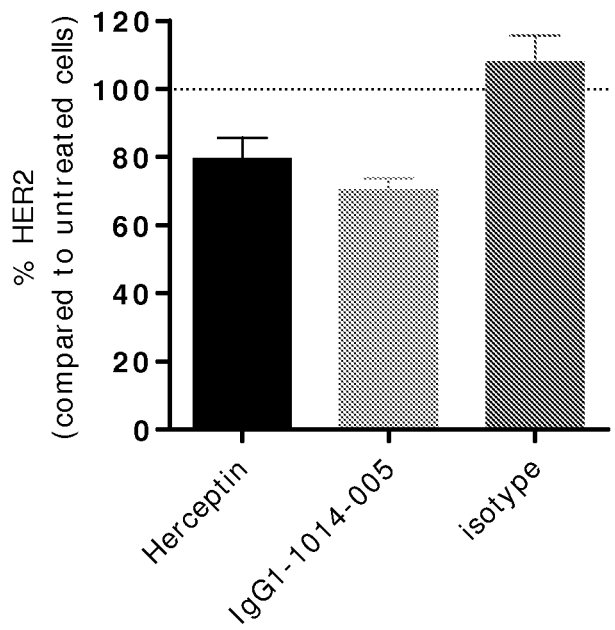
FIG. 8: Antibody induced downmodulation of HER2. Relative percentage of HER2 expressed in AU565 cell lysate after 3 days incubation with 10 µg/mL antibody. The amount of HER2 was quantified using a HER2-specific capture ELISA and plotted as a percentage relative to untreated cells. Data shown are mean of three experiments±standard deviation. See example 19 for details.

The results are shown in FIG. 8 and Table 10 below depicting the amount of HER2 expressed as a percentage compared to untreated cells. The results in FIG. 8 and Table 10 demonstrate that antibody 005 induced approximately 30% HER2 downmodulation, while Herceptin induced approximately 20% HER2 downmodulation. This was in line with enhanced internalization observed by antibody 005.

TABLE 10

Antibody induced downmodulation of HER2 depicted as percentage HER2 compared to untreated cells

| antibody | % HER2 compared to untreated cells |
|---|---|
| Herceptin | 80 |
| IgG1-1014-005 | 70 |
| isotype control | 108 |

Example 20—Colocalization of HER2 Antibodies with Lysosomal Marker LAMP1 Analyzed by Confocal Microscopy The HER2 downmodulation assay as described in example 19 and the CypHer-5E based internalization assay indicated that HER2 antibodies of the present invention were more efficiently internalized and targeted towards lysosomes. To confirm these findings, confocal microscopy technology was applied. AU565 cells were grown on glass coverslips (thickness 1.5 micron, Thermo Fisher Scientific, Braunschweig, Germany) in standard tissue culture medium at 37° C. for 3 days. Cells were pre-incubated for 1 hour with 50 μg/mL leupeptin (Sigma) to block lysosomal activity, after which 10 ug/mL HER2 antibody were added. The cells were incubated for an additional 3 or 18 hours at 37° C. Hereafter they were washed with PBS and incubated for 30 min. at RT (room temperature) with 4% formaldehyde (Klinipath). Slides were washed with blocking buffer (PBS supplemented with 0.1% saponin [Roche] and 2% BSA [Roche]) and incubated for 20 min with blocking buffer containing 20 mM $NH_4Cl$ to quench formaldehyde. Slides were washed again with blocking buffer and incubated for 45 min at RT with mouse-anti-human CD107a (LAMP1) (BD Pharmingen) to identify lysosomes. Following washing with blocking buffer the slides were incubated 30 min at RT with a cocktail of secondary antibodies; goat-anti-mouse IgG-Cy5 (Jackson) and goat-anti-human IgG-FITC (Jackson). Slides were washed again with blocking buffer and mounted on microscope slides using 20 μL mounting medium (6 gram Glycerol [Sigma] and 2.4 gram Mowiol 4-88 [Omnilabo] was dissolved in 6 mL distilled water to which 12 mL 0.2M Tris [Sigma] pH8.5 was added followed by incubation for 10 min at 50-60° C. Mounting medium was aliquoted and stored at −20° C.). Slides were imaged with a Leica SPE-II confocal microscope (Leica Microsystems) equipped with a 63× 1.32-0.6 oil immersion objective lens and LAS-AF software. To allow for quantification of overlapping pixel intensities, laser intensity, gain and offset were adjusted to visualize antibodies without pixel saturation. These settings were kept the same for all confocal slides.

12-bit grayscale TIFF images were analyzed for colocalisation using MetaMorph software (version Meta Series 6.1, Molecular Devices Inc, Sunnyvale Calif., USA). FITC and Cy5 images were imported as stacks and background was subtracted. Identical thresholds settings were used (manually set) for all FITC images and all Cy5 images. Colocalisation was depicted as the pixel intensity of FITC in the region of overlap (ROI), were the ROI is composed of all Cy5 positive regions. To compare different slides stained with several HER2 antibodies, the images were normalized using the pixel intensity of Cy5. Goat-anti-mouse IgG-Cy5 was used to stain the lysosomal marker LAMP1 (CD107a). The pixel intensity of LAMP1 should not differ between various HER2 antibodies tested.

$$\text{Normalized values for colocalization of } FITC \text{ and } Cy5 = \frac{\left(\begin{array}{c}\text{Total Pixel Intensity } FITC \times \\ \text{percentage } FITC\text{-}Cy5 \text{ colocalization}/100\end{array}\right)}{\text{Total Pixel Intensity } Cy5}$$

Figure 9:
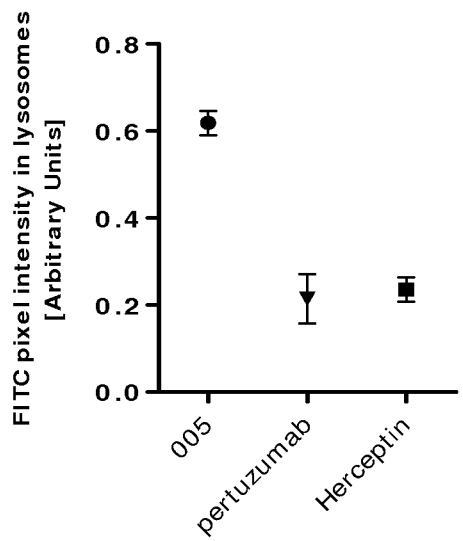
FIG. 9: Colocalization analysis of HER2 antibodies (FITC) with lysosomal marker LAMP1 (Cy5), showing FITC pixel intensity overlapping with Cy5 for various monospecific HER2 antibodies. FITC pixel intensity in LAMP1/Cy5 positive pixels of three different images is plotted for each antibody. Antibody 005 shows higher FITC pixel intensities in the LAMP1/Cy5 positive compartments compared to antibodies Herceptin and pertuzumab. See example 20 for details.

The results are shown in FIG. 9 and Table 11 below, and depict the FITC pixel intensity overlapping with Cy5 for various HER2 antibodies. For each antibody, three different images were analyzed from one slide containing ~1, 3 or >5 cells. Significant variation was observed between the different images within each slide. Still, it was evident that antibody 005 demonstrated increased colocalisation with the lysosomal marker LAMP1, when compared with Herceptin and pertuzumab. These results indicate that once internalized, HER2 antibody 005 is efficiently sorted towards lysosomal compartments, making it especially interesting for an antibody drug conjugate approach.

TABLE 11

Mean FITC pixel intensities overlapping with Cy5 depicted as arbitrary units

| antibody | FITC pixel intensity in lysosomes [arbitrary units] |
|---|---|
| TH1014-005 | 0.619 |
| TH1014-pert | 0.214 |
| Herceptin | 0.236 |

Example 21—HER2 Extracellular Domain Shuffle Human-to-Chicken

To further define the HER2 binding regions recognized by antibodies of the present invention, a HER2 extracellular domain shuffle experiment was performed. To this end, a small gene-synthesis library with five constructs was generated, swapping the sequences of domain I, II, III or IV of the extracellular domain of human HER2 to the corresponding sequence of chicken HER2 (*Gallus gallus* isoform B NCBI: NP 001038126.1): 1) fully human HER2 (Uniprot P04626) hereafter named hu-HER2, 2) hu-HER2 with chicken domain I (replacing amino acids (aa) 1-203 of the human Her2 with the corresponding chicken Her2 region) hereafter named hu-HER2-ch(I), 3) hu-HER2 with chicken domain II (replacing amino acids (aa) 204-330 of the human Her2 with the corresponding chicken Her2 region) hereafter named hu-HER2-ch(II), 4) hu-HER2 with chicken domain III (replacing aa 331-507 of the human Her2 with the corresponding chicken Her2 region) hereafter named hu-HER2-ch(III) and 5) hu-HER2 with chicken domain IV (replacing aa 508-651 of the human Her2 with the corresponding chicken Her2 region) hereafter named hu-HER2-ch(IV). The human and chicken HER2 orthologs show 67% homology in their extracellular domain with 62% homology in domain I, 72% homology in domain II, 63% homology in domain III and 68% homology in domain IV. The constructs were transiently transfected in the Freestyle™ CHO-S (Invitrogen) cell line using Freestyle MAX transfection reagent (Invitrogen) according to the instructions of the manufacturer, and transfected cells were cultured for 20 hours. HER2 antibody binding to the transfected cells was analyzed by means of flow cytometry:

The transfected CHO-S cells were harvested, washed with FACS buffer and incubated with 10 μg/mL HER2 antibody (30 minutes on ice). Binding of HER2 antibodies was detected using a Phycoerythrin (PE)-conjugated goat-anti-human IgG antibody (Jackson). To check if expression between different batches was the same, cells were fixed and permeabilized using Cytofix/Cytoperm solution (BD) according manufacturer's instruction and stained with a rabbit-anti-human intracellular HER2 antibody (DAKO) in combination with a secondary PE-conjugated goat-anti-rabbit antibody (Jackson). An isotype control antibody was used as negative control. Fluorescence was measured on a FACSCanto-II (BD) and binding curves were made by means of non-linear regression (sigmoidal dose-response with variable slope) using GraphPad Prism V4.03 software (GraphPad Software, San Diego, Calif., USA). Loss of binding was used as read out to identify which HER2 domains were recognized by the different antibodies.

Figure 10:
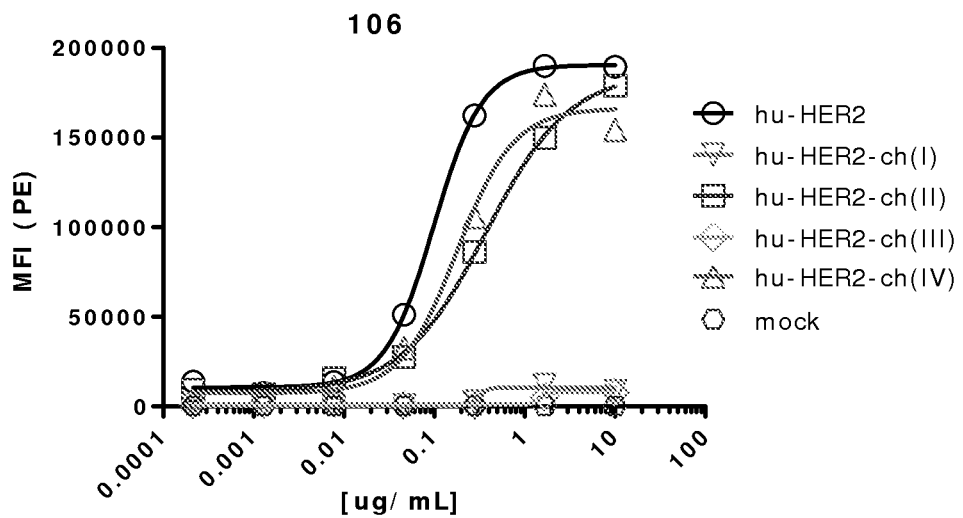
FIG. 10: HER2 antibody binding to CHO-S cells transfected with different HER2 ECD construct analyzed by means of flow cytometry. Hu-HER2=fully human HER2, Hu-HER2-ch(I) CR1=hu-HER2 with chicken domain I, Hu-HER2-ch(II)=hu-HER2 with chicken domain II, hu-HER2-ch(III)=hu-HER2 with chicken domain III and Hu-HER2-ch(IV)=hu-HER2 with chicken domain IV. Data shown are mean fluorescence intensities (MFI) of one representative antibody, 106. See example 21 for details.

Exemplary binding curves for antibody 106 are shown in FIG. 10. All binding results are shown in Table 12. Herceptin showed loss of binding to Hu-HER2-ch(IV), but not to the proteins with one of the remaining domains shuffled, confirming that the epitopes of Herceptin resides in HER2 domain IV. Pertuzumab showed only loss of binding to Hu-HER2-ch(II), confirming that its epitope resides in HER2 domain II. Antibodies 005, 006, 060 and 111 showed loss of binding upon substitution of HER2 domain III, which demonstrated that the epitope resides in HER2 domain III. Interestingly, antibodies 059 and 106 demonstrated loss of binding to both hu-HER2-ch(III) and hu-HER2-ch(I), implying that antibodies 059 and 106 recognize a conformational epitope within these two domains.

TABLE 12

Summary of HER2 antibody binding to different HER2ECD receptor constructs. FL; hu-HER2, I; hu-HER2-ch(I), II; hu-HER2-ch(II), III; hu-HER2-ch(III), IV; hu-HER2-ch(IV).

| Antibody | HER2-domain shuffled | | | | |
|---|---|---|---|---|---|
| | FL | I | II | III | IV |
| Herceptin | +++ | +++ | +++ | +++ | − |

TABLE 12-continued

Summary of HER2 antibody binding to different HER2ECD receptor constructs. FL; hu-HER2, I; hu-HER2-ch(I), II; hu-HER2-ch(II), III; hu-HER2-ch(III), IV; hu-HER2-ch(IV).

| Antibody | HER2-domain shuffled | | | | |
|---|---|---|---|---|---|
| | FL | I | II | III | IV |
| Pertuzumab | +++ | +++ | + | +++ | +++ |
| 005 | +++ | +++ | +++ | − | +++ |
| 006 | +++ | +++ | +++ | − | +++ |
| 059 | +++ | − | +++ | − | +++ |
| 060 | +++ | +++ | +++ | − | +++ |
| 106 | +++ | − | +++ | − | +++ |
| 111 | +++ | +++ | +++ | − | +++ |

+++ indicates normal binding, + indicates reduced binding compared to binding observed to hu-HER2, − indicates no binding detected.

Example 22—In Vivo Efficacy of HER2 HuMab 005 in NCI-N87 Human Gastric Carcinoma Xenografts in SCID Mice The in vivo effect of HER2-HuMab 005 on tumor growth and survival in a NCI-N87 human gastric carcinoma xenograft model in female CB.17 severe combined immunodeficiency (SCID) mice was determined. $10 \times 10^6$ NCI-N87 tumor cells in 50% matrigel were injected s.c. in female SCID mice, 10 mice per group. Eight days after tumor inoculation, intravenous treatment with HER2-HuMabs 005 or control antibody HuMab-HepC was started. In FIG. 11 this is indicated as day 1, day of treatment initiation. The first dose was at 40 mg/kg, followed by 10 mg/kg on days 4, 8, 11, 15, 18, 22 and 25 after treatment initiation.

Tumor volume was determined at least 2 times per week. Volumes ($mm^3$) were calculated from caliper (PLEXX) measurements as $(width^2 \times length)/2$. Tumors were calipered twice weekly and each animal was euthanized when its tumor reached the predetermined endpoint volume (800 $mm^3$).

Figure 11A:
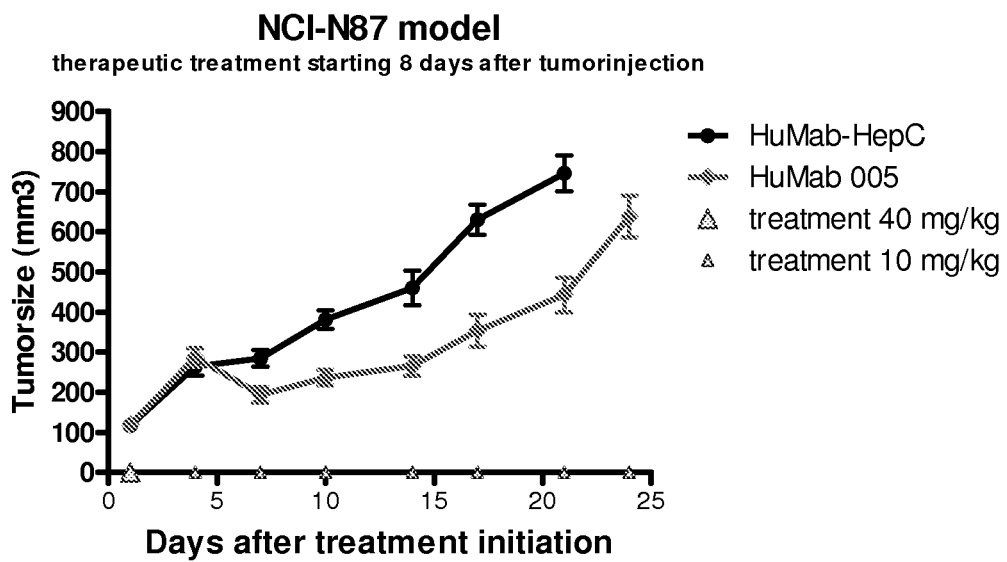
FIGS. 11A-11B: In vivo effect of HER2-HuMab 005 in the NCI-N87 human gastric carcinoma xenograft model in female CB.17 severe combined immunodeficiency (SCID) mice. Data shown are mean tumorsize±S.E.M. per group (n=10 mice per group) (FIG. 11A) and survival (FIG. 11B). See example 22 for details.
Figure 11B:
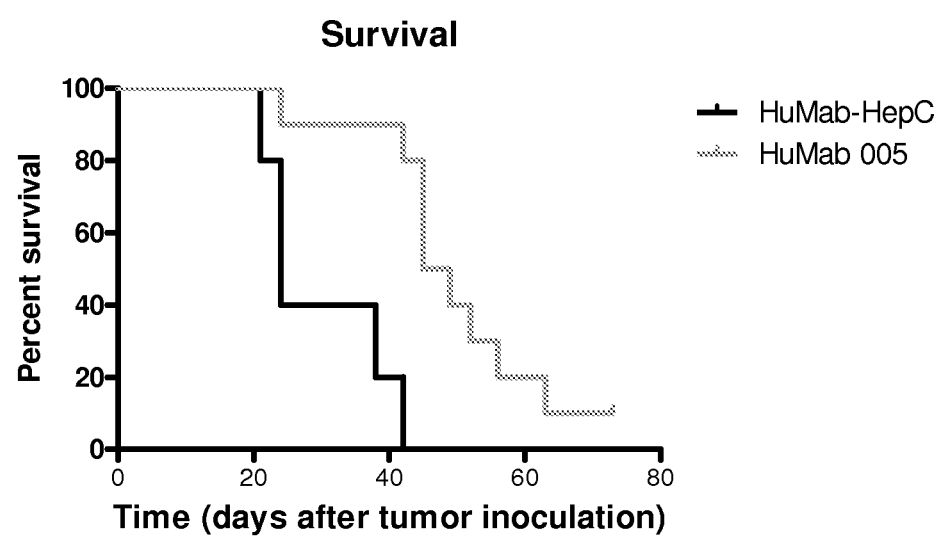

As shown in FIGS. 11A and 11B the mice administered with HuMab 005 demonstrated slower tumor growth (A) and better survival (B), respectively than the mice that received negative control antibody HuMab-HepC.

---

The invention claimed is:

1. An isolated antibody which binds to human epidermal growth factor receptor 2 (HER2), comprising a VH region and a VL region selected from the group consisting of:
   a) a VH region comprising the CDR1, CDR2 and CDR3 sequences of SEQ ID NOs:2, 3 and 4, respectively; and a VL region comprising the CDR1, CDR2 and CDR3 sequences of SEQ ID NO:6, GAS, and SEQ ID NO:7, respectively;
   b) a VH region comprising the CDR1, CDR2 and CDR3 sequences of SEQ ID NOs:9, 10 and 11, respectively; and a VL region comprising the CDR1, CDR2 and CDR3 sequences of SEQ ID NO:13, DAS, and SEQ ID NO:14, respectively;
   c) a VH region comprising the CDR1, CDR2 and CDR3 sequences of SEQ ID NOs:16, 17 and 18, respectively; and a VL region comprising the CDR1, CDR2 and CDR3 sequences of SEQ ID NO:20, GAS, and SEQ ID NO:21, respectively;
   d) a VH region comprising the CDR1, CDR2 and CDR3 sequences of SEQ ID NOs:23, 24 and 25, respectively; and a VL region comprising the CDR1, CDR2 and CDR3 sequences of SEQ ID NO:27, GAS, and SEQ ID NO:28, respectively;
   e) a VH region comprising the CDR1, CDR2 and CDR3 sequences of SEQ ID NOs:30, 31 and 32, respectively; and a VL region comprising the CDR1, CDR2 and CDR3 sequences of SEQ ID NO:34, GAS, and SEQ ID NO:35, respectively; and
   f) a VH region comprising the CDR1, CDR2 and CDR3 sequences of SEQ ID NOs:37, 38 and 39, respectively; and a VL region comprising the CDR1, CDR2 and CDR3 sequences of SEQ ID NO:41, GAS, and SEQ ID NO:42, respectively.

2. The antibody of claim 1, comprising a VH region and a VL region selected from the group consisting of:
   a) a VH region comprising the sequence of SEQ ID NO:1 and a VL region comprising the sequence of SEQ ID NO:5;
   b) a VH region comprising the sequence of SEQ ID NO:8 and a VL region comprising the sequence of SEQ ID NO:12;
   c) a VH region comprising the sequence of SEQ ID NO:15 and a VL region comprising the sequence of SEQ ID NO:19;
   d) a VH region comprising the sequence of SEQ ID NO:22 and a VL region comprising the sequence of SEQ ID NO:26;
   e) a VH region comprising the sequence of SEQ ID NO:29 and a VL region comprising the sequence of SEQ ID NO:33;
   f) a VH region comprising the sequence of SEQ ID NO:36 and a VL region comprising the sequence of SEQ ID NO:40; and
   g) a variant of any of said antibodies, wherein said variant has at most 1, 2 or 3 amino acid substitutions.

3. The antibody of claim 1, which has an $EC_{50}$ value for binding to HER2-expressing cells lower than 0.80 µg/ml, and blocks the binding to soluble HER2 of a reference antibody comprising VH and VL regions selected from the group consisting of:
   a) a VH region comprising the sequence of SEQ ID NO:1 and a VL region comprising the sequence of SEQ ID NO:5;
   b) a VH region comprising the sequence of SEQ ID NO:8 and a VL region comprising the sequence of SEQ ID NO:12; and
   c) a VH region comprising the sequence of SEQ ID NO:15 and a VL region comprising the sequence of SEQ ID NO:19.

4. The antibody of claim 1, which specifically binds HER2-positive Rhesus epithelial cells, and blocks the binding to soluble HER2 of a reference antibody comprising VH and VL regions selected from the group consisting of:
   a) a VH region comprising the sequence of SEQ ID NO:1 and a VL region comprising the sequence of SEQ ID NO:5;
   b) a VH region comprising the sequence of SEQ ID NO:8 and a VL region comprising the sequence of SEQ ID NO:12;
   c) a VH region comprising the sequence of SEQ ID NO:15 and a VL region comprising the sequence of SEQ ID NO:19;
   d) a VH region comprising the sequence of SEQ ID NO:22 and a VL region comprising the sequence of SEQ ID NO:26;
   e) a VH region comprising the sequence of SEQ ID NO:29 and a VL region comprising the sequence of SEQ ID NO:33; and
   f) a VH region comprising the sequence of SEQ ID NO:36 and a VL region comprising the sequence of SEQ ID NO:40.

5. The antibody of claim 1, which specifically binds HER2-expressing AU565 cells but promotes ligand-independent proliferation of the cells to a lesser extent than F5, and blocks the binding to soluble HER2 of a reference antibody comprising VH and VL regions selected from the group consisting of:
   a) a VH region comprising the sequence of SEQ ID NO:1 and a VL region comprising the sequence of SEQ ID NO:5; and
   b) a VH region comprising the sequence of SEQ ID NO:22 and a VL region comprising the sequence of SEQ ID NO:26.

6. The antibody of claim 1, wherein the antibody, when conjugated to a therapeutic moiety, which is a truncated form of the pseudomonas-exotoxin A, kills at least 60% of a HER2-expressing tumor cell-line, and blocks the binding to soluble HER2 of a reference antibody comprising the VH and VL regions selected from the groups consisting of:
   a) a VH region comprising the sequence of SEQ ID NO:1 and a VL region comprising the sequence of SEQ ID NO:5;
   b) an antibody comprising a VH region comprising the sequence of SEQ ID NO:22 and a VL region comprising the sequence of SEQ ID NO:26;
   c) a VH region comprising the sequence of SEQ ID NO:15 and a VL region comprising the sequence of SEQ ID NO:19; and
   d) a VH region comprising the sequence of SEQ ID NO:36 and a VL region comprising the sequence of SEQ ID NO:40.

7. The antibody of claim 6, wherein the HER2-expressing tumor cell-line expresses less than an average of about 30000 HER2 molecules per cell, and wherein the antibody blocks the binding to soluble HER2 of a reference antibody comprising the VH and VL regions selected from the group consisting of:
   a) a VH region comprising the sequence of SEQ ID NO:1 and a VL region comprising the sequence of SEQ ID NO:5; and
   b) an antibody comprising a VH region comprising the sequence of SEQ ID NO:22 and a VL region comprising the sequence of SEQ ID NO:26.

8. The antibody of claim 1, wherein a higher amount of the antibody is internalized by a HER2-expressing tumor cell-line than the amount of trastuzumab internalized by the same cell line, and wherein the antibody cross-blocks a reference antibody comprising VH and VL regions selected from the group consisting of:
   a) a VH region comprising the sequence of SEQ ID NO:1 and a VL region comprising the sequence of SEQ ID NO:5;
   b) a VH region comprising the sequence of SEQ ID NO:8 and a VL region comprising the sequence of SEQ ID NO:12;
   c) a VH region comprising the sequence of SEQ ID NO:15 and a VL region comprising the sequence of SEQ ID NO:19;
   d) a VH region comprising the sequence of SEQ ID NO:22 and a VL region comprising the sequence of SEQ ID NO:26;
   e) a VH region comprising the sequence of SEQ ID NO:29 and a VL region comprising the sequence of SEQ ID NO:33; and
   f) a VH region comprising the sequence of SEQ ID NO:36 and a VL region comprising the sequence of SEQ ID NO:40.

9. The antibody of claim 3, which fully blocks the reference antibody from binding to soluble HER2.

10. The antibody of claim 1, wherein the antibody is a bivalent antibody.

11. The antibody of claim 1, wherein the antibody is an antigen-binding fragment.

12. The antibody of claim 1, wherein the antibody is a full-length antibody.

13. The antibody of claim 1, wherein the antibody is an effector-function-deficient antibody.

14. The antibody of claim 1, wherein the antibody is a monovalent antibody.

15. The antibody of claim 14, wherein the monovalent antibody further comprises a $C_H$ region of an immunoglobulin or a fragment thereof comprising the $C_H2$ and $C_H3$ regions, wherein the $C_H$ region or fragment thereof has been modified such that the region corresponding to the hinge region and, if the immunoglobulin is not an IgG4 subtype, other regions of the $C_H$ region do not comprise any amino acid residues which are capable of forming disulfide bonds with an identical $C_H$ region or other covalent or stable non-covalent inter-heavy chain bonds with an identical $C_H$ region in the presence of polyclonal human IgG.

16. A bispecific antibody comprising a first antigen-binding region of an antibody as defined in claim 1, and a second antigen-binding region having a different binding specificity than the first antigen-binding region.

17. The antibody of claim 1, wherein the antibody is conjugated to another moiety.

18. The antibody of claim 17, wherein the moiety is a cytotoxic moiety is selected from the group consisting of taxol; cytochalasin B; gramicidin D; ethidium bromide; emetine; mitomycin; etoposide; tenoposide; vincristine; vinblastine; colchicin; doxorubicin; daunorubicin; dihydroxy anthracin dione; a tubulin-inhibitor; mitoxantrone; mithramycin; actinomycin D; 1-dehydrotestosterone; a glucocorticoid; procaine; tetracaine; lidocaine; propranolol; puromycin; calicheamicin or an analog or derivative thereof; an antimetabolite; an alkylating agent; an antibiotic; an antimitotic agent; diphtheria toxin; ricin toxin; cholera toxin; a Shiga-like toxin; LT toxin; C3 toxin; Shiga toxin; pertussis toxin; tetanus toxin; soybean Bowman-Birk protease inhibitor; Pseudomonas exotoxin; alorin; saporin; modeccin; gelanin; abrin A chain; modeccin A chain; alpha-sarcin; *Aleurites fordii* proteins; dianthin proteins; *Phytolacca americana* proteins; momordica charantia inhibitor; curcin; crotin; sapaonaria officinalis inhibitor; gelonin; mitogellin; restrictocin; phenomycin; enomycin toxins; ribonuclease (RNase); DNase I; Staphylococcal enterotoxin A; pokeweed antiviral protein; diphtherin toxin; and Pseudomonas endotoxin.

19. The antibody of claim 17, wherein the moiety is a cytotoxic moiety selected from the group consisting of maytansine, calicheamicin, duocarmycin, rachelmycin (CC-1065), monomethyl auristatin E, and an analog, derivative, or prodrug of any thereof.

20. The antibody of claim 17, which is conjugated to a cytokine selected from the group consisting of interleukin (IL)-2, IL-4, IL-6, IL-7, IL-10, IL-12, IL-13, IL-15, IL-18, IL-23, IL-24, IL-27, IL-28a, IL-28b, IL-29, keratinocyte growth factor, interferon (IFN)α, IFNβ, IFNγ, granulocyte-macrophage colony-stimulating factor, CD40L, Flt3 ligand, stem cell factor, ancestim, and tumor necrosis factor (TNF) α.

21. The antibody of claim 17, which is conjugated to a radioisotope.

22. A pharmaceutical composition comprising the antibody of claim 1 and a pharmaceutically acceptable carrier.

23. A pharmaceutical comprising an antibody as defined in claim 17, and a pharmaceutically acceptable carrier.

24. A method for inhibiting growth and/or proliferation of one or more tumor cells expressing HER2, comprising administration, to an individual in need thereof, of an antibody according to claim 1.

25. The method of claim 24, wherein the one or more tumor cell co-expresses HER2 and EGFR and/or HER3.

26. A method for treating cancer, comprising
a) selecting a subject suffering from a cancer comprising tumor cells co-expressing HER2 and EGFR and/or HER3, and
b) administering to the subject the antibody according to claim 1.

27. The method of claim 26, wherein the cancer is selected from the group consisting of breast cancer, colorectal cancer, endometrial/cervical cancer, lung cancer, malignant melanoma, ovarian cancer, pancreatic cancer, prostate cancer, testis cancer, a soft-tissue tumor, and bladder cancer.

28. A method for detecting the presence of HER2 in a sample, comprising:
contacting the sample with an antibody of claim 1 under conditions that allow for formation of a complex between the antibody and HER2; and
analyzing whether a complex has been formed.

29. A kit for detecting the presence of HER2 in a sample comprising an antibody of claim 1; and
instructions for use of the kit.

30. The antibody of claim 1, wherein the antibody comprises a VH region comprising the CDR1, CDR2 and CDR3 sequences of SEQ ID NOs:2, 3 and 4, respectively; and a VL region comprising the CDR1, CDR2 and CDR3 sequences of SEQ ID NO:6, GAS, and SEQ ID NO:7, respectively.

31. The antibody of claim 1, wherein the antibody comprises a VH region comprising the CDR1, CDR2 and CDR3 sequences of SEQ ID NOs:9, 10 and 11, respectively; and a VL region comprising the CDR1, CDR2 and CDR3 sequences of SEQ ID NO:13, DAS, and SEQ ID NO:14, respectively.

32. The antibody of claim 1, wherein the antibody comprises a VH region comprising the CDR1, CDR2 and CDR3 sequences of SEQ ID NOs:16, 17 and 18, respectively; and a VL region comprising the CDR1, CDR2 and CDR3 sequences of SEQ ID NO:20, GAS, and SEQ ID NO:21, respectively.

33. The antibody of claim 1, wherein the antibody comprises a VH region comprising the CDR1, CDR2 and CDR3 sequences of SEQ ID NOs:23, 24 and 25, respectively; and a VL region comprising the CDR1, CDR2 and CDR3 sequences of SEQ ID NO:27, GAS, and SEQ ID NO:28, respectively.

34. The antibody of claim 1, wherein the antibody comprises a VH region comprising the CDR1, CDR2 and CDR3 sequences of SEQ ID NOs:30, 31 and 32, respectively; and a VL region comprising the CDR1, CDR2 and CDR3 sequences of SEQ ID NO:34, GAS, and SEQ ID NO:35, respectively.

35. The antibody of claim 1, wherein the antibody comprises a VH region comprising the CDR1, CDR2 and CDR3 sequences of SEQ ID NOs:37, 38 and 39, respectively; and a VL region comprising the CDR1, CDR2 and CDR3 sequences of SEQ ID NO:41, GAS, and SEQ ID NO:42, respectively.

36. The bispecific antibody of claim 16, wherein the second antigen-binding site binds to a molecule selected from the group consisting of: a cancer- or tumor-associated antigen; a cancer-associated integrin; a T cell and/or NK cell antigen; an angiogenic factor, receptor for an angiogenic factor, or other cancer-associated growth factor; and a receptor associated with cancer progression.

37. The bispecific antibody of claim 36, wherein the cancer- or tumor-associated antigen is selected from the group consisting of: a carcinoembryonic antigen, prostate specific antigen, renal antigen, α-fetoprotein, CTL-recognized antigen on melanoma, a CT antigen, a mucin antigen, a ganglioside antigen, tyrosinase, gp75, c-Met, c-myc, Mart1, MelanA, MUM-1, MUM-2, MUM-3, HLA-B7, and Ep-CAM.

38. The bispecific antibody of claim 37, wherein:
a) the CT antigen is selected from the group consisting of: MAGE-B5, MAGE-B6, MAGE-C2, MAGE-C3, MAGE-D, Mage-12, CT10, NY-ESO-1, SSX-2, GAGE, BAGE, MAGE, and SAGE;
b) the mucin antigen is MUC1 or mucin-CA125;
c) the cancer-associated integrin is α5β3 integrin;
d) the T cell and/or NK cell antigen is CD3 or CD16;
e) the angiogenic factor or other cancer-associated growth factor is selected from the group consisting of vascular endothelial growth factor, fibroblast growth factor, epidermal growth factor, angiogenin, vascular endothelial growth factor receptor, fibroblast growth factor receptor, epidermal growth factor receptor, and angiogenin receptor; or
f) the receptor associated with cancer progression is selected from the group consisting of HER1, HER3, and HER4.

39. The bispecific antibody of claim 16, wherein the second antigen-binding region binds to a different site on HER2 than the first antigen-binding region.

40. The bispecific antibody of claim 39, wherein the second antigen-binding region cross-blocks the binding of trastuzumab, pertuzumab, F5, or C1 to HER2.

41. The antibody of claim 12, which is an IgG1 antibody.

42. The antibody of claim 41, which is an IgG1, κ antibody.

43. The antibody of claim 18, wherein
a) the tubulin-inhibitor is a maytansine or an analog or derivative thereof;
b) the antimetabolite is selected from the group consisting of methotrexate, 6 mercaptopurine, 6 thioguanine, cytarabine, fludarabin, 5 fluorouracil, decarbazine, hydroxyurea, asparaginase, gemcitabine, and cladribine;
c) the alkylating agent is selected from the group consisting of mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin, carboplatin, duocarmycin A, duocarmycin SA, rachelmycin (CC-1065), and an analog or derivative thereof;
d) the antibiotic is selected from the group consisting of: dactinomycin, bleomycin, daunorubicin, doxorubicin, idarubicin, mithramycin, mitomycin, mitoxantrone, plicamycin, and anthramycin (AMC));
e) the antimitotic agent is monomethyl auristatin E or F or an analog or derivative thereof;
f) the diphtheria toxin is diphtheria A chain or an active fragment thereof;
g) the ricin toxin is ricin A or a deglycosylated ricin A chain toxin;
h) the Shiga-like toxin is selected from the group consisting of: SLT I, SLT II, and SLT IIV; or
i) the *Phytolacca americana* protein is selected from the group consisting of: PAPI, PAPII, and PAP S.

* * * * *

SEQUENCE LISTING

```
<160> NUMBER OF SEQ ID NOS: 69

<210> SEQ ID NO 1
<211> LENGTH: 122
<212> TYPE: PRT
<213> ORGANISM: homo sapiens

<400> SEQUENCE: 1

Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Ser Phe His Phe Tyr
                20                  25                  30

Trp Ile Gly Trp Val Arg Gln Met Pro Gly Lys Gly Leu Glu Trp Met
            35                  40                  45

Gly Ser Ile Tyr Pro Gly Asp Ser Asp Thr Arg Tyr Arg Pro Ser Phe
        50                  55                  60

Gln Gly Gln Val Thr Ile Ser Ala Asp Lys Ser Ile Ser Thr Ala Tyr
65                  70                  75                  80

Leu Gln Trp Thr Ser Leu Lys Ala Ser Asp Thr Ala Ile Tyr Tyr Cys
                85                  90                  95

Ala Arg Gln Arg Gly Asp Tyr Tyr Phe Tyr Gly Met Asp Val Trp
                100                 105                 110

Gly Gln Gly Thr Thr Val Thr Val Ser Ser
        115                 120

<210> SEQ ID NO 2
<211> LENGTH: 8
<212> TYPE: PRT
<213> ORGANISM: homo sapiens

<400> SEQUENCE: 2

Gly Tyr Ser Phe His Phe Tyr Trp
1               5

<210> SEQ ID NO 3
<211> LENGTH: 8
<212> TYPE: PRT
```

```
<213> ORGANISM: homo sapiens

<400> SEQUENCE: 3

Ile Tyr Pro Gly Asp Ser Asp Thr
1               5

<210> SEQ ID NO 4
<211> LENGTH: 15
<212> TYPE: PRT
<213> ORGANISM: homo sapiens

<400> SEQUENCE: 4

Ala Arg Gln Arg Gly Asp Tyr Tyr Tyr Phe Tyr Gly Met Asp Val
1               5                   10                  15

<210> SEQ ID NO 5
<211> LENGTH: 107
<212> TYPE: PRT
<213> ORGANISM: homo sapiens

<400> SEQUENCE: 5

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Val Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
                100                 105

<210> SEQ ID NO 6
<211> LENGTH: 7
<212> TYPE: PRT
<213> ORGANISM: homo sapiens

<400> SEQUENCE: 6

Gln Ser Val Ser Ser Ser Tyr
1               5

<210> SEQ ID NO 7
<211> LENGTH: 8
<212> TYPE: PRT
<213> ORGANISM: homo sapiens

<400> SEQUENCE: 7

Gln Gln Tyr Gly Ser Ser Leu Thr
1               5

<210> SEQ ID NO 8
<211> LENGTH: 119
<212> TYPE: PRT
<213> ORGANISM: homo sapiens

<400> SEQUENCE: 8

Glu Val Gln Leu Leu Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Ser Asn Tyr
            20                  25                  30

Ala Leu Ile Trp Val Arg Gln Ala Pro Gly Lys Gly Leu Glu Trp Val
        35                  40                  45

Ser Ile Ile Arg Gly Gly Ala Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Arg Ile Trp Gly Pro Leu Phe Asp Tyr Trp Gly Gln Gly
            100                 105                 110

Thr Leu Val Thr Val Ser Ser
            115
```

<210> SEQ ID NO 9
<211> LENGTH: 8
<212> TYPE: PRT
<213> ORGANISM: homo sapiens

<400> SEQUENCE: 9

```
Gly Phe Thr Phe Ser Asn Tyr Ala
1               5
```

<210> SEQ ID NO 10
<211> LENGTH: 8
<212> TYPE: PRT
<213> ORGANISM: homo sapiens

<400> SEQUENCE: 10

```
Ile Arg Gly Gly Ala Gly Ser Thr
1               5
```

<210> SEQ ID NO 11
<211> LENGTH: 12
<212> TYPE: PRT
<213> ORGANISM: homo sapiens

<400> SEQUENCE: 11

```
Ala Lys Ala Arg Ile Trp Gly Pro Leu Phe Asp Tyr
1               5                   10
```

<210> SEQ ID NO 12
<211> LENGTH: 108
<212> TYPE: PRT
<213> ORGANISM: homo sapiens

<400> SEQUENCE: 12

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
```

```
                        85                  90                  95

Leu Thr Phe Gly Gly Gly Thr Lys Val Glu Ile Lys
            100                 105

<210> SEQ ID NO 13
<211> LENGTH: 6
<212> TYPE: PRT
<213> ORGANISM: homo sapiens

<400> SEQUENCE: 13

Gln Ser Val Ser Ser Tyr
1               5

<210> SEQ ID NO 14
<211> LENGTH: 10
<212> TYPE: PRT
<213> ORGANISM: homo sapiens

<400> SEQUENCE: 14

Gln Gln Arg Ser Asn Trp Pro Pro Leu Thr
1               5                   10

<210> SEQ ID NO 15
<211> LENGTH: 122
<212> TYPE: PRT
<213> ORGANISM: homo sapiens

<400> SEQUENCE: 15

Gln Val Gln Leu Val Gln Ser Gly Ala Glu Val Lys Lys Pro Gly Ala
1               5                   10                  15

Ser Val Arg Val Pro Cys Lys Ala Ser Gly Tyr Thr Phe Thr Arg Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Lys Thr Tyr Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Pro Leu Leu Trp Phe Glu Glu Leu Tyr Phe Asp Tyr Trp
            100                 105                 110

Gly Gln Gly Thr Leu Val Thr Val Ser Ser
        115                 120

<210> SEQ ID NO 16
<211> LENGTH: 8
<212> TYPE: PRT
<213> ORGANISM: homo sapiens

<400> SEQUENCE: 16

Gly Tyr Thr Phe Thr Arg Tyr Gly
1               5

<210> SEQ ID NO 17
<211> LENGTH: 8
<212> TYPE: PRT
<213> ORGANISM: homo sapiens

<400> SEQUENCE: 17

Ile Ser Ala Tyr Asn Gly Lys Thr
1               5
```

<210> SEQ ID NO 18
<211> LENGTH: 15
<212> TYPE: PRT
<213> ORGANISM: homo sapiens

<400> SEQUENCE: 18

Ala Arg Ser Pro Leu Leu Trp Phe Glu Glu Leu Tyr Phe Asp Tyr
1               5                   10                  15

<210> SEQ ID NO 19
<211> LENGTH: 108
<212> TYPE: PRT
<213> ORGANISM: homo sapiens

<400> SEQUENCE: 19

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Leu
                85                  90                  95

Phe Thr Phe Gly Pro Gly Thr Lys Val Asp Ile Lys
            100                 105

<210> SEQ ID NO 20
<211> LENGTH: 7
<212> TYPE: PRT
<213> ORGANISM: homo sapiens

<400> SEQUENCE: 20

Gln Ser Val Ser Ser Thr Tyr
1               5

<210> SEQ ID NO 21
<211> LENGTH: 9
<212> TYPE: PRT
<213> ORGANISM: homo sapiens

<400> SEQUENCE: 21

Gln Gln Tyr Gly Thr Ser Leu Phe Thr
1               5

<210> SEQ ID NO 22
<211> LENGTH: 122
<212> TYPE: PRT
<213> ORGANISM: homo sapiens

<400> SEQUENCE: 22

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Ser Tyr
            20                  25                  30

Trp Ile Gly Trp Val Arg Gln Met Pro Gly Lys Gly Leu Glu Trp Met

```
                35                  40                  45
Gly Ser Ile Tyr Pro Gly Asp Ser Tyr Thr Arg Asn Ser Pro Ser Phe
    50                  55                  60
Gln Gly Gln Val Thr Ile Ser Ala Asp Lys Ser Ile Ala Thr Ala Tyr
65                  70                  75                  80
Leu Gln Trp Asn Ser Leu Lys Ala Ser Asp Thr Ala Met Tyr Tyr Cys
                85                  90                  95
Ala Arg His Ala Gly Asp Phe Tyr Tyr Phe Asp Gly Leu Asp Val Trp
            100                 105                 110
Gly Gln Gly Thr Thr Val Thr Val Ser Ser
            115                 120
```

<210> SEQ ID NO 23
<211> LENGTH: 9
<212> TYPE: PRT
<213> ORGANISM: homo sapiens

<400> SEQUENCE: 23

```
Gly Tyr Arg Phe Thr Thr Ser Tyr Trp
1               5
```

<210> SEQ ID NO 24
<211> LENGTH: 8
<212> TYPE: PRT
<213> ORGANISM: homo sapiens

<400> SEQUENCE: 24

```
Ile Tyr Pro Gly Asp Ser Tyr Thr
1               5
```

<210> SEQ ID NO 25
<211> LENGTH: 15
<212> TYPE: PRT
<213> ORGANISM: homo sapiens

<400> SEQUENCE: 25

```
Ala Arg His Ala Gly Asp Phe Tyr Tyr Phe Asp Gly Leu Asp Val
1               5                   10                  15
```

<210> SEQ ID NO 26
<211> LENGTH: 109
<212> TYPE: PRT
<213> ORGANISM: homo sapiens

<400> SEQUENCE: 26

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Pro Ile Thr Phe Gly Gln Gly Thr Arg Leu Glu Ile Lys
            100                 105
```

-continued

<210> SEQ ID NO 27
<211> LENGTH: 7
<212> TYPE: PRT
<213> ORGANISM: homo sapiens

<400> SEQUENCE: 27

Gln Ser Val Ser Ser Ser Tyr
1               5

<210> SEQ ID NO 28
<211> LENGTH: 10
<212> TYPE: PRT
<213> ORGANISM: homo sapiens

<400> SEQUENCE: 28

Gln Gln Tyr Gly Ser Ser Pro Pro Ile Thr
1               5                  10

<210> SEQ ID NO 29
<211> LENGTH: 124
<212> TYPE: PRT
<213> ORGANISM: homo sapiens

<400> SEQUENCE: 29

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Arg Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Thr Gly Asp Arg Gly Phe Asp Tyr Tyr Ser Gly Met Asp
            100                 105                 110

Val Trp Gly Gln Gly Thr Thr Val Thr Val Ser Ser
        115                 120

<210> SEQ ID NO 30
<211> LENGTH: 8
<212> TYPE: PRT
<213> ORGANISM: homo sapiens

<400> SEQUENCE: 30

Gly Tyr Ser Phe Thr Arg Tyr Trp
1               5

<210> SEQ ID NO 31
<211> LENGTH: 8
<212> TYPE: PRT
<213> ORGANISM: homo sapiens

<400> SEQUENCE: 31

Ile Tyr Pro Gly Asp Ser Asp Thr
1               5

<210> SEQ ID NO 32
<211> LENGTH: 17

```
<212> TYPE: PRT
<213> ORGANISM: homo sapiens

<400> SEQUENCE: 32

Ala Arg Leu Thr Gly Asp Arg Gly Phe Asp Tyr Tyr Ser Gly Met Asp
1               5                   10                  15
Val

<210> SEQ ID NO 33
<211> LENGTH: 107
<212> TYPE: PRT
<213> ORGANISM: homo sapiens

<400> SEQUENCE: 33

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Phe
                85                  90                  95

Thr Phe Gly Pro Gly Thr Lys Val Asp Ile Lys
            100                 105

<210> SEQ ID NO 34
<211> LENGTH: 7
<212> TYPE: PRT
<213> ORGANISM: homo sapiens

<400> SEQUENCE: 34

Gln Ser Val Ser Ser Ser Tyr
1               5

<210> SEQ ID NO 35
<211> LENGTH: 8
<212> TYPE: PRT
<213> ORGANISM: homo sapiens

<400> SEQUENCE: 35

Gln Gln Tyr Gly Ser Ser Phe Thr
1               5

<210> SEQ ID NO 36
<211> LENGTH: 119
<212> TYPE: PRT
<213> ORGANISM: homo sapiens

<400> SEQUENCE: 36

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Gly Ile Ser Trp Val Arg Gln Ala Pro Gly Pro Gly Leu Glu Trp Met
            35                  40                  45

Gly Arg Ile Ile Pro Ile Leu Gly Ile Ala Asn Tyr Ala Gln Lys Phe
```

```
                        50                  55                  60
Gln Gly Arg Val Thr Ile Thr Ala Asp Lys Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Gln Glu Tyr Ser Ser Asn Trp Tyr Tyr Trp Gly Gln Gly
            100                 105                 110

Thr Leu Val Thr Val Ser Ser
        115

<210> SEQ ID NO 37
<211> LENGTH: 8
<212> TYPE: PRT
<213> ORGANISM: homo sapiens

<400> SEQUENCE: 37

Gly Gly Thr Phe Ser Ser Tyr Gly
 1               5

<210> SEQ ID NO 38
<211> LENGTH: 8
<212> TYPE: PRT
<213> ORGANISM: homo sapiens

<400> SEQUENCE: 38

Ile Ile Pro Ile Leu Gly Ile Ala
 1               5

<210> SEQ ID NO 39
<211> LENGTH: 12
<212> TYPE: PRT
<213> ORGANISM: homo sapiens

<400> SEQUENCE: 39

Ala Arg Asp Gln Glu Tyr Ser Ser Asn Trp Tyr Tyr
 1               5                  10

<210> SEQ ID NO 40
<211> LENGTH: 107
<212> TYPE: PRT
<213> ORGANISM: homo sapiens

<400> SEQUENCE: 40

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Arg Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Leu Tyr Gly Ser Ser Pro
                 85                  90                  95

Thr Phe Gly Pro Gly Thr Lys Val Asp Ile Lys
            100                 105

<210> SEQ ID NO 41
<211> LENGTH: 7
```

<212> TYPE: PRT
<213> ORGANISM: homo sapiens

<400> SEQUENCE: 41

Gln Ser Val Arg Ser Ser Tyr
1               5

<210> SEQ ID NO 42
<211> LENGTH: 8
<212> TYPE: PRT
<213> ORGANISM: homo sapiens

<400> SEQUENCE: 42

Gln Leu Tyr Gly Ser Ser Pro Thr
1               5

<210> SEQ ID NO 43
<211> LENGTH: 122
<212> TYPE: PRT
<213> ORGANISM: homo sapiens

<400> SEQUENCE: 43

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ser Ile Tyr Pro Gly Asp Ser His Thr Arg Tyr Arg Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Lys Gly Asp Phe Tyr Tyr Phe Phe Gly Leu Asp Val Trp
                100                 105                 110

Gly Gln Gly Thr Ala Ile Thr Val Ser Ser
            115                 120

<210> SEQ ID NO 44
<211> LENGTH: 107
<212> TYPE: PRT
<213> ORGANISM: homo sapiens

<400> SEQUENCE: 44

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
                100                 105

<210> SEQ ID NO 45
<211> LENGTH: 122
<212> TYPE: PRT
<213> ORGANISM: homo sapiens

<400> SEQUENCE: 45

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ser Ile Tyr Pro Gly Asp Ser His Thr Arg Tyr Arg Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Ala Gly Asp Tyr Tyr Tyr Tyr Asn Gly Met Asp Val Trp
            100                 105                 110

Gly Gln Gly Thr Thr Val Thr Val Ser Ser
        115                 120

<210> SEQ ID NO 46
<211> LENGTH: 107
<212> TYPE: PRT
<213> ORGANISM: homo sapiens

<400> SEQUENCE: 46

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Thr Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
            100                 105

<210> SEQ ID NO 47
<211> LENGTH: 122
<212> TYPE: PRT
<213> ORGANISM: homo sapiens

<400> SEQUENCE: 47

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

```
Gly Ile Ile Tyr Pro Gly Asp Ser Asp Thr Arg Tyr Ser Pro Ser Phe
        50                  55                  60

Gln Gly Gln Val Thr Ile Ser Val Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Lys Gly Asp Tyr Tyr His Tyr Gly Leu Asp Val Trp
            100                 105                 110

Gly Gln Gly Thr Thr Val Thr Val Ser Ser
            115                 120
```

<210> SEQ ID NO 48
<211> LENGTH: 109
<212> TYPE: PRT
<213> ORGANISM: homo sapiens

<400> SEQUENCE: 48

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Leu Thr Phe Gly Gly Gly Thr Lys Val Glu Ile Lys
            100                 105
```

<210> SEQ ID NO 49
<211> LENGTH: 122
<212> TYPE: PRT
<213> ORGANISM: homo sapiens

<400> SEQUENCE: 49

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Lys Gly Asp Tyr Tyr Tyr Phe Asn Gly Leu Asp Val Trp
            100                 105                 110

Gly Gln Gly Thr Thr Val Thr Val Ser Ser
            115                 120
```

<210> SEQ ID NO 50
<211> LENGTH: 109

<212> TYPE: PRT
<213> ORGANISM: homo sapiens

<400> SEQUENCE: 50

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Leu Thr Phe Gly Gly Gly Thr Lys Val Glu Ile Lys
            100                 105

<210> SEQ ID NO 51
<211> LENGTH: 122
<212> TYPE: PRT
<213> ORGANISM: homo sapiens

<400> SEQUENCE: 51

Glu Val Gln Leu Val Gln Ser Gly Ala Glu Val Lys Lys Pro Gly Glu
1               5                   10                  15

Ser Leu Lys Ile Ser Cys Gln Gly Ser Gly Tyr Arg Phe Ile Ser Tyr
            20                  25                  30

Trp Ile Gly Trp Val Arg Gln Met Pro Gly Lys Gly Leu Glu Trp Met
        35                  40                  45

Gly Arg Ile Tyr Pro Gly Asp Ser Asp Thr Arg Tyr Ser Pro Ser Phe
    50                  55                  60

Gln Gly Gln Val Thr Ile Ser Val Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Arg Gly Asp Tyr Tyr Phe Asn Gly Leu Asp Val Trp
            100                 105                 110

Gly Gln Gly Thr Thr Val Thr Val Ser Ser
        115                 120

<210> SEQ ID NO 52
<211> LENGTH: 107
<212> TYPE: PRT
<213> ORGANISM: homo sapiens

<400> SEQUENCE: 52

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu

```
                65                  70                  75                  80
Pro Glu Asp Phe Ala Val Tyr Tyr Cys Gln Gln Tyr Gly Ser Ser Leu
                    85                  90                  95

Thr Phe Gly Gly Gly Thr Lys Val Glu Ile Lys
                100                 105

<210> SEQ ID NO 53
<211> LENGTH: 122
<212> TYPE: PRT
<213> ORGANISM: homo sapiens

<400> SEQUENCE: 53

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Arg Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Thr Thr Ala Tyr
65                  70                  75                  80

Leu Gln Trp Ser Ser Leu Arg Ala Ser Asp Thr Ala Met Tyr Tyr Cys
                85                  90                  95

Ala Arg Gln Arg Gly Asp Tyr Tyr Phe Phe Gly Leu Asp Ile Trp
                100                 105                 110

Gly Gln Gly Thr Thr Val Thr Val Ser Leu
            115                 120

<210> SEQ ID NO 54
<211> LENGTH: 107
<212> TYPE: PRT
<213> ORGANISM: homo sapiens

<400> SEQUENCE: 54

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
                100                 105

<210> SEQ ID NO 55
<211> LENGTH: 122
<212> TYPE: PRT
<213> ORGANISM: homo sapiens

<400> SEQUENCE: 55

Glu Val Gln Leu Val Gln Ser Gly Ala Glu Val Lys Lys Pro Gly Glu
1               5                   10                  15
```

Ser Leu Lys Ile Ser Cys Lys Gly Ser Gly Tyr Arg Phe Ser Ser Tyr
            20                  25                  30

Trp Ile Gly Trp Val Arg Gln Met Pro Gly Lys Gly Leu Glu Trp Met
        35                  40                  45

Gly Ser Ile Phe Pro Gly Asp Ser Asp Thr Arg Tyr Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Ala Gly Asp Tyr Tyr Tyr Asn Gly Met Asp Val Trp
            100                 105                 110

Gly Gln Gly Thr Thr Val Thr Val Ser Ser
        115                 120

<210> SEQ ID NO 56
<211> LENGTH: 107
<212> TYPE: PRT
<213> ORGANISM: homo sapiens

<400> SEQUENCE: 56

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
            100                 105

<210> SEQ ID NO 57
<211> LENGTH: 8
<212> TYPE: PRT
<213> ORGANISM: homo sapiens
<220> FEATURE:
<221> NAME/KEY: MISC_FEATURE
<222> LOCATION: (3)..(3)
<223> OTHER INFORMATION: Xaa is Ser or Arg
<220> FEATURE:
<221> NAME/KEY: MISC_FEATURE
<222> LOCATION: (5)..(5)
<223> OTHER INFORMATION: Xaa is Ser, Thr, His or Ile
<220> FEATURE:
<221> NAME/KEY: MISC_FEATURE
<222> LOCATION: (6)..(6)
<223> OTHER INFORMATION: Xaa is Ser, Arg or Phe

<400> SEQUENCE: 57

Gly Tyr Xaa Phe Xaa Xaa Tyr Trp
1               5

<210> SEQ ID NO 58
<211> LENGTH: 8
<212> TYPE: PRT
<213> ORGANISM: homo sapiens

```
<220> FEATURE:
<221> NAME/KEY: MISC_FEATURE
<222> LOCATION: (2)..(2)
<223> OTHER INFORMATION: Xaa is Tyr
<220> FEATURE:
<221> NAME/KEY: MISC_FEATURE
<222> LOCATION: (7)..(7)
<223> OTHER INFORMATION: Xaa is Asp, Tyr or His

<400> SEQUENCE: 58

Ile Xaa Pro Gly Asp Ser Xaa Thr
1               5

<210> SEQ ID NO 59
<211> LENGTH: 17
<212> TYPE: PRT
<213> ORGANISM: homo sapiens
<220> FEATURE:
<221> NAME/KEY: MISC_FEATURE
<222> LOCATION: (3)..(3)
<223> OTHER INFORMATION: Xaa is Gln, His or Leu
<220> FEATURE:
<221> NAME/KEY: MISC_FEATURE
<222> LOCATION: (4)..(4)
<223> OTHER INFORMATION: Xaa is Arg, Ala, Thr or Lys
<220> FEATURE:
<221> NAME/KEY: MISC_FEATURE
<222> LOCATION: (5)..(5)
<223> OTHER INFORMATION: Xaa is Gly
<220> FEATURE:
<221> NAME/KEY: MISC_FEATURE
<222> LOCATION: (6)..(6)
<223> OTHER INFORMATION: Xaa is Asp
<220> FEATURE:
<221> NAME/KEY: MISC_FEATURE
<222> LOCATION: (7)..(7)
<223> OTHER INFORMATION: Xaa is Arg or none
<220> FEATURE:
<221> NAME/KEY: MISC_FEATURE
<222> LOCATION: (8)..(8)
<223> OTHER INFORMATION: Xaa is Gly or none
<220> FEATURE:
<221> NAME/KEY: MISC_FEATURE
<222> LOCATION: (9)..(9)
<223> OTHER INFORMATION: Xaa is Tyr or Phe
<220> FEATURE:
<221> NAME/KEY: MISC_FEATURE
<222> LOCATION: (10)..(10)
<223> OTHER INFORMATION: Xaa is Tyr or Asp
<220> FEATURE:
<221> NAME/KEY: MISC_FEATURE
<222> LOCATION: (12)..(12)
<223> OTHER INFORMATION: Xaa is Tyr, Phe or His
<220> FEATURE:
<221> NAME/KEY: MISC_FEATURE
<222> LOCATION: (13)..(13)
<223> OTHER INFORMATION: Xaa is Tyr, Asp, Ser, Phe or Asn
<220> FEATURE:
<221> NAME/KEY: MISC_FEATURE
<222> LOCATION: (15)..(15)
<223> OTHER INFORMATION: Xaa is Met or Leu
<220> FEATURE:
<221> NAME/KEY: MISC_FEATURE
<222> LOCATION: (17)..(17)
<223> OTHER INFORMATION: Xaa is Val or Ile

<400> SEQUENCE: 59

Ala Arg Xaa Xaa Xaa Xaa Xaa Xaa Xaa Xaa Tyr Xaa Xaa Gly Xaa Asp
1               5                   10                  15

Xaa

<210> SEQ ID NO 60
<211> LENGTH: 8
<212> TYPE: PRT
```

```
<213> ORGANISM: homo sapiens
<220> FEATURE:
<221> NAME/KEY: MISC_FEATURE
<222> LOCATION: (6)..(6)
<223> OTHER INFORMATION: Xaa is Asn or Ser

<400> SEQUENCE: 60

Gly Phe Thr Phe Ser Xaa Tyr Ala
1               5

<210> SEQ ID NO 61
<211> LENGTH: 8
<212> TYPE: PRT
<213> ORGANISM: homo sapiens
<220> FEATURE:
<221> NAME/KEY: MISC_FEATURE
<222> LOCATION: (2)..(2)
<223> OTHER INFORMATION: Xaa is Arg or Ser
<220> FEATURE:
<221> NAME/KEY: MISC_FEATURE
<222> LOCATION: (4)..(4)
<223> OTHER INFORMATION: Xaa is Gly or Ser
<220> FEATURE:
<221> NAME/KEY: MISC_FEATURE
<222> LOCATION: (5)..(5)
<223> OTHER INFORMATION: Xaa is Ala or Gly

<400> SEQUENCE: 61

Ile Xaa Gly Xaa Xaa Gly Ser Thr
1               5

<210> SEQ ID NO 62
<211> LENGTH: 11
<212> TYPE: PRT
<213> ORGANISM: homo sapiens
<220> FEATURE:
<221> NAME/KEY: MISC_FEATURE
<222> LOCATION: (8)..(8)
<223> OTHER INFORMATION: Xaa is Leu or Tyr

<400> SEQUENCE: 62

Ala Lys Arg Ile Trp Gly Pro Xaa Phe Asp Tyr
1               5                   10

<210> SEQ ID NO 63
<211> LENGTH: 8
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: Xaa is Arg or Ser

<400> SEQUENCE: 63

Gly Tyr Thr Phe Thr Xaa Tyr Gly
1               5

<210> SEQ ID NO 64
<211> LENGTH: 8
<212> TYPE: PRT
<213> ORGANISM: homo sapiens
<220> FEATURE:
<221> NAME/KEY: MISC_FEATURE
<222> LOCATION: (7)..(7)
<223> OTHER INFORMATION: Xaa is Lys or Asn

<400> SEQUENCE: 64

Ile Ser Ala Tyr Asn Gly Xaa Thr
1               5
```

```
<210> SEQ ID NO 65
<211> LENGTH: 15
<212> TYPE: PRT
<213> ORGANISM: homo sapiens

<400> SEQUENCE: 65

Ala Arg Ser Pro Leu Leu Trp Phe Glu Glu Leu Tyr Phe Asp Tyr
1               5                   10                  15

<210> SEQ ID NO 66
<211> LENGTH: 8
<212> TYPE: PRT
<213> ORGANISM: homo sapiens
<220> FEATURE:
<221> NAME/KEY: MISC_FEATURE
<222> LOCATION: (8)..(8)
<223> OTHER INFORMATION: Xaa is Gly or Ala

<400> SEQUENCE: 66

Gly Gly Thr Phe Ser Ser Tyr Xaa
1               5

<210> SEQ ID NO 67
<211> LENGTH: 11
<212> TYPE: PRT
<213> ORGANISM: homo sapiens
<220> FEATURE:
<221> NAME/KEY: MISC_FEATURE
<222> LOCATION: (9)..(9)
<223> OTHER INFORMATION: Xaa is Asn or Tyr
<220> FEATURE:
<221> NAME/KEY: MISC_FEATURE
<222> LOCATION: (10)..(10)
<223> OTHER INFORMATION: Xaa is Trp or Phe
<220> FEATURE:
<221> NAME/KEY: MISC_FEATURE
<222> LOCATION: (11)..(11)
<223> OTHER INFORMATION: Xaa is Tyr or Asp

<400> SEQUENCE: 67

Ala Arg Asp Gln Glu Tyr Ser Ser Xaa Xaa Xaa
1               5                   10

<210> SEQ ID NO 68
<211> LENGTH: 7
<212> TYPE: PRT
<213> ORGANISM: homo sapiens
<220> FEATURE:
<221> NAME/KEY: MISC_FEATURE
<222> LOCATION: (4)..(4)
<223> OTHER INFORMATION: Xaa is Ser or Arg
<220> FEATURE:
<221> NAME/KEY: MISC_FEATURE
<222> LOCATION: (6)..(6)
<223> OTHER INFORMATION: Xaa is Ser or Thr

<400> SEQUENCE: 68

Gln Ser Val Xaa Ser Xaa Tyr
1               5

<210> SEQ ID NO 69
<211> LENGTH: 10
<212> TYPE: PRT
<213> ORGANISM: homo sapiens
<220> FEATURE:
<221> NAME/KEY: MISC_FEATURE
<222> LOCATION: (2)..(2)
<223> OTHER INFORMATION: Xaa is Gln or Leu
<220> FEATURE:
<221> NAME/KEY: MISC_FEATURE
```

```
<222> LOCATION: (5)..(5)
<223> OTHER INFORMATION: Xaa is Ser or Thr
<220> FEATURE:
<221> NAME/KEY: MISC_FEATURE
<222> LOCATION: (7)..(7)
<223> OTHER INFORMATION: Xaa is Pro or none
<220> FEATURE:
<221> NAME/KEY: MISC_FEATURE
<222> LOCATION: (8)..(8)
<223> OTHER INFORMATION: Xaa is Pro, Leu, Arg or none
<220> FEATURE:
<221> NAME/KEY: MISC_FEATURE
<222> LOCATION: (9)..(9)
<223> OTHER INFORMATION: Xaa is Leu, Phe, Ile or none

<400> SEQUENCE: 69

Gln Xaa Tyr Gly Xaa Ser Xaa Xaa Xaa Thr
1               5                   10
```